United States Patent
DeLisa et al.

(10) Patent No.: US 9,394,344 B2
(45) Date of Patent: Jul. 19, 2016

(54) COMPOSITIONS AND METHODS FOR THE DISPLAY OF PROTEINS ON THE SURFACE OF BACTERIA AND THEIR DERIVED VESICLES AND USES THEREOF

(71) Applicant: Cornell Research Foundation, Inc., Ithaca, NY (US)

(72) Inventors: Matthew DeLisa, Ithaca, NY (US); Jae-Young Kim, Suwon (KR); David A. Putnam, Ithaca, NY (US); Anne M. Doody, Brooktondale, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 14/703,543

(22) Filed: May 4, 2015

(65) Prior Publication Data

US 2015/0307560 A1 Oct. 29, 2015

Related U.S. Application Data

(62) Division of application No. 12/601,133, filed as application No. PCT/US2008/064376 on May 21, 2008, now Pat. No. 9,051,565.

(60) Provisional application No. 60/939,506, filed on May 22, 2007.

(51) Int. Cl.
| | |
|---|---|
| *C07K 19/00* | (2006.01) |
| *C07K 14/005* | (2006.01) |
| *C12N 15/11* | (2006.01) |
| *C12N 15/10* | (2006.01) |
| *C07K 16/44* | (2006.01) |
| *C12N 15/113* | (2010.01) |

(52) U.S. Cl.
CPC ............. *C07K 14/005* (2013.01); *C07K 16/44* (2013.01); *C12N 15/1037* (2013.01); *C12N 15/11* (2013.01); *C12N 15/113* (2013.01); *C07K 2317/622* (2013.01); *C07K 2317/92* (2013.01); *C07K 2319/33* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| 7,056,700 B2 | 6/2006 | Galen |
| 7,329,807 B2 * | 2/2008 | Vadrucci et al. ............. 424/93.2 |
| 2002/0146430 A1 | 10/2002 | Galen |

OTHER PUBLICATIONS

Chen et al., "Engineering Outer Membrane Vesicles for Gene Delivery," School of Chemical and Biomolecular Engineering, Cornell University, Department of Biomedical Engineering, Ithaca, NY at: http://aiche.confex.com/aiche/2006/techprogram/P70675.HTM, pp. 1-2 (Printed Jul. 17, 2008).
Dhandayuthapani et al., "Green Fluorescent Protein as a Marker for Gene Expression and Cell Biology of Mycobacterial Interactions with Macrophages," Molecular Microbiology 17(5):901-12 (1995).
Galen et al., "Adaptation of the Endogenous *Salmonella enterica* Serover Typhi clyA-Encoded Hemolysin for Antigen Export Enhances the Immunogenicity of Anthrax Protective Antigen Domain 4 Expressed by the Attenuated Live-Vector Vaccine Strain CVD 908-htrA," Infection and Immunity 72(12):7096-106 (2004).
Georgiou et al., "Display of Heterologous Proteins on the Surface of Microorganisms: From the Screening of Combinatorial Libraries to Live Recombinant Vaccines," Nature Biotechnology 15:29-34 (1997).
International Search Report for International Patent Application No. PCT/US08/64376 (Oct. 27, 2008).
Kim et al., "Strategies for Expanding the Repertoire of Proteins that can be Displayed on the Outer Surface of *E. coli*," School of Chemical and Biomolecular Engineering, Cornell University, Ithaca, NY at: http://aiche.confex.com/aiche/2005/techprogram/P22253.HTM, p. 1 (Printed Oct. 3, 2008).
Written Opinion of the International Searching Authority for International Patent Application No. PCT/US08/64376 (Oct. 7, 2008).
Del Castillo et al., "Secretion of the *Escherichia coli* K-12 SheA Hemolysin is Independent of its Cytolytic Activity," FEMS Microbiol. Lett. 204(2):281-285 (2001).
Kim et al., "Engineered Bacterial Outer Membrane Vesicles with Enhanced Functionality," J. Mol. Biol. 380(1):51-66 (2008).
Galen et al., "Adaptation of the Endogenous *Salmonella enterica* Serovar Typhi clyA-Encoded Hemolysin for Antigen Export Enhances the Immunogenicity of Anthrax Protective Antigen Domain 4 Expressed by the Attenuated Live-Vector Vaccine Strain CVD 908-htrA," Infect. Immun. 72(12):7096-7106 (2004).
Wai et al., "Vesicle-Mediated Export and Assembly of Pore-Forming Oligomers of the Enterobacterial ClyA Cytotoxin," Cell 115:25-35 (2003).
Bemadac et al., "*Escherichia coli* tol-pal Mutants Form Outer Membrane Vesicles," J. Bacteriol. 180:4872-4878 (1998).

\* cited by examiner

*Primary Examiner* — Suzanne M Noakes
*Assistant Examiner* — Jae W Lee
(74) *Attorney, Agent, or Firm* — LeClairRyan, a Professional Corporation

(57) ABSTRACT

The present invention relates to compositions and methods for displaying proteins and polypeptides on the surface of cells and cellular vesicles. Methods and compositions for drug and vaccine delivery using cell surface display systems of the present invention are also disclosed.

19 Claims, 11 Drawing Sheets

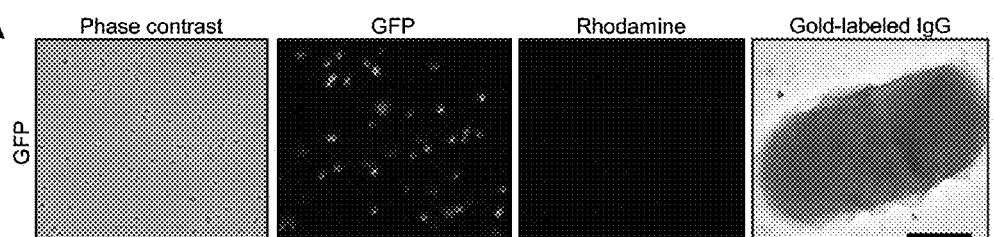
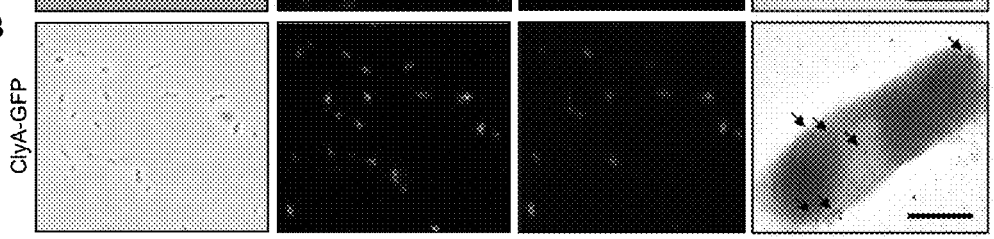

FIG.6A
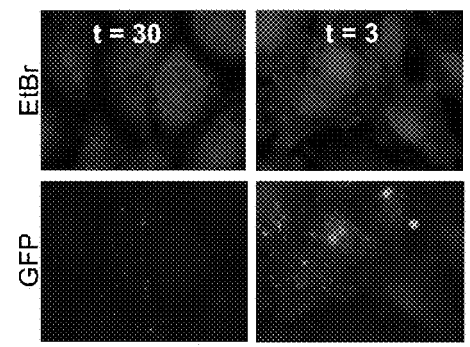
FIG.6C
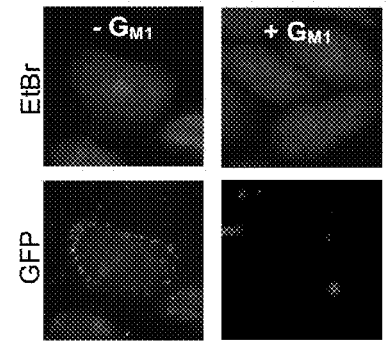
FIG.6B
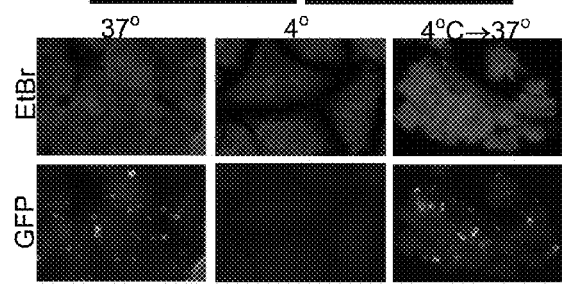
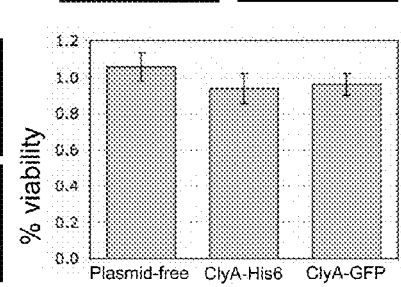
FIG.6D

COMPOSITIONS AND METHODS FOR THE DISPLAY OF PROTEINS ON THE SURFACE OF BACTERIA AND THEIR DERIVED VESICLES AND USES THEREOF

This application is a divisional application of U.S. patent application Ser. No. 12/601,133, which is a national stage application under 35 U.S.C. §371 of PCT Application No. PCT/US2008/064376, filed May 21, 2008, and claims the priority benefit of U.S. Provisional Patent Application Ser. No. 60/939,506, filed May 22, 2007, each of which is hereby incorporated by reference in its entirety.

The subject matter of this application was made with support from the United States Government under the National Institutes of Health, Grant No. NIBIB R21 EB005669. The U.S. Government has certain rights.

FIELD OF THE INVENTION

The present invention relates to compositions and methods for displaying proteins and polypeptides on the surface of cells and cell vesicles.

BACKGROUND OF THE INVENTION

Protein translocation is a highly conserved process that is essential to all life. Extracellular secretion of virulence factors is a strategy utilized by invading bacteria to establish a colonization niche, communicate with host cells, and modulate host defense and response. With few exceptions, bacterial protein secretion systems are characterized by the membrane translocation of a single protein or else small protein complexes (Christie et al., "Bacterial Type IV Secretion: Conjugation Systems Adapted to Deliver Effector Molecules to Host Cells," *Trends Microbiol* 8:354-60 (2000); Galan et al., "Type III Secretion Machines: Bacterial Devices for Protein Delivery into Host Cells," *Science* 284:1322-8 (1999); Gentschev et al., "The *E. coli* alpha-Hemolysin Secretion System and its Use in Vaccine Development," *Trends Microbiol* 10:39-45 (2002); Henderson et al., "Autotransporter Proteins, Evolution and Redefining Protein Secretion," *Trends Microbiol* 8:529-32 (2000); and Russel M., "Macromolecular Assembly and Secretion Across the Bacterial Cell Envelope: Type II Protein Secretion Systems," *J Mol Biol* 279:485-99 (1998)). Recently, however, the production and release of outer membrane vesicles (OMVs) has been demonstrated as a novel secretion mechanism for the transmission of a diverse group of proteins and lipids to mammalian cells (Kuehn M. J. et al., "Bacterial Outer Membrane Vesicles and the Host-Pathogen Interaction," *Genes Dev* 19:2645-55 (2005)). OMVs are small proteoliposomes with an average diameter of 50-200 nm that are constitutively released from the outer membrane of pathogenic and non-pathogenic species of Gram-negative bacteria during growth (Beveridge T. J., "Structures of Gram-Negative Cell Walls and their Derived Membrane Vesicles," *J Bacteriol* 181:4725-33 (1999)). Biochemical analysis has demonstrated that OMVs are comprised of outer membrane proteins, lipopolysaccharide, phospholipids and soluble periplasmic proteins, (Horstman et al., "Enterotoxigenic *Escherichia coli* Secretes Active Heat-Labile Enterotoxin Via Outer Membrane Vesicles," *J Biol Chem* 275:12489-96 (2000) and McBroom et al., "Outer Membrane Vesicles," In *EcoSal—Escherichia coli and Salmonella: Cellular and Molecular Biology* (III, R. C., ed.). ASM Press, Washington, D.C. (2005)) the latter of which become trapped in the vesicle lumen during release from the cell surface. OMVs are largely devoid of inner membrane and cytoplasm components although several studies indicate that chromosomal, phage and plasmid DNA can infiltrate OMVs as a means of OMV-mediated transfer of genetic information between bacteria (Dorward et al., "Export and Intercellular Transfer of DNA Via Membrane Blebs of *Neisseria gonorrhoeae*," *J Bacteriol* 171:2499-505 (1989); Kolling et al., "Export of Virulence Genes and Shiga Toxin by Membrane Vesicles of *Escherichia coli* 0157:H7," *Appl Environ Microbiol* 65:1843-8 (1999); Yaron et al., "Vesicle-Mediated Transfer of Virulence Genes from *Escherichia coli* 0157:H7 to Other Enteric Bacteria," *Appl Environ Microbiol* 66:4414-20 (2000); and Renelli et al., "DNA-Containing Membrane Vesicles of *Pseudomonas aeruginosa* PAO1 and their Genetic Transformation Potential," *Microbiology* 150:2161-9 (2004)).

An intriguing yet poorly understood phenomena pertaining to OMVs is the observation that certain membrane and/or soluble periplasmic proteins are enriched in vesicles while others are preferentially excluded. The majority of these enriched proteins happen to be virulence factors including, for example, *Escherichia coli* cytolysin A (ClyA), (Wai et al., "Vesicle-Mediated Export and Assembly of Pore-Forming Oligomers of the Enterobacterial ClyA Cytotoxin," *Cell* 115:25-35 (2003)) enterotoxigenic *E. coli* heat labile enterotoxin (LT), (Horstman et al., "Enterotoxigenic *Escherichia coli* Secretes Active Heat-Labile Enterotoxin Via Outer Membrane Vesicles," *J Biol Chem* 275:12489-96 (2000)) and *Actinobacillus actinomycetemcomitans* leukotoxin, (Kato et al., "Outer Membrane-Like Vesicles Secreted by *Actinobacillus actinomycetemcomitans* are Enriched in Leukotoxin," *Microb Pathog* 32:1-13. (2002)) whereas proteins that are excluded from OMVs include numerous unidentified outer membrane (OM) proteins (Kato et al., "Outer Membrane-Like Vesicles Secreted by *Actinobacillus actinomycetemcomitans* are Enriched in Leukotoxin," *Microb Pathog* 32:1-13. (2002)) as well as *E. coli* DsbA (Wai et al., "Vesicle-Mediated Export and Assembly of Pore-Forming Oligomers of the Enterobacterial ClyA Cytotoxin," *Cell* 115:25-35 (2003)). The preferential exclusion of proteins raises the interesting possibility that a yet-to-be determined sorting mechanism exists in the bacterial periplasm for discriminatory loading of a highly specific subset of proteins into OMVs (Wai et al., "Vesicle-Mediated Export and Assembly of Pore-Forming Oligomers of the Enterobacterial ClyA Cytotoxin," *Cell* 115:25-35 (2003) and McBroom et al., "Release of Outer Membrane Vesicles by Gram-Negative Bacteria is a Novel Envelope Stress Response," *Mol Microbiol* 63:545-58 (2007)). Moreover, the observation that certain virulence factors are enriched in vesicles suggests that OMVs may play a key role in bacterial pathogenesis by mediating transmission of active virulence factors and other bacterial envelope components to host cells. Indeed, numerous vesicle-associated virulence factors (e.g., adhesins, immunomodulatory compounds, proteases and toxins) have been shown to induce cytotoxicity, confer vesicle binding to and invasion of host cells, and modulate the host immune response (Horstman et al., "Enterotoxigenic *Escherichia coli* Secretes Active Heat-Labile Enterotoxin Via Outer Membrane Vesicles," *J Biol Chem* 275:12489-96 (2000); Fiocca et al., "Release of *Helicobacter pylori* Vacuolating Cytotoxin by Both a Specific Secretion Pathway and Budding of Outer Membrane Vesicles. Uptake of Released Toxin and Vesicles by Gastric Epithelium," *J Pathol* 188:220-6 (1999); Keenan et al., "A Role for the Bacterial Outer Membrane in the Pathogenesis of *Helicobacter pylori* Infection," *FEMS Microbiol Lett* 182: 259-64 (2000); Kadurugamuwa et al., "Delivery of the Non-Membrane-Permeative Antibiotic Gentamicin into Mammalian Cells by Using *Shigella flexneri* Membrane Vesicles," *Antimicrob Agents Chemother* 42:1476-83 (1998); and Kesty et al., "Enterotoxigenic *Escherichia coli* Vesicles Target Toxin Delivery into Mammalian Cells," *EMBO J* 23:4538-49 (2004)).

To date, one of the best studied vesicle-associated virulence factors is the 34-kDa cytotoxin ClyA (also called HlyE or SheA) found in pathogenic and non-pathogenic *E. coli* strains (Wai et al., "Vesicle-Mediated Export and Assembly of Pore-Forming Oligomers of the Enterobacterial ClyA Cytotoxin," *Cell* 115:25-35 (2003) and del Castillo et al., "The *Escherichia coli* K-12 SheA Gene Encodes a 34-kDa Secreted Haemolysin," *Mol Microbiol* 25:107-15 (1997)) and also in *Salmonella enterica* serovars Typhi and Paratyphi A (Oscarsson et al., "Characterization of a Pore-Forming Cytotoxin Expressed by *Salmonella enterica* serovars typhi and paratyphi A," *Infect Immun* 70:5759-69 (2002)). Structural studies indicate that the water-soluble form of ClyA is a bundle of four major α-helices, with a small surface-exposed hydrophobic beta-hairpin at the "head" end of the structure, and the N- and C-termini at the "tail" end (Wallace et al., "*E. coli* Hemolysin E (HlyE, ClyA, SheA): X-ray Crystal Structure of the Toxin and Observation of Membrane Pores by Electron Microscopy," *Cell* 100:265-76 (2000)) while lipid-associated ClyA forms an oligomeric pore complex comprised of either 8 or 13 ClyA subunits (Eifler et al., "Cytotoxin ClyA from *Escherichia coli* Assembles to a 13-meric Pore Independent of its Redox-State," *EMBO J* 25:2652-61 (2006) and Tzokov et al., "Structure of the Hemolysin E (HlyE, ClyA, SheA) Channel in its Membrane-Bound Form," *J Biol Chem* 281:23042-9 (2006)). Expression of the clyA gene is silenced in non-pathogenic *E. coli* K-12 laboratory strains by the nucleoid protein H-NS (Westermark et al., "Silencing and Activation of ClyA Cytotoxin Expression in *Escherichia coli*," *J Bacteriol* 182:6347-57 (2000)) but is derepressed in H-NS-deficient *E. coli*, thereby inducing cytotoxicity towards cultured mammalian cells (Gomez-Gomez et al., "Hns Mutant Unveils the Presence of a Latent Haemolytic Activity in *Escherichia coli* K-12," *Mol Microbiol* 19:909-10 (1996)). More recent evidence indicates that ClyA is exported from *E. coli* in OMVs and retains a cytolytically active, oligomeric conformation in the vesicles (Wai et al., "Vesicle-Mediated Export and Assembly of Pore-Forming Oligomers of the Enterobacterial ClyA Cytotoxin," *Cell* 115:25-35 (2003)). However, the route by which ClyA manages to cross the bacterial IM and assemble in OMVs remains a mystery, as it carries no canonical signal peptide (del Castillo et al., "The *Escherichia coli* K-12 SheA Gene Encodes a 34-kDa Secreted Haemolysin," *Mol Microbiol* 25:107-15 (1997)) and is not N-terminally processed (Ludwig et al., "Analysis of the SlyA-Controlled Expression, Subcellular Localization and Pore-Forming Activity of a 34 kDa Haemolysin (ClyA) from *Escherichia coli* K-12," *Mol Microbiol* 31:557-67 (1999)). Also undetermined is the role that ClyA plays in vesicle-mediated interactions with mammalian cells.

The present invention is directed to overcoming these and other deficiencies in the art.

SUMMARY OF THE INVENTION

A first aspect of the present invention is directed to a method of displaying a protein on a cell surface. This method involves providing either a fusion protein containing at least a portion of a ClyA protein and at least a portion of a second protein coupled to said ClyA protein or a nucleic acid construct encoding the fusion protein. The fusion protein or the nucleic acid construct is administered to a cell under conditions effective to display the fusion protein on the surface of the cell.

The present invention is also directed to a cell displaying a ClyA fusion protein, where the ClyA fusion protein comprises at least a portion of a ClyA protein and at least a portion of a second protein coupled to the ClyA protein.

Another aspect of the present invention relates to a method of displaying a protein on cell vesicles. This method involves providing either a fusion protein containing at least a portion of a ClyA protein and at least a portion of a second protein coupled to said ClyA protein or a nucleic acid construct encoding the fusion protein. The fusion protein or the nucleic acid construct is administered to a cell under conditions effective to display the fusion protein on the vesicles of the cell.

The present invention is also directed to a vesicle displaying a ClyA fusion protein, where the ClyA fusion protein comprises at least a portion of a ClyA protein and at least a portion of a second protein coupled to the ClyA protein.

Another aspect of the present invention is directed to a method of imaging cells, which involves providing either a fusion protein comprising at least a portion of a ClyA protein and marker protein coupled to the ClyA protein, or a nucleic acid construct encoding the fusion protein. The method further involves administering to a cell the fusion protein or the nucleic acid construct under conditions effective to display the fusion protein on the cell and imaging the cell based on the presence of the marker protein.

Another aspect of the present invention is directed to a method of sorting cells, which involves providing either a fusion protein comprising at least a portion of a ClyA protein and marker protein coupled to the ClyA protein, or a nucleic acid construct encoding the fusion protein. The method further involves administering to a cell the fusion protein or the nucleic acid construct under conditions effective to display the fusion protein on the cell and sorting the cell based on the presence of the marker protein.

The present invention is also directed to a method of screening a library of candidate compounds to identify compounds that bind to a target protein. This method involves providing the library of candidate compounds to be screened and a cell or a cell vesicle displaying a ClyA fusion protein. The ClyA fusion protein comprises at least a portion of the ClyA protein and at least a portion of a second protein, where the second protein of the ClyA fusion protein comprises the target protein. The method further includes contacting the library of candidate compounds with the cell or cell vesicle displaying the ClyA fusion target protein under conditions effective for the candidate compound to bind to the target protein and identifying those compounds that bind to the target protein.

Another aspect of the present invention relates to a method of delivering a therapeutic agent to a cell, which involves providing a vesicle displaying a ClyA fusion protein, where the ClyA fusion protein comprises at least a portion of the ClyA protein and at least a portion of a second protein. The vesicle contains the therapeutic agent to be delivered and the second protein of the ClyA fusion protein comprises a targeting protein. The vesicle is administered to a cell under conditions effective to deliver the therapeutic agent to the cell.

The present invention is also directed to a method of eliciting an immune response in a mammal. This method involves providing a cell or a cell vesicle displaying a ClyA fusion protein. The ClyA fusion protein comprises at least a portion of the ClyA protein and at least a portion of a second protein, where the second protein of the ClyA fusion protein comprises an antigenic protein or peptide capable of eliciting an immune response in the mammal. The cell or vesicle is administered to the mammal under conditions effective to elicit the immune response.

The present invention is also directed to drug and vaccine delivery vehicles consisting of a cell vesicles displaying a ClyA fusion protein. The ClyA fusion protein comprises at least a portion of the ClyA protein and at least a portion of a second protein.

The present invention describes the engineering of synthetic membrane vesicles (s-MVs) with non-native functions that are useful for a wide range of applications including, for instance, the analysis of the complete ClyA translocation process. Specifically, s-MVs have been programmed with enhanced functionality by creating chimeras between heterologous proteins such as green fluorescent protein (GFP) or β-lactamase (Bla) and ClyA. Using these engineered vesicles, it has been determined that ClyA is capable of co-localizing a variety of structurally diverse fusion partners to the surface of E. coli and their released vesicles, but only when the periplasmic disulfide bond-forming machinery was present. Importantly, these cell- and OMV-associated proteins retained their biological activity, suggesting that the functionality of natural OMVs can be easily expanded via the expression of ClyA chimeras.

BRIEF DESCRIPTION OF THE DRAWINGS

FIG. 1A is an electron micrograph of vesicles derived from JC8031 cells expressing ClyA-GFP. Bar is equal to 100 nm. FIG. 1B is a graph showing the Z-average particle size of 1 ml vesicle suspensions containing ~30 µg/ml total protein obtained from plasmid-free or ClyA-GFP-expressing JC8031 cells. Error bars represent the standard deviation of 3 replicates. FIG. 1C is a Western blot of vesicle fractions isolated from E. coli strain JC8031 expressing GFP, ClyA-GFP and GFP-ClyA. The blot was probed with anti-GFP serum. FIG. 1D is a Western blot showing protein detection and FIG. 1E is a graph of GFP fluorescence detection in periplasmic (per), cytoplasmic (cyt) and vesicle (OMV) fractions generated from JC8031 or BW25113 nlpI::Kan cells expressing ClyA-His6, ClyA-GFP, and GFP-ClyA. The ClyA-His6 blot was first probed with anti-polyhistidine. ClyA-GFP and GFP-ClyA blots were probed with anti-GFP. Following stripping of membranes, blots were reprobed with anti-OmpA serum or anti-DsbA serum as indicated. All fractions were generated from an equivalent number of cells. FIG. 1F is fluorescence microscopy images of vesicles generated from JC8031 cells expressing ClyA-His6, ClyA-GFP, and GFP-ClyA.

FIG. 2A is a electrophoretic analysis of the density gradient fractions from top (lane 1, lowest density) to bottom (lane 10, highest density) from JC8031 cells expressing ClyA-GFP. The bands corresponding to ClyA-GFP (top), OmpA (middle) and DsbA (bottom) were obtained with anti-GFP, anti-OmpA and anti-DsbA serum, respectively. Lane (i) represents input vesicles from the purified cell-free supernatant. FIG. 2B shows the quantification of the ClyA-GFP levels (filled squared) in each fraction as determined by densitometry using ImageJ software. Band intensity values were normalized to the maximum intensity corresponding to the ClyA-GFP measured in fraction 7. Also plotted is the GFP activity (open squares) measured in each fraction and normalized to the maximum activity, which also corresponds to fraction 7. FIG. 2C is fluorescence microscopy images of vesicles that migrated in gradient fractions 7 and 10.

FIGS. 3A-3B depict the microscopic analysis of ClyA expression. JC8031 cells grown at 37° C. in LB were induced to express GFP (FIG. 3A) and ClyA-GFP (FIG. 3B). For immunofluorescence microscopy, cells were treated with mouse monoclonal anti-GFP and subsequently with rhodamine-conjugated anti-mouse IgG. Panels show phase contrast microscopy and fluorescence microscopy using green and red emission filters as indicated. For immunoelectron microscopy, cells were treated with mouse monoclonal anti-GFP and subsequently with gold-conjugated anti-mouse IgG. Arrows indicate the 25 nm gold particles. The bars are equal to 500 nm.

FIG. 4A is a fluorescence microscopy analysis of the binding of fluorescent s-MVs (at a concentration of 0.35 µg/µl) to anti-E. coli antibody in the test channel and to the BSA-treated surface in the reference channel following 20 min of s-MV binding and 20 min PBS rinse. The measurements represent the size of the polydimethylsiloxane (PDMS) master. FIG. 4B is an overlay of SPR sensorgrams showing concentration-dependent binding of OMVs to immobilized anti-E. coli antibodies. For each binding experiment, 200 µl of OMV-containing samples (diluted to the concentrations indicated) were introduced to the test or reference channel for 20 min, followed by a 20 min PBS rinse. The SPR signal was recorded as wavelength shift (nm) versus time and plotted as a "sensorgram". All binding experiments were performed at 25° C.±1° C. with a flowrate of 10 µl/min. Each vesicle sample was assayed in triplicate and the standard error was determined to be less than 5%. FIG. 4C shows the vesicle standard curve generated using the SPR immunosensor. The steady-state SPR signal change was calculated by subtracting the average SPR signal during the PBS wash step following OMV binding from the average SPR signal collected during the initial PBS wash step prior to OMV addition. The equation $y=0.92 \ln(x)+3.63$ with an $R^2$ value of 0.95 describes the fit of a straight line through the logarithm of the data and was determined using SigmaPlot. The results are the average values calculated for the SPR signal change from three independent binding measurements with error bars showing±standard error. It is noteworthy that the lower detection limit for this system was determined to be 0.01 µg/µl (10% of the compensated SPR wavelength shift in the standard curve) and that for vesicle concentrations ≥0.18 µg/µl, SPR wavelength shifts >2.5 nm were recorded, which is ~10× greater than the baseline signal. FIG. 4D shows representative sensorgrams for antibody binding to s-MV surface-displayed GFP in test and reference channels. Channels were prepared identically so that fluorescent s-MVs were captured in both channels. The change in SPR signal over time was measured following addition of 1 µg/µl anti-GFP (black line) or 1 µg/µl anti-his6× (gray line) monoclonal antibody to surface-captured s-MVs. Antibody binding proceeded for 20 min followed by a 10 min PBS rinse. Each antibody was assayed in triplicate and the standard error was determined to be less than 5%.

FIG. 5C is a Western blot analysis of periplasmic and OMV fractions from JC8031 (dsbA+) and JC8031 dsbA::Kan cells (dsbA−) expressing either ClyA-GFP or ClyA-His6 as indicated. FIG. 5D shows the immunofluorescence of wt JC8031 (dsbA+, top left and center panels) and JC8031 dsbA::Kan cells (dsbA−, bottom left and center panel) expressing pClyA-GFP or pClyA-His6 as indicated and fluorescence of vesicles (right panels) derived from the same cells as indicated. For immunofluorescence, cells were treated with either mouse monoclonal anti-GFP or anti-polyhistidine antibodies and subsequently with rhodamine-conjugated anti-mouse IgG.

FIGS. 6A-6D show the interaction of ClyA-GFP vesicles with HeLa cells. FIG. 6A is fluorescent images of OMVs containing ClyA-GFP that were incubated with HeLa cells at 37° C. for 30 min or 3 hours as indicated. Fixed cells were stained with 0.5 mg/mL ethidium bromide (EtBr, upper panels) and visualized by fluorescence microscopy. FIG. 6B are fluorescent images showing the temperature dependence of OMV-HeLa cell interactions. This interaction was examined by incubation of HeLa cells with GFP-ClyA OMVs at the temperatures indicated. An equivalent number of OMVs (~150 µg) was used in all cases. FIG. 6C is fluorescent images comparing untreated (−$G_{M1}$) or pretreated (+$G_{M1}$) OMVs from JC8031 cells expressing ClyA-GFP that were incubated with HeLa cells at 37° C. for 3 hours. Fixed cells were stained with 0.5 mg/mL ethidium bromide (EtBr, upper panels) and visualized by fluorescence microscopy. An equivalent number of OMVs (~150 µg) was used in all cases. FIG. 6D shows the cytotoxicity of vesicles as measured using the MTS assay with HeLa cell cultures. Percent viability is reported as the viability of vesicle-treated HeLa cells normalized to the viability following treatment with PBS. HeLa cells were treated with vesicle solutions derived from plasmid-free JC8031 cells and JC8031 cells expressing ClyA-His6, ClyA-GFP. An equivalent number of OMVs (~150 µg) was used in all cases. Each sample was assayed in triplicate with error bars showing ±standard error.

FIG. 7A is fluorescence microscopy images of whole cells and vesicles generated from JC8031 cells expressing scFv.Dig, ClyA-scFv.Dig or Lpp-OmpA-scFv.Dig as indicated. For these studies, cells were grown and induced at room temperature followed by fluorescent labeling of cells or their derived vesicles with 1 µM Dig-BODIPY for 1 h at room temperature. FIG. 7B shows the genetic analysis of scFv.Dig localization, performed using flow cytometric analysis of strains and plasmids as indicated. Cells were grown and induced at room temperature followed by labeling with 1 µM Dig-BODIPY for 1 h at room temperature. Fluorescence is reported as the mean fluorescence for each cell population and was assayed in triplicate with error bars showing ±standard error.

FIG. 8A is a Western blot of purified his6-tagged recombinant proteins with anti-polyHistidine IgG. The expected molecular weights for ClyA, GFP, and ClyA-GFP fusion are 27 kDa, 34 kDa, and 61 kDa, respectively. FIG. 8B provides the relative hemolysis activity of ClyA, ClyA-GFP, and GFP. The intrinsic hemolysis activity of ClyA is retained in the ClyA-GFP fusion protein, and increases with increasing concentration. FIG. 8C shows the fluorescence intensity of GFP and recombinant ClyA-GFP in relative fluorescence units (RFU, arbitrary units). The fluorescence intensity of ClyA-GFP and GFP increases linearly with increasing concentration.

FIG. 9A is an electron micrograph of empty OMVs stained by uranyl acetate. The scale bar represents 200 nm. This image is also representative of recombinant OMV containing ClyA-GFP. FIG. 9B is a fluorescence micrograph of ClyA-GFP in association with recombinant OMV. FIG. 9C is a Western blot with anti-GFP antibodies of cell-free culture supernatants and OMV suspensions from cultures of E. coli expressing the empty plasmid vector or ClyA-GFP. FIG. 9D shows the Z-average hydrodynamic diameter of empty and recombinant OMV suspensions in PBS, as measured by dynamic light scattering. FIG. 9E shows the lipopolysaccharide content in empty and recombinant OMV suspensions, normalized by total protein content. The asterisk (*) denotes statistical significance ($p<0.05$), as determined by the student's t-test.

DETAILED DESCRIPTION OF THE INVENTION

Figure 1A:
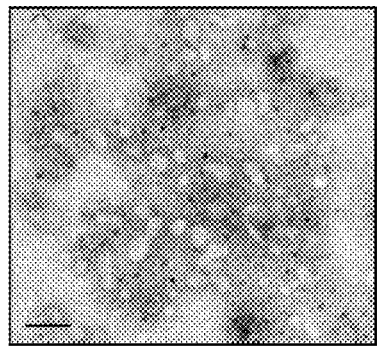
FIGS. 1A-1F show the subcellular localization of ClyA and ClyA fusion proteins.

A first aspect of the present invention is directed to a method of displaying a protein on a cell surface. This method involves providing either a fusion protein containing at least a portion of a ClyA protein and at least a portion of a second protein coupled to said ClyA protein or a nucleic acid construct encoding the fusion protein. The fusion protein or the nucleic acid construct is administered to a cell under conditions effective to display the fusion protein on the surface of the cell.

The present invention is also directed to a cell displaying a ClyA fusion protein, where the ClyA fusion protein comprises at least a portion of a ClyA protein and at least a portion of a second protein coupled to the ClyA protein.

Another aspect of the present invention relates to a method of displaying a protein on cell vesicles. This method involves providing either a fusion protein containing at least a portion of a ClyA protein and at least a portion of a second protein coupled to said ClyA protein or a nucleic acid construct encoding the fusion protein. The fusion protein or the nucleic acid construct is administered to a cell under conditions effective to display the fusion protein on the vesicles of the cell.

The present invention is also directed to a vesicle displaying a ClyA fusion protein, where the ClyA fusion protein comprises at least a portion of a ClyA protein and at least a portion of a second protein coupled to the ClyA protein.

The ClyA fusion protein used in accordance with the methods and compositions of the present invention may comprise either a full length or polypeptide fragment, analogue or derivative thereof of the ClyA protein from *E. coli* (Genbank Accession No. AJ001829). The amino acid sequence of the *E. coli* ClyA protein is set forth below as SEQ ID NO: 1:

```
Met Thr Glu Ile Val Ala Asp Lys Thr Val Glu Val Val Lys Asn Ala
1               5                   10                  15
Ile Glu Thr Ala Asp Gly Ala Leu Asp Leu Tyr Asn Lys Tyr Leu Asp
                20                  25                  30
Gln Val Ile Pro Trp Gln Thr Phe Asp Glu Thr Ile Lys Glu Leu Ser
                35                  40                  45
Arg Phe Lys Gln Glu Tyr Ser Gln Ala Ala Ser Val Leu Val Gly Asp
    50                  55                  60
Ile Lys Thr Leu Leu Met Asp Ser Gln Asp Lys Tyr Phe Glu Ala Thr
65                  70                  75                  80
Gln Thr Val Tyr Glu Trp Cys Gly Val Ala Thr Gln Leu Leu Ala Ala
                85                  90                  95
Tyr Ile Leu Leu Phe Asp Glu Tyr Asn Glu Lys Lys Ala Ser Ala Gln
                100                 105                 110
Lys Asp Ile Leu Ile Lys Val Leu Asp Asp Gly Ile Thr Lys Leu Asn
        115                 120                 125
Glu Ala Gln Lys Ser Leu Leu Val Ser Ser Gln Ser Phe Asn Asn Ala
    130                 135                 140
Ser Gly Lys Leu Leu Ala Leu Asp Ser Gln Leu Thr Asn Asp Phe Ser
145                 150                 155                 160
Glu Lys Ser Ser Tyr Phe Gln Ser Gln Val Asp Lys Ile Arg Lys Glu
                165                 170                 175
Ala Tyr Ala Gly Ala Ala Ala Gly Val Val Ala Gly Pro Phe Gly Leu
                180                 185                 190
Ile Ile Ser Tyr Ser Ile Ala Ala Gly Val Val Glu Gly Lys Leu Ile
        195                 200                 205
Pro Glu Leu Lys Asn Lys Leu Lys Ser Val Gln Asn Phe Phe Thr Thr
    210                 215                 220
Leu Ser Asn Thr Val Lys Gln Ala Asn Lys Asp Ile Asp Ala Ala Lys
225                 230                 235                 240
Leu Lys Leu Thr Thr Glu Ile Ala Ala Ile Gly Glu Ile Lys Thr Glu
                245                 250                 255
Thr Glu Thr Thr Arg Phe Tyr Val Asp Tyr Asp Asp Leu Met Leu Ser
                260                 265                 270
Leu Leu Lys Glu Ala Ala Lys Lys Met Ile Asn Thr Cys Asn Glu Tyr
        275                 280                 285
Gln Lys Arg His Gly Lys Lys Thr Leu Phe Glu Val Pro Glu Val
    290                 295                 300
```

The *E. coli* ClyA protein is encoded by the nucleic acid sequence of SEQ ID NO: 2:

```
agaaataaag acattgacgc atcccgcccg gctaactatg aattagatga agtaaaattt    60
attaatagtt gtaaacagg agtttcatta caatttatat atttaaagag gcgaatgatt    120
atgactgaaa tcgttgcaga taaaacggta gaagtagtta aaaacgcaat cgaaaccgca   180
gatggagcat tagatcttta taataaatat ctcgatcagg tcatcccctg gcagaccttt   240
gatgaaacca taaaagagtt aagtcgcttt aaacaggagt attcacaggc agcctccgtt   300
ttagtcggcg atattaaaac cttacttatg gatagccagg ataagtattt tgaagcaacc   360
caaacagtgt atgaatggtg tggtgttgcg acgcaattgc tcgcagcgta tattttgcta   420
```

```
tttgatgagt acaatgagaa gaaagcatcc gcccagaaag acattctcat taaggtactg     480
gatgacggca tcacgaagct gaatgaagcg caaaaatccc tgctggtaag ctcacaaagt     540
ttcaacaacg cttccgggaa actgctggcg ttagatagcc agttaaccaa tgatttttca     600
gaaaaaagca gctatttcca gtcacaggta gataaaatca ggaaggaagc atatgccggt     660
gccgcagccg gtgtcgtcgc cggtccattt ggattaatca tttcctattc tattgctgcg     720
ggcgtagttg aaggaaaact gattccagaa ttgaagaaca agttaaaatc tgtgcagaat     780
ttctttacca ccctgtctaa cacggttaaa caagcgaata agatatcga tgccgccaaa     840 ttgaaattaa ccaccgaaat agccgccatc ggtgagataa aaacggaaac tgaaacaacc     900
agattctacg ttgattatga tgatttaatg ctttctttgc taaaagaagc ggccaaaaaa     960
atgattaaca cctgtaatga gtatcagaaa agacacggta aaaagacact ctttgaggta     1020
cctgaagtct gataagcgat tattctctcc atgtactcaa ggtataaggt ttatcacatt     1080
```
20

In another embodiment of the present invention, the fusion protein comprises either a full length or polypeptide fragment, analogue or derivative thereof of the ClyA protein derived from *Salmonella enterica* serovar Typhi (Genbank Accession No. AJ313034). The amino acid sequence of the *S. enterica* Typhi ClyA protein is set forth below as SEQ ID NO: 3:

```
Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
```

-continued

```
                    245                 250                 255
Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val
    290                 295                 300
```

The *S. enterica* Typhi ClyA protein is encoded by the nucleic acid sequence of SEQ ID NO: 4:

```
ggaggtaata ggtaagaata ctttataaaa caggtactta attgcaattt atatatttaa    60
agaggcaaat gattatgacc ggaatatttg cagaacaaac tgtagaggta gttaaaagcg   120
cgatcgaaac cgcagatggg gcattagatc tttataacaa atacctcgac caggtcatcc   180
cctggaagac ctttgatgaa accataaaag agttaagccg ttttaaacag gagtactcgc   240
aggaagcttc tgttttagtt ggtgatatta agttttgct tatggacagc caggacaagt   300
attttgaagc gacacaaact gtttatgaat ggtgtggtgt cgtgacgcaa ttactctcag   360
cgtatatttt actatttgat gaatataatg agaaaaaagc atcagcccag aaagacattc   420
tcattaggat attagatgat ggtgtcaaga aactgaatga agcgcaaaaa tctctcctga   480
caagttcaca aagtttcaac aacgcttccg gaaaactgct ggcattagat agccagttaa   540
ctaatgattt ttcggaaaaa agtagttatt tccagtcaca ggtggataga attcgtaagg   600
aagcttatgc cggtgctgca gccgcatag tcgccggtcc gtttggatta attatttcct   660
attctattgc tgcgggcgtg attgaaggga aattgattcc agaattgaat aacaggctaa   720
aaacagtgca aaatttcttt actagcttat cagctacagt gaaacaagcg aataaagata   780
tcgatgcggc aaaattgaaa ttagccactg aaatagcagc aattggggag ataaaaacgg   840
aaaccgaaac aaccagattc tacgttgatt atgatgattt aatgctttct ttattaaaag   900
gagctgcaaa gaaaatgatt aacacctgta atgaatacca acaaagacac ggtaagaaga   960
cgcttttcga ggttcctgac gtctgataca ttttcattcg atctgtgtac ttttaacgcc  1020
cgatagcgta aagaaaatga gagacggaga aaaagcgata ttcaacagcc cgataaacaa  1080
gagtcgttac cgggctgacg ag                                          1102
```

In a further embodiment of the present invention, the fusion protein comprises either a full length or polypeptide fragment, analogue or derivative thereof of the ClyA protein from *Salmonella paratyphi* (Genbank Accession No. AJ313033). The amino acid sequence of the *S. paratyphi* ClyA protein is set forth below as SEQ ID NO: 5:

```
Met Thr Gly Ile Phe Ala Glu Gln Thr Val Glu Val Val Lys Ser Ala
1               5                   10                  15

Ile Glu Thr Ala Asp Gly Ala Leu Asp Phe Tyr Asn Lys Tyr Leu Asp
                20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
                100                 105                 110
```

Lys Asp Ile Leu Ile Arg Ile Leu Asp Asp Gly Val Asn Lys Leu Asn
            115                 120                 125

Glu Ala Gln Lys Ser Leu Leu Gly Ser Ser Gln Ser Phe Asn Asn Ala
        130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
            195                 200                 205

Pro Glu Leu Asn Asp Arg Leu Lys Ala Val Gln Asn Phe Phe Thr Ser
        210                 215                 220

Leu Ser Val Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
            275                 280                 285

Gln Gln Arg His Gly Lys Lys Thr Leu Leu Glu Val Pro Asp Ile
        290                 295                 300

The *S. paratyphi* ClyA protein is encoded by the nucleic acid sequence of SEQ ID NO: 6:

```
ggaggcaata ggtaggaata agttataaaa caatagctta attgcaattt atatatttaa      60
agaggcaaat gattatgact ggaatatttg cagaacaaac tgtagaggta gttaaaagcg     120
cgatcgaaac cgcagatggg gcattagatt tttataacaa ataccctcgac caggttatcc    180
cctggaagac ctttgatgaa accataaaag agttaagccg ttttaaacag gagtactcgc     240
aggaagcttc tgttttagtt ggtgatatta agttttgct tatggacagc caggataagt      300
attttgaagc gacacaaact gtttatgaat ggtgtggtgt cgtgacgcaa ttactctcag     360
cgtatatttt actatttgat gaatataatg agaaaaaagc atcagcgcag aaagacattc     420
tcatcaggat attagatgat ggcgtcaata aactgaatga agcgcaaaaa tctctcctgg     480
gaagttcaca agtttcaac aacgcttcag gaaaactgct ggcattagat agccagttaa      540
ctaatgattt ctcggaaaaa agtagttatt ccagtcaca ggtggataga attcgtaagg      600
aagcttatgc cggtgctgca gcaggcatag tcgccggtcc gtttggatta attatttcct     660
attctattgc tgcgggcgtg attgaaggga aattgattcc agaattgaat gacaggctaa     720
aagcagtgca aaatttcttt actagcttat cagtcacagt gaaacaagcg aataaagata     780
tcgatgcggc aaaattgaaa ttagccactg aaatagcagc aattggggag ataaaaacgg     840
aaaccgaaac aaccagattc tacgttgatt atgatgattt aatgctttct ttactaaaag     900
gagctgcaaa gaaatgatt aacacctgta atgaatacca acaaaggcac ggtaagaaga      960
cgcttctcga ggttcctgac atctgataca ttttcattcg ctctgtttac ttttaacgcc    1020
cgatagcgtg aagaaaatga gagacggaga aaaagcgata ttcaacagcc cgataaacaa    1080
gagtcgttac cgggctggcg ag                                            1102
```

In another embodiment of the present invention, the fusion protein comprises either a full length or polypeptide fragment, analogue or derivative thereof of the ClyA protein *Shigella flexneri* (Genbank Accession No. AF200955). The amino acid sequence of the *S. flexneria* ClyA protein is set forth below as SEQ ID NO: 7:

```
Met Thr Glu Ile Val Ala Asp Lys Thr Val Glu Val Val Lys Asn Ala
1               5                   10                  15

Ile Glu Thr Ala Asp Gly Ala Leu Asp Leu Tyr Asn Lys Tyr Leu Asp
                20                  25                  30

Gln Val Ile Pro Trp Gln Thr Phe Asp Glu Thr Ile Lys Glu Leu Ser
            35                  40                  45

Arg Phe Lys Gln Glu Tyr Ser Gln Ala Ala Ser Val Leu Val Gly Asp
        50                  55                  60

Ile Lys Thr Leu Leu Met Asp Ser Gln Asp Lys Tyr Phe Glu Ala Thr
65                      70                  75                  80

Gln Thr Val Tyr Glu Trp Cys Gly Val Ala Thr Gln Leu Leu Ala Ala
                85                  90                  95

Tyr Ile Leu Leu Phe Asp Glu Tyr Asn Glu Lys Lys Ala Ser Ala Pro
                100                 105                 110

His
```

The *S. flexneria* ClyA protein is encoded by the nucleic acid sequence of SEQ ID NO: 8:

```
atgactgaaa tcgttgcaga taaaacggta gaagtagtta aaaacgcaat cgaaaccgca    60
gatggagcat tagatcttta taataaatat ctcgatcagg tcatccctg gcagaccttt    120
gatgaaacca taaagagtt aagtcgcttt aaacaggagt attcacaggc agcctccgtt    180
ttagtcggcg atattaaaac cttacttatg gatagccagg ataagtattt tgaagcaacc    240
caaacagtgt atgaatggtg tggtgttgcg acgcaattgc tcgcagcgta tattttgcta    300
tttgatgagt acaatgagaa gaaagcatcc gcccctcatt aaggtactgg atgacggcat    360
cacgaagctg aatgaagcgc aaaattccct gctggtaagc tcacaaagtt tcaacaacgc    420
ttccgggaaa ctgctggcgt tagatagcca gttaaccaat gattttcag aaaaaagcag    480
ctatttccag tcacaggtag ataaaatcag gaaggaagcg tatgccggtg ccgcagccgg    540
tgtcgtcgcc ggtccatttg gtttaatcat ttcctattct attgctgcgg gcgtagttga    600
agggaaactg attccagaat tgaagaacaa gttaaaatct gtgcagagtt tctttaccac    660
cctgtctaac acggttaaac aagcgaataa agatatcgat gccgccaaat tgaaattaac    720
caccgaaata gccgccatcg gggagataaa aacgaaaact gaaaccacca gattctatgt    780
tgattatgat gatttaatgc tttctttgct aaaagcagcg gccaaaaaaa tgattaacac    840
ctgtaatgag tatcagaaaa gacacggtaa aaagacactc tttgaggtac ctgaagtctg    900
ataa                                                                  904
```

In another embodiment, the fusion protein of the present invention, comprising either a full length or polypeptide fragment, analogue or derivative thereof of the ClyA protein is derived from a ClyA consensus sequence. A ClyA amino acid consensus sequence derived from the alignment of SEQ ID NOs: 1, 3, 5, and 7 is set forth below as SEQ ID NO:9:

```
Met Thr Xaa Ile Xaa Ala Xaa Xaa Thr Val Glu Val Val Lys Xaa Ala
1               5                   10                  15

Ile Glu Thr Ala Asp Gly Ala Leu Asp Xaa Tyr Asn Lys Tyr Leu Asp
                20                  25                  30
```

```
Gln Val Ile Pro Trp Xaa Thr Phe Asp Glu Thr Ile Lys Glu Leu Ser
             35              40                  45

Arg Phe Lys Gln Glu Tyr Ser Gln Xaa Ala Ser Val Leu Val Gly Asp
 50              55                  60

Ile Lys Xaa Leu Leu Met Asp Ser Gln Asp Lys Tyr Phe Glu Ala Thr
 65              70                  75                  80

Gln Thr Val Tyr Glu Trp Cys Gly Val Xaa Thr Gln Leu Leu Xaa Ala
             85                  90                  95

Tyr Ile Leu Leu Phe Asp Glu Tyr Asn Glu Lys Lys Ala Ser Ala Xaa
             100                 105                 110

Xaa
                                                                15
```

The ClyA consensus sequence of SEQ ID NO:9 is encoded by the nucleic acid sequence set forth in SEQ ID NO:10 below:

```
natgacngna atnnttgcag annaaacngt agangtagtt aaaancgcna tcgaaaccgc      60
agatggngca ttagatnttt ataanaaata nctcgancag gtnatcccct ggnagacctt     120
tgatgaaacc ataaaagagt taagncgntt taaacaggag tantcncagg nagcntcgt     180
tttagtnggn gatattaaan nnttncttat gganagccag ganaagtatt ttgaagcnac     240
ncaaacngtn tatgaatggt gtggtgtngn dacgcaattn ctcncagcgt atattttnct     300
atttgatgan tanaatgaga anaaagcatc ngcncnnnnn nnnnnnctca tnangntant     360
ngatganggn ntcannaanc tgaatgaagc gcaaaantcn ctnctgnnaa gntcacaaag     420
tttcaacaac gcttcnggna aactgctggc nttagatagc cagttaacna atgatttntc     480
ngaaaaaagn agntatttcc agtcacaggt ngatanaatn ngnaaggaag cntatgccgg     540
tgcngcagcn ggnntngtcg ccggtccntt tggnttaatn atttcctatt ctattgctgc     600
gggcgtnntt gaaggnaaan tgattccaga attgaannac angntaaaan cngtgcanan     660
tttctttacn ancntntcnn nnacngtnaa acaagcgaat aaagatatcg atgcngcnaa     720
attgaaatta nccacngaaa tagcngcnat nggngagata aaaacggaaa cngaaacnac     780
cagattctan gttgattatg atgatttaat gctttctttn ntaaaagnag cngcnaanaa     840
aatgattaac acctgtaatg antancanna aagncacggt aanaagacnc tnntngaggt     900
ncctganntc tgatan                                                     916
```

An alternative ClyA amino acid consensus sequence derived from the alignment of SEQ ID NOs: 1, 3, and 5 is set forth below as SEQ ID NO:11:

```
Met Thr Xaa Ile Xaa Ala Xaa Xaa Thr Val Glu Val Val Lys Xa

```
                   100                 105                  110
Lys Asp Ile Leu Ile Xaa Xaa Leu Asp Asp Gly Xaa Xaa Lys Leu Asn
            115                 120                 125

Glu Ala Gln Lys Ser Leu Leu Xaa Ser Ser Gln Ser Phe Asn Asn Ala
        130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Xaa Ile Arg Lys Glu
                165                 170                 175

Ala Tyr Ala Gly Ala Ala Ala Gly Xaa Val Ala Gly Pro Phe Gly Leu
            180                 185                 190

Ile Ile Ser Tyr Ser Ile Ala Ala Gly Val Xaa Glu Gly Lys Leu Ile
            195                 200                 205

Pro Glu Leu Xaa Xaa Xaa Leu Lys Xaa Val Gln Asn Phe Phe Thr Xaa
        210                 215                 220

Leu Ser Xaa Thr Val Lys Gln Ala Asn Lys Asp Ile Asp Ala Ala Lys
225                 230                 235                 240

Leu Lys Leu Xaa Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
                260                 265                 270

Leu Leu Lys Xaa Ala Ala Lys Lys Met Ile Asn Thr Cys Asn Glu Tyr
            275                 280                 285

Gln Xaa Arg His Gly Lys Lys Thr Leu Xaa Glu Val Pro Xaa Xaa
        290                 295                 300
```

The ClyA consensus sequence of SEQ ID NO:11 is encoded by the nucleic acid sequence set forth in SEQ ID NO:12 below:

```
ngangnaana nntannaata nnttntaaaa cannnnnttn attncaattt atatatttaa       60
agaggcnaat gattatgacn gnaatnnttg cagannaaac ngtagangta gttaaaancg      120
cnatcgaaac cgcagatggn gcattagatn tttataanaa atanctcgan caggtnatcc      180
cctggnagac ctttgatgaa accataaaag agttaagncg ntttaaacag gagtantcnc      240
aggnagcntc ngttttagtn ggngatatta aannnttnct tatgganagc cagganaagt      300
attttgaagc nacncaaacn gtntatgaat ggtgtggtgt ngngacgcaa ttnctcncag      360
cgtatattt nctatttgat gantanaatg agaanaaagc atcngcncag aaagacattc      420
tcatnangnt antngatgan ggnntcanna anctgaatga agcgcaaaaa tcnctnctgn      480
naagntcaca aagtttcaac aacgcttcng gnaaactgct ggcnttagat agccagttaa      540
cnaatgattt ntcngaaaaa agnagntatt tccagtcaca ggtngatana atnngnaagg      600
aagcntatgc cggtgcngca gcnggnnntg tcgccggtcc ntttggatta atnatttcct      660
attctattgc tgcgggcgtn nttgaaggna aantgattcc agaattgaan nacangntaa      720
aancngtgca naatttcttt acnancntnt cnnnnacngt naaacaagcg aataaagata      780
tcgatgcngc naaattgaaa ttanccacng aaatagcngc natnggngag ataaaaacgg      840
aaacngaaac aaccagattc tacgttgatt atgatgattt aatgctttct ttnntaaaag      900
nagcngcnaa naaaatgatt aacacctgta atgantanca nnaaagncac ggtaanaaga      960
cnctnntnga ggtncctgan ntctgataan nnntnattcn ntcnntntac tnnaangnn     1020
ngatanngtn nannananatn                                                 1039
```

In the ClyA amino acid consensus sequences provided supra, the Xaa residues can be any amino acid, but preferably a neutral or hydrophobic amino acid. In the ClyA nucleic acid consensus sequences, the n residue can be any nucleic acid.

As discussed supra, the ClyA fusion protein of the present invention may comprise a full length ClyA protein, analogue or derivative thereof. In another embodiment, the fusion protein of the present invention comprises a peptide or polypeptide fragment of the ClyA protein. Preferred polypeptide fragments of the ClyA protein are those that retain the capacity to undergo normal cellular transport and outer membrane vesicle (OMV) assembly. The protein or polypeptide fragments of ClyA may comprise any of the wildtype amino acid sequences provided in SEQ ID NOs: 1, 3, 5, or 7 or the consensus sequences of SEQ ID NOs: 9 and 11. Alternatively, the ClyA protein or polypeptide fragment may contain one or more amino acid substitutions or deletions. In a preferred embodiment, the ClyA protein or polypeptide is a variant containing amino acid substitutions or deletions which inactivate its hemolytic activity while maintaining its adhesion/invasion activity. Such amino acid substitutions are readily known in the art and include, for example, the triple mutation V185S-A187S-I193S reported by Wallace et al., "*E. coli* hemolysin E (HlyE, ClyA, SheA): X-ray Crystal Structure of the Toxin and Observation of Membrane Pores by Electron Microscopy," *Cell* 100:265-76 (2000), which is hereby incorporated by reference in its entirety, or the deletion of amino acids 183-202 within the transmembrane domain, as reported by del Castillo et al., "Secretion of the *Escherichia coli* K-12 SheA Hemolysin is Independent of its Cytolytic Activity," *FEMS Microbiol. Lett.* 204:281-285 (2001), which is hereby incorporated by reference in its entirety.

The ClyA fusion protein used in the accordance with the methods and compositions of the present invention further comprises at least a portion of a second protein (i.e. a fusion partner). In one embodiment the second protein is a marker protein. Marker proteins are well know in the art and include affinity protein markers, such as chitin binding protein, maltose binding protein, glutathione-s-transferase, and the poly (His) tag; epitope markers, such as the V5-tag, c-myc-tag or the HA-tag; and fluorescence protein markers such as the green fluorescent protein and variants thereof (e.g. blue fluorescent protein, yellow fluorescent protein, and cyan fluorescent protein). Many additional fluorescence protein markers are well known in the art and commercially available including, but not limited to, the monomeric Kusabira Orange (mKO) protein, Midori-Ishi cyan fluorescent protein, mCherry red fluorescent protein and the monomeric teal fluorescent protein.

In another embodiment, the second protein of the ClyA fusion protein comprises a ligand binding protein. Suitable ligand binding proteins, include high-affinity antibody fragments (e.g., Fab, Fab' and F(ab')$_2$), single-chain Fv antibody fragments, nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins.

The ClyA fusion protein of the present invention can further comprise at least a portion of an antigenic protein or peptide. Suitable antigenic proteins or peptides are those derived from pathogenic bacterial, fungal or viral organisms such as *Streptococcus* species, *Candida* species, *Brucella* species, *Salmonella* species, *Shigella* species, *Pseudomonas* species, *Bordetella* species, *Clostridium* species, Norwalk virus, *Bacillus anthracis*, *Mycobacterium tuberculosis*, human immunodeficiency virus (HIV), *Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species. Other suitable antigenic proteins or peptides include sexually transmitted disease agents, viral encephalitis agents, protozoan disease agents, fungal disease agents, bacterial disease agents, or cancer cell antigens (e.g. prostate specific antigen, TAG-72 and CEA, MAGE-1 and tyrosinase), transplant antigens (e.g. CD3 receptor) or autoimmune antigens (e.g. IAS chain), and combinations thereof.

The second protein of the ClyA fusion protein can also comprise a therapeutic protein. A therapeutic protein in the context of the present invention is any recombinant protein useful in treating a subject suffering from a condition amenable to protein therapy treatment. Such conditions include, but are in no way limited to, cancer, heart attack, stroke, cystic fibrosis, Gaucher's disease, diabetes, anaemia, and haemophilia.

A therapeutic protein may be an immunoregulatory molecule. Suitable immunoregulatory molecules include, but are not limited to, growth factors, such as M-CSF, GM-CSF; and cytokines, such as IL-2, IL-4, IL-5, IL-6, IL-10, IL-12 or IFN-gamma.

The ClyA fusion proteins used in accordance with the methods of the present invention can be generated as described herein or using any other standard technique known in the art. For example, the fusion polypeptide can be prepared by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the ClyA polypeptide or protein is inserted into an expression vector in which the polynucleotide encoding the second polypeptide is already present. The second polypeptide or protein of the fusion protein can be fused to the N-, or preferably, to the C-terminal end of the ClyA polypeptide or protein.

Fusions between the ClyA protein or polypeptide and a second protein or polypeptide may be such that the amino acid sequence of the ClyA protein or polypeptide is directly contiguous with the amino acid sequence of the second protein. Alternatively, the ClyA portion may be coupled to the second protein or polypeptide by way of a linker sequence such as the flexible 5-residue Gly linker described herein or the flexible linkers from an immunoglobulin disclosed in U.S. Pat. No. 5,516,637 to Huang et al, which is hereby incorporated by reference in its entirety. The linker may also contain a protease-specific cleavage site so that the second protein may be controllably released from ClyA. Examples of protease sites include those specific to cleavage by factor Xa, enterokinase, collagenase, Igase (from *Neisseria gonorrhoeae*), thrombin, and TEV (Tobacco Etch Virus) protease.

Once the fusion protein is constructed, the nucleic acid construct encoding the protein is inserted into an expression system to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by Sambrook et al., *Molecular Cloning: A Laboratory Manual*, Cold Springs Laboratory Press, Cold Springs Harbor, New York (1989), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18 or pBR322 may be used.

Different genetic signals and processing events control many levels of gene expression (e.g., DNA transcription and messenger RNA ("mRNA") translation) and subsequently the amount of fusion protein that is displayed on the cell or vesicle surface. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression and surface display. Depending upon the host system utilized, any one of a number of suitable promoters may be used. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Host cells suitable for expressing and displaying the ClyA fusion on the cell surface or cell vesicle surface include any one of the more commonly available gram negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S dysenteriae, Neisseria gonorrhoeae, N. meningitides, Haemophilus influenzae H. pleuropneumoniae, Pasteurella haemolytica, P. multilocida, Legionella pneumophila, Treponema pallidum, T. denticola, T. orales, Borrelia burgdorferi, Borrelia spp. Leptospira interrogans, Klebsiella pneumoniae, Proteus vulgaris, P. morganii, P. mirabilis, Rickettsia prowazeki, R. typhi, R. richettsii, Porphyromonas (Bacteroides) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitens is, B. can is, Spirillum minus, Pseudomonas mallei, Aeromonas hydrophila, A salmonicida*, and *Yersinia pestis*. Methods for transforming/transfecting host cells with expression vectors are well-known in the art and depend on the host system selected as described in Sambrook et al., Molecular Cloning: *A Laboratory Manual*, Cold Springs Laboratory Press, Cold Springs Harbor, New York (1989), which is hereby incorporated by reference in its entirety.

Following transformation of the host cell with an expression vector comprising the nucleic acid construct encoding the ClyA fusion protein, the CylA fusion protein is expressed and displayed on the cell surface as well as the surface of outer membrane vesicles.

In one embodiment of the present invention, a plurality of proteins or polypeptides are displayed on the surface of a plurality of cells or cell vesicles. The plurality of proteins or polypeptides displayed on the cell or cell vesicle surface are ClyA fusion proteins where each ClyA fusion protein has a different second protein. The plurality of ClyA fusion proteins forms a library of proteins or peptides that are amenable to cell or cell vesicle surface display.

The cell and vesicle surface display of polypeptide or protein libraries generated in accordance with the methods of the present invention can be used to facilitate the identification of high affinity antibodies, antibody targets, or other specific ligand binding proteins or small molecules. In addition to facilitating the identification of protein-ligand binding interactions, cell and cell vesicle surface display of polypeptides can also be used to assay for other desirable protein properties including catalytic activity, inhibitory activity, and altered structural conformations.

In a preferred embodiment of the present invention, the library of polypeptides displayed on the cell or vesicle surface comprise a library of antibodies, antibody fragments, or fluorobodies. As shown herein, the fusion of ClyA to a nucleic acid encoding an antibody facilitates antibody display on the surface of a host cell or cellular vesicle. Nucleic acids encoding antibodies or antibody fragments can be obtained from an animal immunized with a selected antigen; alternatively, antibody genes from other sources can be used, such as those produced by hybridomas or produced by mutagenesis of a known antibody gene. One preferred method of obtaining nucleic acid segments is to isolate mRNA from antibody cells of an immunized animal. The mRNA may be amplified, for example by PCR, and used to prepare DNA segments to be used as fusion partners to ClyA. DNA segments that have been mutagenized from one or more DNAs that encode a selected antibody or antibody fragment may also be used.

Once an antibody expression library is prepared, the selected antigen for which one desires to identify and isolate specific antibody or antibodies is labeled with a detectable label. There are many types of detectable labels, including fluorescent labels (e.g fluorescein isothiocyanate (FITC), Alexa Fluor 488, phycoerytherin (PE), PE-Texas Red, PE-Cy5, PerCP, PerCP-Cy5.5, and PE-Cy7). The labeled antigen is contacted with the cells displaying the antibody expression library under conditions that allow specific antigen-antibody binding. Conditions can be varied so that only very tightly binding interactions occur; for example, by using very low concentrations of labeled antigen.

Identifying the antibody or antibody fragment expressing cells may be accomplished by methods that depend on detecting the presence of the bound detectable label. A particularly preferred method for identification and isolation is cell sorting or flow cytometry such as Fluorescent Activated Cell Sorting (FACS).

The present invention is also directed to a method of screening a library of candidate compounds to identify a compound that binds to a target protein. This method involves providing the library of candidate compounds to be screened and a cell or a cell vesicle displaying a ClyA fusion protein.

The ClyA fusion protein comprises at least a portion of the ClyA protein and at least a portion of a second protein, where the second protein of the ClyA fusion protein comprises the target protein. The method further includes contacting the library of candidate compounds with the cell or cell vesicle displaying the ClyA fusion target protein under conditions effective for the candidate compound to bind to the target protein and identifying those compounds that bind to the target protein.

Another aspect of the present invention relates to methods of imaging cells. This method involves providing either a fusion protein containing at least a portion of the ClyA protein and a marker protein coupled to said ClyA protein or a nucleic acid construct encoding the fusion protein. The method further involves administering to a cell the fusion protein or the nucleic acid construct under conditions effective to display the fusion protein on the cell and imaging the cell based on the presence of the marker protein.

Any of the marker proteins described supra can be used as the ClyA fusion partner to facilitate the method of imaging cells. In a preferred embodiment, the marker protein is a fluorescent marker protein. As discussed supra, there are a number of fluorescence protein markers that are well known in the art and commercially available, including for example, Green Fluorescent Protein (GFP) and all of its variants (e.g. BlueFP, YellowFP, CyanFP) that would facilitate the imaging of cells in accordance with this aspect of the invention.

Cell imaging can be achieved using any fluorescence based microscopy method known in the art including, but not limited to, epifluorescence microscopy, two-photon excitation microscopy, or confocal microscopy.

Another aspect of the present invention relates to a method of sorting cells. This method involves providing either a fusion protein containing at least a portion of the ClyA protein and a marker protein coupled to said ClyA protein or a nucleic acid construct encoding the fusion protein. The method further involves administering to a cell the fusion protein or the nucleic acid construct under conditions effective to display the fusion protein on the cell and sorting the cell based on the presence of the marker protein.

Any of the marker proteins described supra can be used as the ClyA fusion partner to facilitate the method of sorting cells. For example, the second protein of the fusion protein can comprise a marker protein having a polyhistidine-tag (His-tag). Cells displaying the fusion protein and, therefore, the His-tag can be readily sorted using affinity purification media such as, NTA-agarose, HisPur resin or Talon resin. Like the his-tag, other protein marker "tags" including the V5-tag, c-myc-tag or the HA-tag can also be adapted for cell sorting purposes.

The marker protein in accordance with this aspect of the invention can also be any ligand or ligand binding protein which can be sorted based on its selective binding to its respective binding partner. Magnetic activated cell sorting (MACS) using Dynal® Dynabeads® is an exemplary method of cell sorting based on this methodology. Dynabeads® are small magnetic beads which are covered with any desired ligand (e.g. antibody, protein, or antigen) having affinity for the target marker protein. Once the target protein is bound to the Dynabead®, the beads are bound to a magnetic column, which removes the target protein (and cell) from a mixed sample or solution. The bead bound cells are then eluted from the magnetic column.

In a preferred embodiment, the marker protein is a fluorescent marker protein and the cells are sorted by FACS. Any of the fluorescence protein markers discussed supra are suitable for facilitating the sorting of cells in accordance with this aspect of the invention. Generally, fluorescent proteins are chosen which have an excitation wavelength that is matched to the wavelength of illuminating light (typically in the range of about 485 to about 491 nm) and emission spectra that can be detected by an appropriate detector device. By way of example, many fluorescent proteins have an emission maxima in a range of about 510 to about 750 nm.

The optical detection systems used for cell sorting have one or more light sources, preferably in the form of one or more amplified or collimated beams of light, that are able to excite the fluorescent marker protein; and one or more detectors that are able to detect the fluorescence emissions caused by the marker protein. Suitable optical detection systems include, without limitation, single-laser flow cytometers; dual- or multiple-laser flow cytometers; and hematology analyzers equipped with an appropriate illumination device (e.g., diode, laser, etc.).

Another aspect of the present invention relates to a method of delivering a therapeutic agent to a cell, which involves providing a vesicle displaying a ClyA fusion protein, where the ClyA fusion protein comprises at least a portion of the ClyA protein and at least a portion of a second protein. The vesicle contains the therapeutic agent to be delivered and the second protein of the ClyA fusion protein comprises a targeting protein. The vesicle is administered to a cell under conditions effective to deliver the therapeutic agent to the cell.

Therapeutic agents may be encapsulated in membrane vesicles by culturing the microorganisms capable of producing membrane vesicles in the presence of the therapeutic agents. Membrane vesicles are typically obtained from gram-negative bacteria. Suitable microorganisms for producing the membrane vesicles include, but not limited to, Pseudomonas aeruginosa, Escherichia coli, Salmonella gastroenteritis (typhimirium), S. typhi, S. enteriditis, Shigella flexneri, S. sonnie, S dysenteriae, Neisseria gonorrhoeae, N. meningitides, Haemophilus influenzae H. pleuropneumoniae, Pasteurella haemolytica, P. multilocida, Legionella pneumophila, Treponema pallidum, T. denticola, T. orates, Borrelia burgdorferi, Borrelia spp. Leptospira interrogans, Klebsiella pneumoniae, Proteus vulgaris, P. morganii, P. mirabilis, Rickettsia prowazeki, R. typhi, R. richettsii, Porphyromonas (Bacteroides) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitens is, B. can is, Spirillum minus, Pseudomonas mallei, Aeromonas hydrophila, A salmonicida, and Yersinia pestis. Therapeutic agents may also be produced by the microorganism by transforming the microorganism with a gene which expresses the therapeutic agent preferably in the periplasmic space.

Any of a wide variety of therapeutic agents may be encapsulated in cellular vesicles including antimicrobial agents, metabolic regulators, immune modulators, antiproliferative agents, chemotherapeutics, etc. The therapeutic agent can be a nucleic acid molecule, protein, or small molecule.

The ClyA fusion protein displayed on the cell vesicle surface will target the therapeutic agent to the tissue where it is most needed. The second protein of the ClyA fusion protein comprises the target protein. Suitable target proteins include any of the ligand binding proteins described supra, especially antibodies or antibody fragments directed to cell specific surface receptors and proteins. Alternatively, the target protein can be any ligand that will bind to a cell-specific surface receptor. Targeting the vesicle containing the therapeutic agent to only the tissues at risk reduces the exposure of other tissues to potential toxic side effects of the therapeutic agent.

Slow sustained release of therapeutic agents from vesicles will also prolong the residence time of the therapeutic agent in areas where it is most needed.

The present invention is also directed to a method of eliciting an immune response in a mammal. This method involves providing a cell or a cell vesicle displaying a ClyA fusion protein. The ClyA fusion protein comprises at least a portion of the ClyA protein and at least a portion of a second protein, where the second protein of the ClyA fusion protein comprises an antigenic protein or peptide capable of eliciting an immune response in the mammal. The cell or vesicle is administered to the mammal under conditions effective to elicit the immune response.

Any antigenic protein or peptide capable of eliciting an immune response in a mammal can be used in accordance with this aspect of the present invention. A number of exemplary antigens derived from infectious or pathogenic bacterial, fungal or viral organisms, as well as, tumor cell specific, autoimmune or transplant antigens are described supra.

The present invention is also directed to drug and vaccine delivery vehicles consisting of a cell vesicles displaying a ClyA fusion protein. The ClyA fusion protein comprises at least a portion of the ClyA protein and at least a portion of a second protein.

Drug delivery vehicles of the present invention comprise the drug or therapeutic agent to be delivered encapsulated by the cell vesicle as described supra. Suitable drugs or therapeutic agents to be delivered include nucleic acid molecules, e.g. RNAi, therapeutic proteins, or small molecules. Delivery of the drug or therapeutic agent to its target cell is facilitated by display of the ClyA fusion protein on the surface of the cell vesicle where the second protein of the ClyA fusion protein comprises a cell specific targeting protein as described supra.

Vaccine delivery vehicles of the present invention may either be prophylactic (i.e. to prevent infection) or therapeutic (i.e. to treat infection), but will typically be prophylactic. In this embodiment of the present invention, the ClyA fusion protein contains a second immunogenic protein or antigen. Suitable antigenic proteins and peptides are described supra. In a preferred embodiment, the second protein of the ClyA fusion protein is a vaccine subunit protein. Immunogenic compositions used as vaccines comprise an immunologically effective amount of antigen(s), as well as any other components, as needed. An immunologically effective amount, is the amount administrated to an individual, either in a single dose or as part of a series, that is effective for treatment or prevention. The amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

Methods for preparing cellular vesicles suitable for administration as drug and vaccine delivery vehicles and methods and formulations for administration of cellular vesicles are known in the art and described herein and in WO2002/0028215 to Kadurugamuwa and Beveridge, WO2006/024946 to Oster et al., and WO2003/051379 to Foster et al., which are hereby incorporated by reference in their entirety.

The drug or vaccine delivery vehicles of the present invention can be formulated into pharmaceutically acceptable compositions for patient administration. An effective quantity of the active vesicles are combined with a pharmaceutically acceptable vehicle as described, for example, in Remington's Pharmaceutical Sciences (Remington's Pharmaceutical Sciences, Mack Publishing Company, Easton, Pa., USA 1985, which is hereby incorporated by reference in its entirety). On this basis, the pharmaceutical compositions include, albeit not exclusively, solutions of the membrane vesicles in association with one or more pharmaceutically acceptable vehicles or diluents, and contained in buffered solutions with a suitable pH and iso-osmotic with the physiological fluids.

The vesicle delivery vehicles of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The delivery vehicles of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the delivery vehicles may be incorporated with excipients and used in the form of tablets, capsules, elixirs, suspensions, syrups, and the like. Such compositions and preparations should contain at least 0.1% of delivery vehicle. The percentage of the delivery vehicle carrying the drug or vaccine in these compositions may, of course, be varied and may conveniently be between about 2% to about 60% of the weight of the unit. The amount of drug or vaccine in such therapeutically useful compositions is such that a suitable dosage will be obtained. Preferred compositions according to the present invention are prepared so that an oral dosage unit contains between about 1 and 250 mg of active drug or vaccine.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The delivery vehicles containing a therapeutic agent or carrying a vaccine antigen may also be administered parenterally. Solutions or suspensions of these vehicles can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The delivery vehicles of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The following examples illustrate various methods for compositions in the treatment method of the invention. The examples are intended to illustrate, but in no way limit, the scope of the invention.

EXAMPLES

Example 1

Bacterial Strains, Plasmids and Growth Conditions

The bacterial strains and plasmids used in these examples are described in Table 1.

TABLE 1

| Bacterial strains and plasmids | | |
|---|---|---|
| Bacterial strain or plasmid | Genotype/Description | Source (which are hereby incorporated by reference in their entirety) |
| 1292 | supE hsdS met gal lacY tonA | Bernadac et al., "*Escherichia coli* tol-pal Mutants Form Outer Membrane Vesicles," J Bacteriol 180:4872-8 (1998) |
| JC8031 | 1292 ΔtolRA | Bernadac et al., "*Escherichia coli* tol-pal Mutants Form Outer Membrane Vesicles," J Bacteriol 180:4872-8 (1998) |
| BW25113 | lacI$^q$ rrnB$_{T14}$ ΔlacZ$_{WJ16}$ hsdR514 ΔaraBAD$_{AH33}$ ΔrhaBAD$_{LD78}$ | Datsenko et al., "One-Step Inactivation of Chromosomal Genes in *Escherichia coli* K-12 using PCR Products," Proc Natl Acad Sci USA 97:6640-5 (2000) |
| BW25113 nlpI::Kan | BW25113 nlpI::Kan created via the method of Datsenko and Wanner | Baba et al., "Construction of *Escherichia coli* K-12 In-Frame, Single-Gene Knockout Mutants: the Keio Collection," Mol Syst Biol 2:2006 0008 (2006) |
| DHB4 | MC1000 phoR Δ (phoA) PvuII Δ (malF)3 F' [lacI$^q$ZYA pro] | Laboratory stock |
| DHA | DHB4 dsbA::Kan | Qi et al., "DnaK Promotes the Selective Export of Outer Membrane Protein Precursors in SecA-Deficient *Escherichia coli*," J Biol Chem 277:51077-83 (2002) |
| JCA | JC8031 dsbA::Kan | This study |
| pBAD18-Cm | araBAD promoter; pBR322 ori Cm$^r$ | Guzman et al., "Tight Regulation, Modulation, and High-Level Expression by Vectors Containing the Arabinose PBAD Promoter," J Bacteriol 177:4121-30 (1995) |
| pBAD18-Kan | araBAD promoter; pBR322 ori Cm$^r$ | Guzman et al., "Tight Regulation, Modulation, and High-Level Expression by Vectors Containing the Arabinose PBAD Promoter," J Bacteriol 177:4121-30 (1995) |
| pBAD24 | araBAD promoter; pBR322 ori Amp$^r$ | Guzman et al., "Tight Regulation, Modulation, and High-Level Expression by Vectors Containing the Arabinose PBAD Promoter," J Bacteriol 177:4121-30 (1995) |
| pClyA-His6 | *E. coli* clyA carrying a C-terminal 6x polyhistidine tag cloned in pBAD18-Cm | This study |
| pGFP | gfp-mut2 gene cloned in pBAD18-Cm | This study |
| pClyA-GFP | clyA gene fused to 5' end of gfp-mut2 in pBAD18-Cm | This study |
| pGFP-ClyA | clyA gene fused to 3' end of gfp-mut2 in pBAD18-Cm | This study |
| pΔss-Bla | Mature region of bla gene cloned in pBAD18-Kan | |
| pClyA-Bla | clyA gene fused to 5' end of bla in pBAD18-Kan | This study |
| pBla-ClyA | clyA gene fused to 3' end of bla in pBAD18-Kan | This study |

TABLE 1-continued

Bacterial strains and plasmids

| Bacterial strain or plasmid | Genotype/Description | Source (which are hereby incorporated by reference in their entirety) |
|---|---|---|
| pKEG01 | *Flavobacterium* sp. opd gene in pET78UF | Shimazu et al., "Thermally Triggered Purification and Immobilization of Elastin-OPH Fusions," Biotechnol Bioeng 81:74-9 (2003) |
| pOPH | opd gene cloned in pBAD24 | This study |
| pClyA-OPH | clyA gene fused to 5' end of opd in pBAD24 | This study |
| pOPH-ClyA | clyA gene fused to 3' end of opd in pBAD24 | This study |
| pLacZ | lacZ gene cloned in pBAD24 | This study |
| pClyA-LacZ | clyA gene fused to 5' end of lacZ in pBAD24 | This study |
| pB18D | anti-digoxin scFv fused to the 3' end of lpp-ompA cloned in pBAD18 | Daugherty et al., "Development of an Optimized Expression System for the Screening of Antibody Libraries Displayed on the *Escherichia coli* Surface," Protein Eng 12:613-21 (1999) |
| pB24D | anti-digoxin scFv fused to the 3' end of lpp-ompA cloned in pBAD24 | This study |
| pscFv.Dig | anti-digoxin scFv cloned in pBAD24 | This study |
| pClyA-scFv.Dig | clyA gene fused to 5' end of anti-digoxin scFv in pBAD24 | This study |
| pscFv.Dig-ClyA | clyA gene fused to 3' end of anti-digoxin scFv in pBAD24 | This study |
| pClyA (Δ293-303)-scFv.Dig | clyA with 10 C-terminal residues removed | This study |
| pClyA (4156-303)-scFv.Dig | clyA with 147 C-terminal residues removed | This study |
| pClyA (Y288G)-scFv.Dig | clyA with Tyr288 residue mutated to Gly | This study |

Strain JCA was made by introducing the dsbA::Kan allele into JC8031 cells by P1 vir transduction using DHA as the donor. Plasmid pClyA was constructed by ligating the PCR-amplified clyA gene into pBAD18-Cm between SacI and XbaI sites. Insertion of DNA encoding either the gfpmut2 gene (Crameri et al., "Improved Green Fluorescent Protein by Molecular Evolution Using DNA Shuffling," *Nat Biotechnol* 14:315-9 (1996) and DeLisa et al., "Genetic Analysis of the Twin Arginine Translocator Secretion Pathway in Bacteria," *J Biol Chem* 277:29825-31 (2002), which are hereby incorporated by reference in their entirety) or a 6× polyhistidine sequence between XbaI and HindIII sites resulted in plasmids pClyA-GFP and pClyA-His6, respectively. Plasmid pGFP-ClyA was constructed by first cloning the gfpmut2 gene between SacI and XmaI sites of pBAD18-Cm followed by insertion of the clyA gene between XmaI and XbaI sites. Plasmid pGFP was constructed by ligating the PCR-amplified gfpmut2 gene between SacI and HindIII sites of pBAD18-Cm. For ClyA-X fusions in pBAD24, each of the PCR-amplified partner genes (except for bla) was inserted between XmaI and SphI sites followed by clyA ligation between NcoI and XmaI sites. X-ClyA fusions were similarly constructed in pBAD24 with the ligations of fusion partner between NcoI and XmaI, and clyA between XmaI and SphI. Control plasmids without clyA were constructed by inserting the fusion partner, X, between NcoI and SphI of pBAD24. For Bla fusions with ClyA, a similar strategy as described above was used for inserting clyA and bla into plasmid pBAD18-Kan between SacI and XmaI and SphI sites. The gene encoding the Lpp-OmpA-scFv.Dig chimera in pB18D was amplified and ligated into pBAD24 between NcoI and SphI, resulting in pB24D. To generate pClyA(Δ156-303)-scFv.Dig, pClyA-scFv.Dig was digested with HpaI and XmaI and then self-ligated via blunt-end ligation after removal of overhanging basepairs. To generate pClyA(Δ293-303)-scFv.Dig, DNA encoding the first 292 amino acids of ClyA was PCR-amplified and inserted in place of wt clyA in pClyA-scFv.Dig. Plasmid pClyA(Y288G)-scFv.Dig was generated with pClyA-scFv.Dig as template for site-directed mutagenesis using a Stratagene QuickChange® site-directed mutagenesis kit. Cells were grown in LB broth with appropriate antibiotics: ampicillin, 100 μg/ml; chloramphenicol, 25 μg/ml; and kanamycin, 50 μg/ml. Cell growth was maintained at 37° C. unless otherwise noted. Protein synthesis was induced for 6 h by adding 0.2% arabinose when cells reached an $OD_{600} \approx 0.5$.

Example 2

Cell Culture

Human epithelial cervical carcinoma (HeLa) cells were obtained from the American Type Culture Collection (ATCC # CCL-2) and grown in Dulbecco's modified Eagle's minimal essential medium (DMEM) supplemented with 10% NuSerum, and 1% penicillin/streptomycin. Cells were maintained at 37° C. in a humidified atmosphere of 95% air, 5% $CO_2$. For fluorescence microscopy experiments, cells were grown on 12-mm circular glass coverslips for two days prior to experimentation.

Example 3

Subcellular Fractionation

Cytoplasmic and periplasmic fractions from cells expressing fusion proteins were generated by the cold osmotic shock procedure (Kim et al., "Twin-Arginine Translocation of Active Human Tissue Plasminogen Activator in *Escherichia coli*," *Applied and Environmental Microbiology* 71:8451-8459 (2005)), which is hereby incorporated by reference in its entirety) and the pellet remaining after removal of the soluble fraction was collected as the insoluble fraction.

Example 4

Isolation of Bacterial Vesicles

Vesicles were isolated from late log-phase bacterial cultures grown aerobically at 37° C. in LB broth (unless otherwise indicated) essentially as described previously (Wai et al., "Vesicle-Mediated Export and Assembly of Pore-Forming Oligomers of theEnterobacterial ClyA Cytotoxin," *Cell* 115:25-35 (2003), which is hereby incorporated by reference in its entirety). Briefly, bacterial cells were removed by centrifugation at 5,000×g for 15 min at 4° C. and the cell-free supernatants were filtered through a 0.2 μm-pore-size vacuum filter. Vesicles were collected from the filtered supernatant by ultracentrifugation at 141,000×g for 2 h at 4° C. in a 28 Ti rotor (Beckman Instruments, Inc., Fullerton, Calif.) and the pellet containing OMVs was carefully removed and suspended in PBS (pH 7.0). Vesicle preparations were plated on LB agar to confirm complete removal of bacterial cells. Vesicles preparations were kept at −20° C.

Example 5

Outer Membrane Vesicles Fractionation

Separation of pelleted outer membrane vesicle samples was performed as described (Horstman et al., "Enterotoxigenic *Escherichia coli* Secretes Active Heat-Labile Enterotoxin Via Outer Membrane Vesicles," *J Biol Chem* 275:12489-96 (2000), which is hereby incorporated by reference in its entirety). Briefly, vesicles were isolated as described above but suspended in 50 mM HEPES (pH 6.8), adjusted to 45% Optiprep (Sigma, St. Louis, Mo.) in 0.15 ml and transferred to the bottom of 12-ml ultracentrifugation tubes. Different Optiprep/HEPES layers were sequentially added as follows: 0.9 ml 35%, 0.9 ml 30%, 0.66 ml 25%, 0.66 ml 20%, 0.33 ml 15% and 0.33 ml 10%. Gradients were centrifuged (180,000×g, 180 min, 4° C.). A total of 10 fractions of equal volumes were sequentially removed and analysed by SDS-PAGE.

Example 6

Vesicle Characterization

The amount of vesicles in purified cell-free supernatant was determined by measuring the total protein concentration or the dry mass of vesicles according to published protocols (Kadurugamuwa et al., "Virulence Factors Are Released from *Pseudomonas aeruginosa* in Association with Membrane Vesicles During Normal Growth and Exposure to Gentamicin: A Novel Mechanism of Enzyme Secretion," *J Bacteriol* 177:3998-4008 (1995), which is hereby incorporated by reference in its entirety). Particle size distribution and zeta potential of vesicle samples containing approximately 30 μg/mL total protein in 1 mL of PBS were measured in a Nanosizer Nano ZS instrument (Malvern Instruments, Westborough, Mass.) using standard protocols. Malvern Dispersion Technology Software was used for data acquisition and analysis, applying the general purpose algorithm for calculating size distributions and the Smoluchowski approximation for determining zeta potential.

Example 7

Protein Assays

Whole cells, OMVs and subcellular fractions were assayed for Bla, LacZ and OPH activity using nitrocefin (Sigma), ONPG (Sigma) and paraoxon (Sigma), respectively, according to standard spectrophotometric assays (Cho et al., "Bacterial Cell Surface Display of Organophosphorus Hydrolase for Selective Screening of Improved Hydrolysis of Organophosphate Nerve Agents," *Appl Environ Microbiol* 68:2026-30 (2002); Francisco et al., "Transport and Anchoring of Beta-lactamase to the External Surface of *Escherichia coli*," *Proc Natl Acad Sci USA* 89:2713-7 (1992); and Miller J. H., *A Short Course in Bacterial Genetics. A Laboratory Manual and Handbook for Escherichia coli and Related Bacteria*, Cold Spring Harbor Laboratory Press, Cold Spring Harbor, N.Y. (1992), which are hereby incorporated by reference in their entirety). Cells expressing anti-digoxin scFv were labeled with Dig-BODIPY and analyzed by flow cytometry as described (Daugherty et al., "Development of an Optimized Expression System for the Screening of Antibody Libraries Displayed on the *Escherichia coli* Surface," *Protein Eng* 12:613-21 (1999), which is hereby incorporated by reference in its entirety). Total protein concentration was assayed using the BCA Protein Assay kit (Pierce, Rockford, Ill.). Protease accessibility assays were performed as described but with Proteinase K (Kesty et al., "Incorporation of Heterologous Outer Membrane and Periplasmic Proteins into *Escherichia coli* Outer Membrane Vesicles," *J Biol Chem* 279:2069-76 (2004), which is hereby incorporated by reference in its entirety). Briefly, vesicles were treated at 37° C. for 30 min in 20 mM Tris HCl (pH 8.0) with PK (0.1 mg/ml) in either the absence or presence of 1% SDS. In parallel control experiments, ClyA-GFP and GFP-ClyA that had been purified by IMAC were similarly treated with PK. Following the incubation, all samples were placed on ice and 1 mM PMSF was added to quench all proteolysis, and the samples were analysed by SDS-PAGE. Western blotting was performed as described by Chen et al., "Isolation of High-Affinity Ligand-Binding Proteins by Periplasmic Expression with Cytometric Screening (PECS)," *Nat Biotechnol* 19:537-42 (2001), which is hereby incorporated by reference in its entirety, using the following primary antibodies: anti-ClyA (kindly provided by Sun Nyunt Wai, timed University, Sweden), anti-GFP (Sigma), anti-GroEL (Sigma), anti-polyhistidine (Sigma), anti-OmpA and anti-DsbA (kindly provided by Jon Beckwith, Harvard Medical School). Membranes were developed on film using Immuno-Star™ HRP Substrate Kit (Bio-Rad, Hercules, Calif.).

Example 8

Surface Plasmon Resonance (SPR)

The SPR configuration consisted of a sensor chip, an optical measuring unit, a flow cell and a syringe pump and was similar to that developed previously (Baac et al., "Antibody-Based Surface Plasmon Resonance Detection of Intact Viral Pathogen," *Biotechnol Bioeng* 94:815-9 (2006) and Ferracci et al., "Synaptic Vesicle Chips to Assay Botulinum Neurotoxins," *Biochem J* 391:659-66 (2005), which are hereby incorporated by reference in their entirety). The SPR chip was SF10 glass with a thin layer (50 nm) of gold that was attached to a prism made of SF10 using index matching oil. Two microfluidic channels (reference and test) made of polydimethylsiloxane (PDMS) were placed on the SPR sensor chip and screw-clamped to seal the channels. Single-wavelength light was obtained by passing white light from a Xe-lamp (Oriel, Irvine, Calif.) through a monochromater (Oriel). Light with a bandwidth less than 1 nm passed through the polarizer, where only p-polarized light was transmitted. The reflected light intensity (RI) was measured with a CCD camera (Sony) that showed high sensitivity around 600 nm. When the incident angle of the beam was fixed to 60 degrees, treatment of the sensor chip with PBS resulted in an SPR wavelength of about 600 nm. The SPR wavelength was obtained at each pixel by fitting the RI versus wavelength data to a second-order polynomial equation and the resulting SPR wavelengths, covering a pre-defined region of interest, were averaged. Before each measurement, the RI of s-polarized light was recorded at each pixel for reference. The reliable detection limit of the SPR sensor was measured to be less than 0.2 nm.

Example 9

Vesicle and Vesicle Antigen Detection Using SPR

An SPR chip for detection of vesicles and vesicle-associated antigens was performed as follows. First, an alkanethiol monolayer was self-assembled on the 50-nm gold layer of the sensor chip surface with a mixed solution (1:2 molar ratio) of 10 mM 11-mercaptoundecanoic acid (11-MUA) and 6-mercapto-1-hexanol (6-MCH) as described previously (Choi et al., "Enhanced Performance of a Surface Plasmon Resonance Immunosensor for Detecting Ab-GAD Antibody Based on the Modified Self-Assembled Monolayers," *Biosens Bioelectron* 21:378-83 (2005) and Lee et al., "Characterization of a Self-Assembled Monolayer of Thiol on a Gold Surface and the Fabrication of a Biosensor Chip Based on Surface Plasmon Resonance for Detecting anti-GAD Antibody," *Biosens Bioelectron* 20:1422-7 (2005), which are hereby incorporated by reference in their entirety). The hydroxyl-terminated self-assembled monolayer (SAM), which cannot be activated by N-hydroxysuccinimide (NHS) and N-ethyl-N'-(3-diethylaminopropyl) carbodiimide (EDC), was used as a spacer to construct the sensor surface. Second, following activation of the terminal carboxylic groups of the mixed SAM with a 1:1 mixture of 0.1 M NHS and 0.4 M EDC for 10 min, streptavidin (SA; 200 µg/ml; MP Biomedicals) in 10 mM sodium acetate buffer (pH 5.5) was injected and allowed to covalently couple for 15-20 min followed by PBS rinsing and blocking with 1.0 M ethanolamine hydrochloride (pH 8.5) for 10 min. This resulted in a large increase in the SPR wavelength. Because of the close relationship that exists between electrostatic binding and covalent binding of SA with carboxylic terminated SAMs, this increase in SPR signal is a decent estimate of the extent of covalent binding of SA to the SAMs (Choi et al., "Enhanced Performance of a Surface Plasmon Resonance Immunosensor for Detecting Ab-GAD Antibody Based on the Modified Self-Assembled Monolayers," *Biosens Bioelectron* 21:378-83 (2005), which is hereby incorporated by reference in its entirety). Third, following a thorough PBS wash, biotinylated rabbit anti-*E. coli* antibody (140 µg/ml in PBS; Cortex Biochem) was injected over the SA surface for 20 min and unbound biotinylated anti-*E. coli* antibody was removed by washing with PBS for 10 min. This resulted in an exponential increase in the SPR wavelength that was characteristic of electrostatic binding between SA and biotin-conjugated proteins. As control, bovine serum albumin (BSA; 140 µg/ml in sodium acetate buffer) was added in place of anti-*E. coli* antibody to the SA-coated reference channel of the SPR sensor chip and, as expected, no detectable SPR wavelength shift was observed following introduction of BSA or, subsequently, anti-*E. coli* antibody.

Example 10

Fluorescence Microscopy

For immunofluorescence studies, *E. coli* cells that had been induced to express GFP or ClyA-GFP were washed three times in PBS, incubated at 4° C. overnight with mouse anti-GFP (or anti-polyhistidine) diluted 1:500, pelleted, washed three times with PBS, incubated for 1-hr with rhodamine-labeled goat anti-mouse IgG (Molecular Probes, Carlsbad, Calif.) diluted 1:100, pelleted and washed three more times with PBS. Finally, cells were examined by a Zeiss Axioskop 40 fluorescent microscope with Spotflex color digital camera and filter sets for GFP (485 nm for excitation and 505 nm for emission) and Rhodamine (540 nm for excitation and 600 nm for emission). For fluorescent studies of OMV interactions with eukaryotic cells, HeLa cells grown on glass coverslips were washed in OptiMEM (Life Technologies, Carlsbad, Calif.) without serum and then treated as described herein. Following treatment, cells were fixed with 3.7% formalin in PBS, washed three times in PBS, permeabilized in PBS/0.1% Triton X-100, stained with 0.5 mg/mL ethidium bromide in PBS, and finally washed three times in PBS. Coverslips were mounted onto glass slides using Vectashield Hardset mounting medium (Vector Laboratories, Burlingame, Calif.) prior to wide-field epifluorescence analysis. For WGA studies, non-permeabilized cells were incubated with 1 µg/ml Texas red WGA (Molecular Probes) for 1 h at 4° C. For $G_{M1}$ experiments, ~150 µg of vesicles were preincubated with 10 µg $G_{M1}$ (Sigma) for 30 min at 25° C.

Example 11

Electron Microscopy

Ultrastructural analysis of vesicles was performed by negative staining technique as described previously (Wai et al., "The Release of Outer Membrane Vesicles from the Strains of Enterotoxigenic *Escherichia coli*," *Microbiol Immunol* 39:451-6 (1995), which is hereby incorporated by reference in its entirety). For immunogold labeling, a 10-µL suspension of induced *E. coli* cells was collected, washed and applied to 400-mesh Formvar- and carbon-coated copper grids (Electron Microscopy Sciences, Hatfield, Pa.) and incubated for 1 h with anti-GFP diluted 1:500. Cells were washed with PBS, incubated for 1 h with 25 nm colloidal gold-conjugated goat anti-mouse IgG (Electron Microscopy Sciences) diluted 1:100, washed again, negatively stained with 0.25% phosphotungstic acid (PTA, Electron Microscopy Sciences) with 0.01% BSA in water and viewed using a FEI/Philips Morgagni transmission electron microscope.

Example 12

Cytotoxicity Assay

Vesicles were prepared in PBS and total protein in vesicle fractions was quantified by the Coomassie Plus Assay (Pierce) using BSA protein standards. HeLa cells were grown in clear, flat-bottom tissue culture polystyrene 96-well plates (Costar) at an initial density of 5,000 cells per well in 200 µL of growth medium. After 24 h, the growth medium was removed and replaced with 110 μL of Opti-MEM I® (Invitrogen) serum-free medium and 40 μL of undiluted (1×; ~90-150 μg/ml total protein) or 1:1 diluted (0.5×; ~40-60 μg/ml total protein) OMV samples in PBS. Cells were incubated in the presence of vesicle samples for 4 h; afterwards the OMV-containing medium was removed and replaced with 175 μL of phenol red-free growth medium. Following an additional 48 h of incubation, 35 μL of CellTiter 96® Aqueous One Solution Cell Proliferation Assay reagent (Promega, Madison, Wis.) was added to the wells. This assay uses the tetrazolium compound [3-(4,5-dimethylthiazol-2-yl)-5-(3-carboxymethoxyphenyl)-2-(4-sulfophenyl)-2H-tetrazolium, inner salt; MTS] and the electron coupling reagent phenazine methosulfate. MTS is chemically reduced by cells into formazan whose concentration and optical absorbance at 490 nm provide a measure of metabolically active live cells. Samples were incubated for 1 h and the absorbance was read in a microplate spectrophotometer at 490 nm. Cell viability is reported relative to PBS controls.

Example 13

GFP Co-Localizes in Outer Membrane Vesicles when Fused to ClyA

Figure 1B:
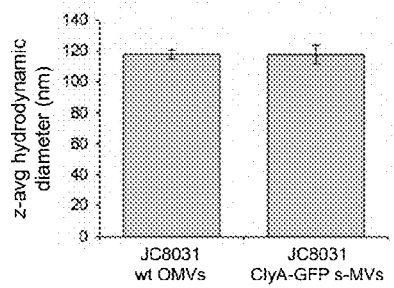
Figure 1C:
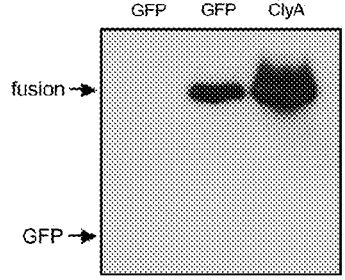
Figure 1D:
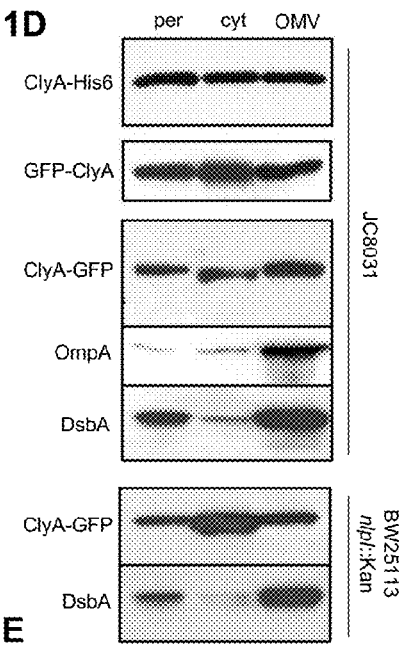
Figure 1E:
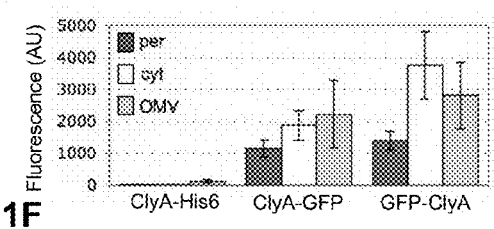
Figure 1F:
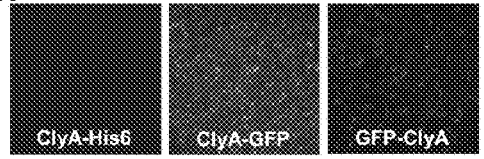

Previous studies demonstrated that genetic fusions between *E. coli* ClyA and reporter proteins such as Bla and GFP were efficiently translocated across the cytoplasmic membrane (del Castillo et al., "Secretion of the *Escherichia coli* K-12 SheA Hemolysin is Independent of its Cytolytic Activity," *FEMS Microbiol Lett* 204:281-5 (2001) and Galen et al., "Adaptation of the Endogenous *Salmonella enterica* serovar *Typhi* ClyA-Encoded Hemolysin for Antigen Export Enhances the Immunogenicity of Anthrax Protective Antigen Domain 4 Expressed by the Attenuated Live-Vector Vaccine Strain CVD 908-htrA," *Infect Immun* 72:7096-106 (2004), which are hereby incorporated by reference in their entirety) and that localization was independent of the position (N- or C-terminus) of ClyA in the fusion protein (del Castillo et al., "Secretion of the *Escherichia coli* K-12 SheA Hemolysin is Independent of its Cytolytic Activity," *FEMS Microbiol Lett* 204:281-5 (2001), which is hereby incorporated by reference in its entirety). Separately, Wai and coworkers demonstrated that ClyA was exported from laboratory strains of *E. coli* cells via OMVs composed of outer membrane and periplasm (Wai et al., "Characterization of dominantly negative mutant ClyA cytotoxin proteins in *Escherichia coli*," *J Bacteriol* 185:5491-9 (2003), which is hereby incorporated by reference in its entirety). These same authors reported that ClyA was significantly enriched in OMVs relative to other lumenal and membrane-bound OMV proteins (Wai et al., "Vesicle-Mediated Export and Assembly of Pore-Forming Oligomers of theEnterobacterial ClyA Cytotoxin," *Cell* 115:25-35 (2003), which is hereby incorporated by reference in its entirety). Based on these results, it was hypothesized that proteins fused to the N- or C-terminus of ClyA would be efficiently co-localized in OMVs and would retain their native function following vesicle localization. To test this, fusion constructs between GFP and the N- or C-terminus of ClyA were generated. Expression of these fusion proteins in the OMV hyper-producing strain JC8031 (Bernadac et al., "*Escherichia coli tol-pal* Mutants Form Outer Membrane Vesicles," *J Bacteriol* 180:4872-8 (1998), which is hereby incorporated by reference in its entirety) followed by purification of vesicles from cell-free culture supernatants yielded uniform s-MVs (FIG. 1A) with an average diameter (FIG. 1B) and zeta-potential that were nearly indistinguishable from naked OMVs produced from plasmid-free JC8031 cells. This result was consistent with earlier findings that vesicle density and size were unaltered due to the incorporation of a heterologous vesicle protein (Kesty et al., "Incorporation of Heterologous Outer Membrane and Periplasmic Proteins into *Escherichia coli* Outer Membrane Vesicles," *J Biol Chem* 279:2069-76 (2004), which is hereby incorporated by reference in its entirety). A significant level of ClyA-GFP or GFP-ClyA was localized in vesicles whereas unfused GFP expressed alone was not detected in the s-MV preparations (FIG. 1C). Consistent with earlier studies of ClyA localization, (Wai et al., "Vesicle-Mediated Export and Assembly of Pore-Forming Oligomers of theEnterobacterial ClyA Cytotoxin," *Cell* 115:25-35 (2003) and Wai et al., "Characterization of Dominantly Negative Mutant ClyA Cytotoxin Proteins in *Escherichia coli*," *J Bacteriol* 185:5491-9 (2003), which are hereby incorporated by reference in their entirety) subcellular fractionation of *E. coli* cells revealed that unfused ClyA accumulated in the cytoplasm, periplasm and OMV fractions (FIG. 1D). Likewise, the addition of GFP as an N- or C-terminal passenger protein resulted in a similar pattern of localization (FIG. 1D), although the amount of ClyA fusions in the insoluble fraction clearly increased compared to unfused ClyA. Both fusion proteins were fluorescent in the cytoplasm, periplasm, and OMV fractions (FIGS. 1E-1F) and the whole cell fluorescence associated with cells expressing ClyA-GFP or GFP-ClyA was nearly as bright as cells expressing GFP alone. Taken together, the data clearly indicate that GFP was compatible with ClyA translocation as chimeras between these two proteins co-localized in OMVs without significant losses in fluorescence activity.

The quality of the fractionation procedure was confirmed by the observation that endogenously expressed outer membrane protein OmpA was always found predominantly in the OMV fraction (shown for cells expressing ClyA-GFP, FIG. 1D), consistent with earlier studies, (Wai et al., "Vesicle-mediated Export and Assembly of Pore-Forming Oligomers of the Enterobacterial ClyA Cytotoxin," *Cell* 115:25-35 (2003), which is hereby incorporated by reference in its entirety) while GroEL was found exclusively in the cytoplasmic fraction and DsbA in the periplasmic fraction (FIG. 1D). DsbA also accumulated to high levels in the OMV fraction (FIG. 1D). While it is common for periplasmic proteins to become entrapped in OMVs, (Horstman et al., "Enterotoxigenic *Escherichia coli* Secretes Active Heat-Labile Enterotoxin Via Outer Membrane Vesicles," *J Biol Chem* 275:12489-96 (2000); McBroom et al., "Outer Membrane Vesicles," In *EcoSal—Escherichia coli and Salmonella: Cellular and Molecular Biology* (III, R. C., ed.). ASM Press, Washington, D.C. (2005); Wai et al., "Vesicle-Mediated Export and Assembly of Pore-Forming Oligomers of theEnterobacterial ClyA Cytotoxin," *Cell* 115:25-35 (2003); and Kesty et al., "Incorporation of Heterologous Outer Membrane and Periplasmic Proteins into *Escherichia coli* Outer Membrane Vesicles," *J Biol Chem* 279:2069-76 (2004), which are hereby incorporated by reference in their entirety) the presence of DsbA was unexpected based on the findings of Wai and coworkers who reported that this protein was excluded from their OMV fractions (Wai et al., "Vesicle-Mediated Export and Assembly of Pore-Forming Oligomers of theEnterobacterial ClyA Cytotoxin," *Cell* 115:25-35 (2003), which is hereby incorporated by reference in its entirety). One explanation for this discrepancy might have been related to the use of the tolRA mutant strain JC8031, which despite its tendency to secrete copious amounts of vesicles is also characterized by a leaky outer membrane (Bernadac et al., "*Escherichia coli* tol-pal Mutants Form Outer Membrane Vesicles," *J Bacteriol* 180:4872-8 (1998) and McBroom et al., "Outer Membrane Vesicle Production by *Escherichia coli* is Independent of Membrane Instability," *J Bacteriol* 188:5385-92 (2006), which are hereby incorporated by reference in their entirety). However, similar patterns of ClyA-GFP and DsbA localization were observed following subcellular fractionation of ΔnlpI mutant cells (FIG. 1D) that are known to produce relatively large quantities of vesicles but do not exhibit membrane instability (McBroom et al., "Outer Membrane Vesicle Production by *Escherichia coli* is Independent of Membrane Instability," *J Bacteriol* 188:5385-92 (2006), which is hereby incorporated by reference in its entirety). Thus, the explanation that is currently favored, based on earlier observations, (Horstman et al., "Enterotoxigenic *Escherichia coli* Secretes Active Heat-Labile Enterotoxin Via Outer Membrane Vesicles," *J Biol Chem* 275:12489-96 (2000), which is hereby incorporated by reference in its entirety) is that the use of a different host strain resulted in altered vesicle protein profiles.

Figure 2A:
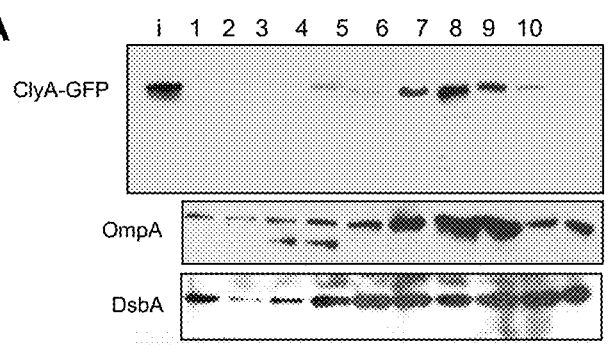
FIGS. 2A-2C show the density gradient fractionation of vesicles.
Figure 2B:
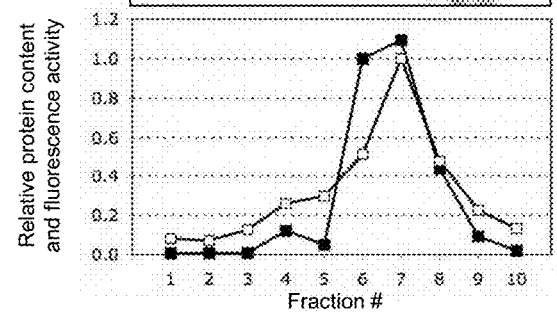
Figure 2C:
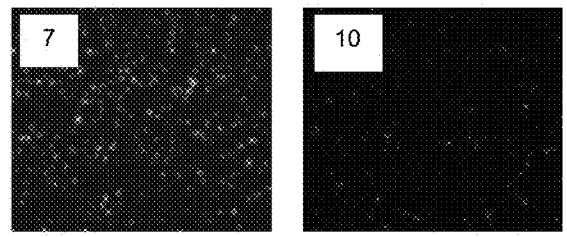

To determine whether ClyA-GFP in the pelleted supernatant was associated with intact vesicles or with released outer membrane fragments, fusion protein co-migration with both periplasmic and outer membrane material was tested. To this end, pelleted supernatant from cells expressing ClyA-GFP was separated by density gradient centrifugation. Western blotting and densitometry analysis of the resulting fractions revealed a gradient profile for ClyA-GFP that peaked in fractions 6-8 (FIG. 2A and FIG. 2B), reminiscent of the gradient profile of OMV-associated α-hemolysin (Balsalobre et al., "Release of the Type I Secreted alpha-Haemolysin Via Outer Membrane Vesicles from *Escherichia coli,*" *Mol Microbiol* 59:99-112 (2006), which is hereby incorporated by reference in its entirety). As expected, the maximal GFP activity was detected in the same fractions that contained the ClyA-GFP-enriched OMVs (FIG. 2B and FIG. 2C) although weaker fluorescence could be detected in denser fractions (FIG. 2C). The outer membrane protein OmpA was similarly enriched in fractions 6-8 containing the majority of the ClyA-GFP, but strong bands also appeared in fractions 9 and 10 (FIG. 2A). Interestingly, DsbA was more evenly distributed between fractions 5-10 (FIG. 2A), indicating co-migration with vesicles that included a large portion of ClyA-GFP (fractions 6-8) as well as with vesicles that contained lesser amounts of ClyA-GFP (fractions 5, 9 and 10).

Example 14

ClyA Anchors Correctly Folded GFP to the Outer Surface of *E. coli* and to the Surface of s-MVs To determine the topology of the ClyA-GFP and GFP-ClyA chimeras, the surface accessibility of GFP on whole cells and on vesicles was probed. Previous studies showed that a fraction of the secreted ClyA remains located on the bacterial cell surface (Wai et al., "Vesicle-Mediated Export and Assembly of Pore-Forming Oligomers of theEnterobacterial ClyA Cytotoxin," *Cell* 115:25-35 (2003), which is hereby incorporated by reference in its entirety). Likewise, it was observed that both ClyA-GFP and GFP-ClyA were localized to the cell surface as evidenced by the accessibility of the GFP moiety to cross-reacting antibodies. Specifically, positive immunofluorescent- and immunogold-labeling using anti-GFP antibodies was detected for JC8031 cells expressing ClyA fused with GFP but not in the cases of unfused ClyA or unfused GFP (FIG. 3, shown for unfused GFP and ClyA-GFP).

Figure 4A:
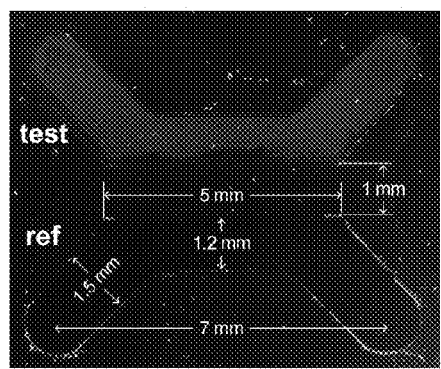
FIGS. 4A-4D depicts the detection of vesicles and vesicle-associated antigens via immuno-Surface Plasmon Resonance (SPR).
Figure 4B:
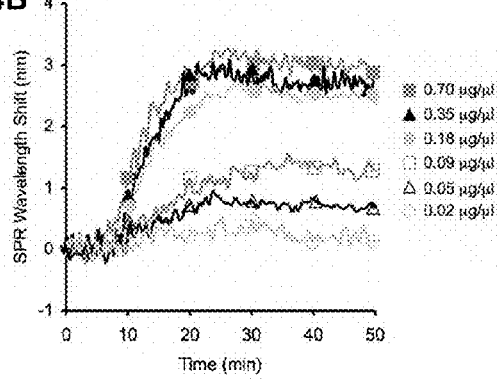
Figure 4C:
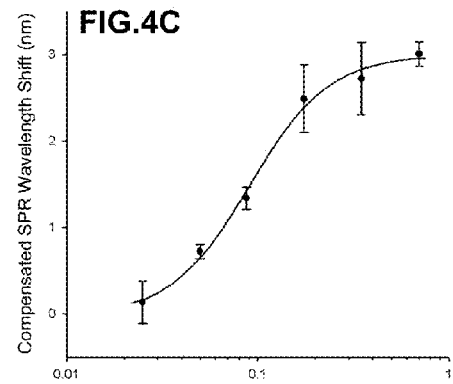
Figure 4D:
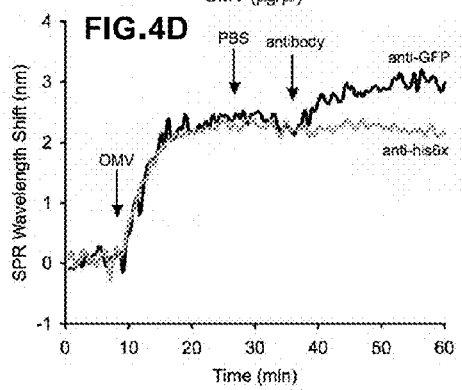

To determine if the GFP associated with vesicles was similarly accessible to cross-reacting antibodies, immunofluorescent labeling of s-MVs was performed but only a weak immunofluorescent signal above background could be seen in this analysis. This prompted the exploration of a more sensitive and quantitative surface plasmon resonance (SPR)-based strategy for detecting vesicle-associated GFP. For this, biotinylated anti-*E. coli* antibodies (test channel) and bovine serum albumin (BSA, reference channel) were coupled to an SPR sensor chip through streptavidin binding. To verify that the SPR surface could capture the s-MVs, solutions containing varying amounts of intact s-MVs from fraction 7 above were introduced, where the initial concentration of s-MVs in this fraction was 13.5±1.34 μg/μl. Following introduction of ClyA-GFP-containing s-MVs to the SPR, it was immediately noticed that the test channel coated with anti-*E. coli* antibodies but not the BSA-coated reference channel was highly fluorescent (FIG. 4A), even after several PBS wash steps, indicating specific capture of the s-MVs on the SPR surface. SPR binding revealed concentration-dependent shifts in the SPR wavelength over a range of s-MV concentrations (0.02-0.70 μg/μl) (FIG. 4B and FIG. 4C). Importantly, there was no measurable change in SPR wavelength upon treatment of surface-captured s-MVs with PBS, indicating that the fluorescent vesicles were stably and tightly bound to the immobilized anti-*E. coli* antibody. Finally, to determine whether the SPR strategy was suitable for detecting OMV-associated antigens, anti-GFP monoclonal antibodies were introduced into the test channel that contained surface-captured s-MVs displaying active GFP. Specific binding between anti-GFP antibodies and vesicle-associated GFP was confirmed by a marked increase in the SPR wavelength in the test channel (FIG. 4D, black line). Controls were performed where these s-MVs were treated with non-specific anti-His6× monoclonal antibodies or where s-MVs displaying unfused ClyA were captured on the SPR surface and treated with anti-GFP antibodies; both cases resulted in no detectable increase in the SPR wavelength (shown for anti-His6× treatment of Cly-GFP s-MVs in FIG. 4D, gray line).

Figure 5A:
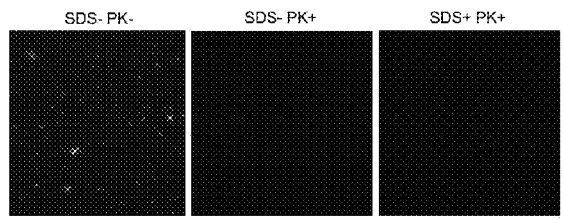
FIGS. 5A-5D illustrate the biochemical and genetic analysis of ClyA localization. Proteinase K susceptibility of OMV-tethered GFP was determined by fluorescence microscopy of vesicles generated from JC8031 cells expressing ClyA-GFP treated with Proteinase K and SDS as indicated (FIG. 5A) and Western blot of vesicles generated from JC8031 cells expressing ClyA-GFP or GFP-ClyA (FIG. 5B). Blots were probed with mouse anti-GFP (left panels) or anti-ClyA serum (right panels). The molecular weight (MW) ladder is marked at left. An equivalent number of vesicles was used in all cases.
Figure 5B:
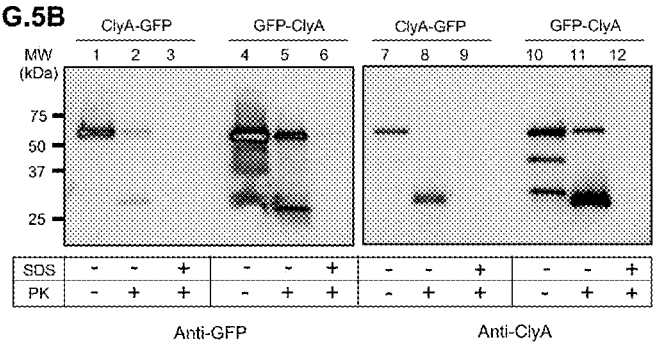

Proteinase K (PK) susceptibility assays on ClyA-GFP and GFP-ClyA vesicles were performed to determine whether the immuno-accessible GFP was protected by the vesicle structure. When s-MVs derived from JC8031 cells expressing ClyA-GFP or GFP-ClyA were incubated with PK in the absence of membrane-disrupting detergent, vesicle-associated fluorescence was completely abolished (FIG. 5A, shown for ClyA-GFP) suggesting that the majority of the functional GFP was surface exposed and not protected by the vesicle structure. Consistent with this, Western blot analysis confirmed that nearly all of the s-MV-associated ClyA-GFP was degraded to a lower molecular weight anti-GFP or anti-ClyA cross-reacting species upon treatment with PK (FIG. 5B, lanes 1-3 and 7-9). Interestingly, a significant amount of PK-resistant material was observed following identical treatment of GFP-ClyA s-MVs (FIG. 5B, lanes 4-6 and 10-12) that persisted even after incubation with 2-5× higher PK concentrations for 2× longer durations. Since these PK-treated s-MVs were non-fluorescent but contained a considerable portion of PK-resistant GFP-ClyA, it was concluded that only a fraction of the fusion localizes with functional GFP tethered outside the OMV while the remainder adopts an inactive conformation that is protected by the vesicle structure. Possible reasons for this include a localization defect caused by the relatively high level of expression for GFP-ClyA compared to ClyA-GFP and/or the apparent instability of the fusion as evidenced by the multiple anti-ClyA cross-reacting bands seen in the absence of PK (FIG. 5B, lane 10). For both chimeras, complete proteolytic digestion of GFP by PK occurred when membranes were disrupted by the addition of 1% SDS (FIG. 5B). Control experiments using purified, soluble ClyA-GFP showed that the protein was PK-sensitive both in the presence or absence of the detergent.

Example 15

Figure 5C:
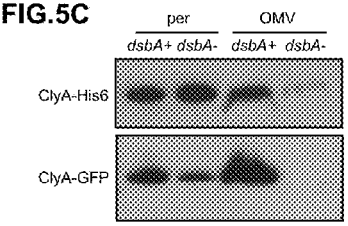
Figure 5D:
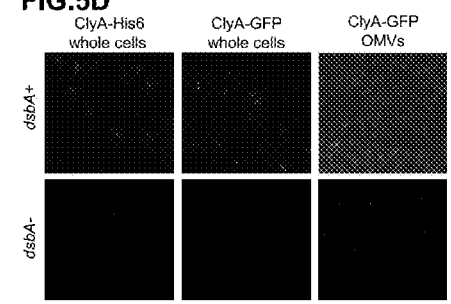

Periplasmic Disulfide Bond-Forming Machinery is Required for Localization of ClyA and ClyA Fusions in OMVs In previous work, ClyA in the periplasm was shown to adopt a monomeric conformation owing to an intramolecular disulfide bond formed between the cysteine residues at positions 87 and 285 in the polypeptide (Atkins et al., "Structure-function relationships of a novel bacterial toxin, hemolysin E. The role of alpha G,"*J Biol Chem* 275:41150-5 (2000), which is hereby incorporated by reference in its entirety). The presence of the disulfide bond was sufficient to prevent oligomerization of ClyA and inactivate its native haemolytic activity. In agreement with this finding, Wai et al. reported that DsbA, the enzyme responsible for catalyzing the formation of disulfide bonds in periplasmic proteins, was absent from OMVs containing ClyA and that the absence of DsbA was necessary for ClyA to oligomerize into its haemolytic conformation (Wai et al., "Vesicle-Mediated Export and Assembly of Pore-Forming Oligomers of theEnterobacterial ClyA Cytotoxin," *Cell* 115:25-35 (2003), which is hereby incorporated by reference in its entirety). Contrary to the findings of Wai et al., DsbA was co-localized in vesicles containing the ClyA fusions in these studies (see FIG. 1 above). Thus, it was hypothesized that oxidized, monomeric ClyA might be favorable for efficient cell surface and vesicle localization of fusion proteins. To test this hypothesis, expression of ClyA-GFP in strain JC8031 and an isogenic dsbA::Kan mutant derived from JC8031 was compared. Western blot analysis revealed that while both strains accumulated similar amounts of ClyA-GFP in the periplasm, only in cells with DsbA present was localization of ClyA-GFP observed (FIG. 5C). This was corroborated by a complete lack of fluorescence seen for OMVs derived from JC8031 dsbA::Kan cells expressing ClyA-GFP (FIG. 5D). Immunofluorescent staining of these same cells revealed that localization of ClyA-GFP to the bacterial cell surface was also dependent upon DsbA (FIG. 5D). It was surprising to find that, DsbA-dependent vesicle localization was also observed for unfused ClyA suggesting that the periplasmic redox state is a critical factor in regulating the efficiency of protein localization into vesicles under the conditions tested here. Interestingly, very little, to no, apparent cytotoxicity for naked OMVs from plasmid-free JC8031 cells was observed, consistent with earlier studies, (Wai et al., "Vesicle-Mediated Export and Assembly of Pore-Forming Oligomers of theEnterobacterial ClyA Cytotoxin," *Cell* 115: 25-35 (2003), which is hereby incorporated by reference in its entirety) and also for s-MVs containing ClyA-His6, ClyA-GFP or GFP-ClyA suggesting that ClyA in these vesicles was not in its haemolytically-active, oligomeric conformation.

Example 16

Engineered ClyA-GFP s-MVs are Useful for Visualizing Vesicle Interactions with Eukaryotic Cells Previous studies have shown that vesicles derived from pathogenic *E. coli* or non-pathogenic *E. coli* strains can associate with eukaryotic cells (Kesty et al., "Enterotoxigenic *Escherichia coli* Vesicles Target Toxin Delivery into Mammalian Cells," *EMBO J* 23:4538-49 (2004) and Kesty et al., "Incorporation of Heterologous Outer Membrane and Periplasmic Proteins into *Escherichia coli* Outer Membrane Vesicles," *J Biol Chem* 279:2069-76 (2004), which are hereby incorporated by reference in their entirety). Thus, whether s-MVs functionalized with ClyA-GFP were suitable for tracking vesicle association with eukaryotic cells was investigated. Previous attempts at this focused on loading GFP into the lumen of vesicles following its transport into the periplasm by the twin-arginine translocation (Tat) pathway (Kesty et al., "Incorporation of Heterologous Outer Membrane and Periplasmic Proteins into *Escherichia coli* Outer Membrane Vesicles," *J Biol Chem* 279:2069-76 (2004), which is hereby incorporated by reference in its entirety). However, GFP-containing OMVs were only weakly fluorescent and could not be tracked in host cells by microscopy, likely due to the low yield of GFP transport to the periplasm via the Tat system. To determine if s-MVs engineered with ClyA-GFP were bright enough for tracking studies, vesicle-host cell co-incubation assays were performed. Punctate green staining was observed following a 30 min incubation of HeLa cells with ~150 µg vesicles purified ClyA-GFP s-MVs and the intensity of this staining increased as the incubation time between HeLa cells and ClyA-GFP s-MVs increased (FIG. 6A). These results imply that vesicles persisted on the cell surface or had fused directly to the target cell membrane. To corroborate this, HeLa cells that had been incubated with purified ClyA-GFP-containing s-MVs were stained with a fluorescent version of the cell surface marker wheat germ agglutinin (WGA) and then washed with PBS. Confocal microscopy revealed that ClyA-GFP OMVs co-localized with WGA on the exterior of the cell. Next, the fate of ClyA-GFP vesicles was explored by examining whether the appearance of punctate fluorescence was temperature dependent, a hallmark of cellular internalization (Kesty et al., "Enterotoxigenic *Escherichia coli* Vesicles Target Toxin Delivery into Mammalian Cells," *EMBO J* 23:4538-49 (2004) and Pelkmans et al., "Caveolar Endocytosis of Simian Virus 40 Reveals a New Two-Step Vesicular-Transport Pathway to the ER," *Nat Cell Biol* 3:473-83 (2001), which are hereby incorporated by reference in their entirety). HeLa cells incubated with vesicles containing ClyA-GFP at 4° C. exhibited very low levels of cell-associated fluorescence (compare FIG. 6B). However, when HeLa cells were incubated with ClyA-GFP s-MVs at 4° C. for 3 h and then shifted to 37° C. for 3 hr, strong cell fluorescence was observed (FIG. 6B), leaving open the possibility that some s-MVs may be internalized at 37° C. A key factor in endocytosis is ganglioside M1 ($G_{M1}$), which is a eukaryotic cell surface receptor for enterotoxins such as LT and cholera toxin (CT) and is required for endocytosis of LT-containing OMVs derived from non-pathogenic *E. coli* (Kesty et al., "Enterotoxigenic *Escherichia coli* Vesicles Target Toxin Delivery into Mammalian Cells," *EMBO J* 23:4538-49 (2004), which is hereby incorporated by reference in its entirety). Therefore, whether the observed fluorescence of HeLa cells incubated with ClyA-GFP s-MVs was $G_{M1}$-dependent was tested. Indeed, fluorescence associated with HeLa cells was significantly decreased following incubation with purified ClyA-GFP s-MVs that had been not been pretreated with $G_{M1}$ (FIG. 6C). Moreover, incubation with $G_{M1}$-treated vesicles resulted in a small number of large fluorescent clusters and much less punctate green fluorescence than was observed for HeLa cells incubated with untreated ClyA-GFP OMVs (FIG. 6C). Thus, it appears that $G_{M1}$ cell surface receptors may play an important role in mediating interactions between HeLa cells and engineered vesicles. Finally, to assay the cytotoxic effect of vesicles on target cells, an analysis of how cultured HeLa cells were affected by equivalent amounts of different vesicle preparations was performed. In general, vesicles containing ClyA-His6 or ClyA-GFP exhibited virtually no detectable cytotoxicity (FIG. 6D), consistent with a monomoric, DsbA+ conformation (Wai et al., "Vesicle-Mediated Export and Assembly of Pore-Forming Oligomers of theEnterobacterial ClyA Cytotoxin," *Cell* 115:25-35 (2003), which is hereby incorporated by reference in its entirety) for both ClyA and ClyA-GFP in these vesicles.

Example 17

Heterologous Proteins Co-Localized in s-MVs Via ClyA Retain their Activity

To determine whether proteins other than GFP could be fused to ClyA while still retaining their function, a series of N- and C-terminal fusions between ClyA and the following enzymes: β-lactamase (Bla), organophosphorus hydrolase (OPH) and β-galactosidase (LacZ), were produced. Similar to what was seen for GFP, ClyA-Bla resulted in localization of Bla to the surface of JC8031 cells and vesicles as determined using a nitrocefin hydrolysis assay (Table 2).

TABLE 2

ClyA-mediated display of enzymatically active proteins

| Construct | Cell surface activity | OMV activity |
| --- | --- | --- |
| β-lactamase (Bla) | [ΔA486/min] | [ΔA486/min] |
| pBAD18-Kan | 0.03 | 0.02 |
| pΔss-Bla | 0.47 | 0.98 |
| pClyA-Bla | 8.53 | 7.05 |
| pBla-ClyA | 1.43 | 1.65 |
| Organophosphorus hydrolase (OPH) | [U * 1000/ $OD_{600}$] | [U * 1000/g total protein] |
| pBAD24 | 0.09 | 0.04 |
| pOPH | 0.36 | 1.63 |
| pClyA-OPH | 11.62 | 81.63 |
| pOPH-ClyA | 0.22 | 8.19 |
| β-galactosidase (LacZ) | [ΔA420/min] | [ΔA420/min] |
| pBAD24 | 0.02 | 0.02 |
| pLacZ | 0.02 (7.21)† | 0.03 |
| pClyA-LacZ | 0.04 (8.33)† | 0.03 |

†Values in parentheses represent activity in the cytoplasmic fraction.
All values represent the average of 3 replicate experiments where the standard error was <5%.

Since Bla expressed in the cytoplasm was not localized to the cell surface or vesicles and since nitrocefin is relatively impermeable to the outer membrane, (Angus et al., "Outer Membrane Permeability in *Pseudomonas aeruginosa*: Comparison of a Wild-type with an Antibiotic-Supersusceptible Mutant," *Antimicrob Agents Chemother* 21:299-309 (1982) and Good et al., "Antisense PNA Effects in *Escherichia coli* are Limited by the Outer-Membrane LPS Layer" *Microbiology* 146:2665-70 (2000), which are hereby incorporated by reference in their entirety) these data provide strong evidence that the Bla moiety was externally localized on cells and vesicles. Similar results were obtained using the Bla substrate penicillin-G, which also penetrates the outer membrane very poorly (Nikaido et al., "Sensitivity of *Escherichia coli* to Various Beta-lactams is Determined by the Interplay of Outer Membrane Permeability and Degradation by Periplasmic beta-lactamases: A Quantitative Predictive Treatment," *Mol Microbiol* 1:29-36 (1987), which is hereby incorporated by reference in its entirety). Interestingly, as was seen above for the chimeras between ClyA and GFP, fusion of Bla to the N-terminus of ClyA resulted in a significantly lower level of Bla activity. Consistent with these results, fusion of ClyA to the N-terminus of the OPH enzyme conferred a significant level of OPH activity to the surface of cells and vesicles, whereas OPH-ClyA resulted in no measurable surface-associated OPH activity (Table 2). Since the OPH substrate paraoxon used in these experiments is membrane impermeable, (Richins et al., "Biodegradation of Organophosphorus Pesticides by Surface-Expressed Organophosphorus Hydrolase," *Nat Biotechnol* 15:984-7 (1997), which is hereby incorporated by reference in its entirety) it was concluded that ClyA-OPH is oriented with OPH externally bound to both cells and vesicles. Also, since OPH activity depends upon homodimer formation, (Grimsley et al., "Organophosphorus Hydrolase is a Remarkably Stable Enzyme that Unfolds Through a Homodimeric Intermediate," *Biochemistry* 36:14366-74 (1997), which is hereby incorporated by reference in its entirety) ClyA apparently tethers OPH in a conformation that allows for dimerization with a neighboring ClyA-OPH molecule. Finally, to determine if the ability to display multimeric enzymes is a general feature of ClyA-mediated surface exposure, ClyA fusions to the homotetrameric LacZ enzyme from *E. coli* were constructed (Jacobson et al., "Three-Dimensional Structure of Beta-galactosidase from *E. coli*," *Nature* 369:761-6 (1994), which is hereby incorporated by reference in its entirety). While expression of ClyA-LacZ resulted in strong cytoplasmic LacZ activity, there was no measurable LacZ activity on the surface of cells or their derived s-MVs (Table 2). In fact, there was no LacZ activity in the periplasm of cells expressing ClyA-LacZ), consistent with the observation that the normally cytoplasmic LacZ protein contains sequences that hinder transport (Lee et al., "Genetic Studies on the Inability of Beta-galactosidase to be Translocated Across the *Escherichia coli* Cytoplasmic Membrane," *J Bacteriol* 171:4609-16 (1989), which is hereby incorporated by reference in its entirety) usually leading to a misfolded, and thus inactive, protein.

Figure 7A:
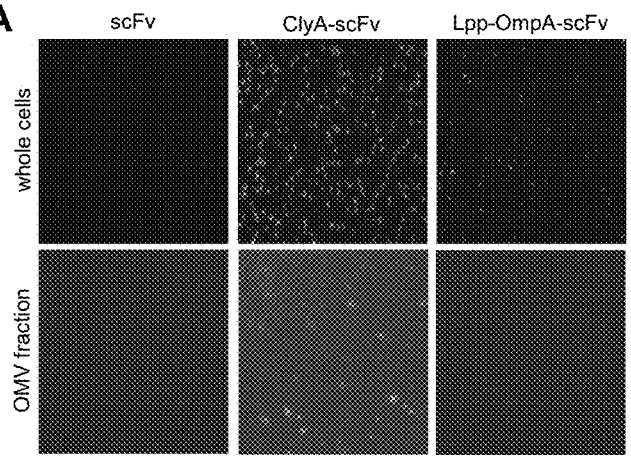
FIGS. 7A-7B show the creation of immuno-MVs via ClyA-scFv chimeras.

Single-chain antibody fragments (scFv) have been successfully used to create artificial immunoliposomes for targeting of these vesicles and their payloads to specific cell types (Kontermann, R. E., "Immunoliposomes for Cancer Therapy," *Curr Opin Mol Ther* 8:39-45 (2006), which is hereby incorporated by reference in its entirety). Along similar lines, it was desirable to create bacterial "immuno-MVs" by displaying scFv fragments on *E. coli*-derived vesicles. For these experiments, an scFv derived from the 26-10 monoclonal antibody that binds with high affinity ($K_D$=0.9±0.2× 10-9 $M^{-1}$) to the cardiac glycoside digoxin (scFv.Dig) was used (Daugherty et al., "Quantitative Analysis of the Effect of the Mutation Frequency on the Affinity Maturation of Single Chain Fv antibodies," *Proc Natl Acad Sci USA* 97:2029-34 (2000) and Francisco et al., "Production and Fluorescence-Activated Cell Sorting of *Escherichia coli* Expressing a Functional Antibody Fragment on the External Surface," *Proc Natl Acad Sci USA* 90:10444-8 (1993), which are hereby incorporated by reference in their entirety). Using a fluorescent conjugate of digoxin (Dig-BODIPY), expression of ClyA-scFv.Dig, but not scFv.Dig alone, resulted in cells and vesicles that were able to bind the fluorescent probe (FIG. 7A). Since Dig-BODIPY cannot permeate the outer membrane under standard conditions, (Chen et al., "Isolation of High-Affinity Ligand-Binding Proteins by Periplasmic Expression with Cytometric Screening (PECS)," *Nat Biotechnol* 19:537-42 (2001), which is hereby incorporated by reference in its entirety) the detection of Dig-BODIPY binding activity using intact cells indicates that scFvs were functionally displayed on the outer cell and vesicle surface. For comparison, cells expressing scFv.Dig fused to the well-characterized Lpp-OmpA hybrid OM anchor (Francisco et al., "Production and Fluorescence-Activated Cell Sorting of *Escherichia coli* Expressing a Functional Antibody Fragment on the External Surface," *Proc Natl Acad Sci USA* 90:10444-8 (1993), which is hereby incorporated by reference in its entirety) displayed uniform but notably weaker cell surface fluorescence and no detectable fluorescence on OMVs (FIG. 7A) despite the fact that wildtype OmpA localizes in OMVs (Wai et al., "Vesicle-Mediated Export and Assembly of Pore-Forming Oligomers of the Enterobacterial ClyA Cytotoxin," *Cell* 115:25-35 (2003), which is hereby incorporated by reference in its entirety) (see also FIG. 1D above).

Figure 7B:
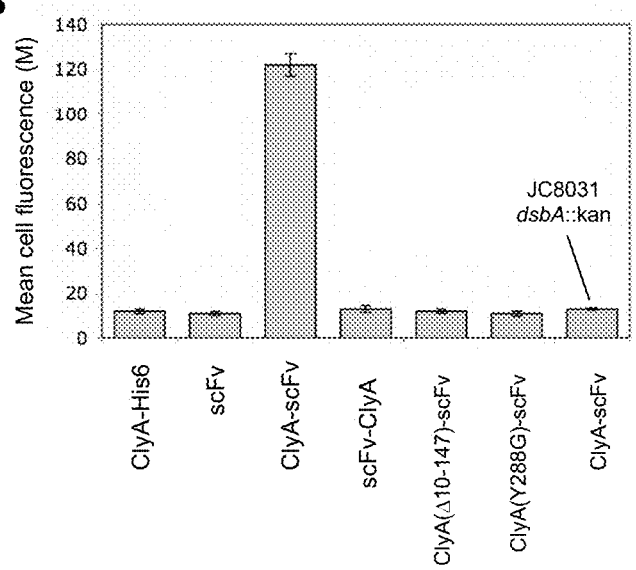

Lastly, it was determine whether the capture of Dig-BODIPY by ClyA-scFv.Dig could be used as a genetic screen for ClyA localization. Consistent with the fluorescence microscopy results above, labeling of JC8031 cells expressing ClyA-scFv.Dig with Dig-BODIPY resulted in highly fluorescent cells as revealed by flow cytometry (FIG. 7B). However, when ClyA-scFv.Dig was expressed in JC8031 dsbA::Kan cells, fluorescence was completely abolished. Likewise, when scFv.Dig was expressed alone, as an N-terminal fusion to ClyA (scFv.Dig-ClyA), or as a C-terminal fusion to ClyA variants carrying mutations that were previously reported to disrupt translocation (e.g., deletion of 10-147 of the last C-terminal amino acids (Wai et al., "Characterization of Dominantly Negative Mutant ClyA Cytotoxin Proteins in *Escherichia coli,*" *J Bacteriol* 185:5491-9 (2003), which is hereby incorporated by reference in its entirety) or substitution of the Tyr288 residue with Gly (del Castillo et al., "Secretion of the *Escherichia coli* K-12 SheA Hemolysin is Independent of its Cytolytic Activity," *FEMS Microbiol Lett* 204: 281-5 (2001), which is hereby incorporated by reference in its entirety)), no measurable cell fluorescence was detected (FIG. 7B).

Discussion of Examples 1-17

This work describes the development and characterization of engineered synthetic membrane vesicles (s-MVs) created by genetic fusion of a recombinant polypeptide with the *E. coli* cytotoxin ClyA. In general, it was observed that most recombinant polypeptide fusions co-localized with ClyA to the bacterial cell surface and into OMVs. Specifically, it was demonstrated that direct fusion of Bla, OPH, GFP and anti-digoxin scFv to the C-terminus of ClyA resulted in functional display of each protein on the surface of *E. coli* cells and their derived OMVs, giving rise to s-MVs with significantly expanded, non-native functionality (e.g., fluorescence, antigen binding). Interestingly, fusion of each of these proteins to the N-terminus of ClyA yielded unpredictable results. For instance, scFv.Dig-ClyA exhibited no detectable activity on the surface of cells or OMVs while GFP-ClyA resulted in the display of active protein. In the latter case, even though a portion of the fusions was active, a significant amount of non-fluorescent GFP-ClyA accumulated in OMVs. It was also found that fusion of the enzymes Bla and OPH resulted in little to no activity on cells and OMVs when each enzyme was fused to the N-terminus of ClyA. These results are consistent with earlier studies where a 2-fold increase in secretion to the extracellular medium was observed for ClyA-Bla versus Bla-ClyA (del Castillo et al., "Secretion of the *Escherichia coli* K-12 SheA Hemolysin is Independent of its Cytolytic Activity," *FEMS Microbiol Lett* 204:281-5 (2001), which is hereby incorporated by reference in its entirety). At present, it is not known why N-terminal fusions to ClyA were inconsistent whereas C-terminal fusions invariably yielded well-displayed proteins that retain their biological function. These results might be explained by inspection of the medium-resolution structure of membrane-bound ClyA showing that the C-terminus of ClyA is embedded deeper within membranes (i.e., closer to the outer surface) than the N-terminal portion, which occurs close to the periplasmic side of the outer membrane (Eifler et al., "Cytotoxin ClyA from *Escherichia coli* Assembles to a 13-meric Pore Independent of its Redox-State," *EMBO J* 25:2652-61 (2006) and Tzokov et al., "Structure of the hemolysin E (HlyE, ClyA, SheA) channel in its membrane-bound form," *J Biol Chem* 281:23042-9 (2006), which is hereby incorporated by reference in its entirety). According to this model, fusions to the C-terminus of ClyA are closer to the outer surface and more likely to extend into the extracellular environment, especially with the addition of a flexible 5-residue Gly linker that was included in all of fusions.

Based on its relative plasticity as a fusion partner, ClyA can serve as a useful tethering module for: (1) dissecting the complete ClyA translocation pathway from bacteria to target host cells; and (2) biotechnological applications that rely on cell or OMV surface display, such as affinity maturation of antibody fragments and vaccine adjuvant development (Daugherty et al., "Quantitative Analysis of the Effect of the Mutation Frequency on the Affinity Maturation of Single Chain Fv Antibodies," *Proc Natl Acad Sci USA* 97:2029-34 (2000); Francisco et al., "Production and Fluorescence-Activated Cell Sorting of *Escherichia coli* Expressing a Functional Antibody Fragment on the External Surface," *Proc Natl Acad Sci USA* 90:10444-8 (1993); Chen et al., "Cell-Surface Display of Heterologous Proteins: From High-Throughput Screening to Environmental Applications," *Biotechnol Bioeng* 79:496-503 (2002); and Georgiou et al., "Display of Heterologous Proteins on the Surface of Microorganisms: From the Screening of Combinatorial Libraries to Live Recombinant Vaccines," *Nat Biotechnol* 15:29-34 (1997), which are hereby incorporated by reference in their entirety). For instance, with respect to genetic analysis, expression of ClyA-GFP and ClyA-scFv.Dig both proved capable of reporting the localization of ClyA to the bacterial cell surface and into OMVs and revealed an essential role for DsbA in the translocation process. A simple model for ClyA assembly in vesicles proposed by Uhlin and coworkers, and supported by these findings, is that ClyA oligomerization and membrane insertion is governed by the redox state of ClyA (Wai et al., "Vesicle-Mediated Export and Assembly of Pore-Forming Oligomers of the Enterobacterial ClyA Cytotoxin," *Cell* 115: 25-35 (2003), which is hereby incorporated by reference in its entirety). Here, however, it was shown that a more reducing environment in the periplasm, such as occurs when DsbA is absent, favors the localization of ClyA and ClyA fusions into vesicles. While the involvement of DsbA appears to be via direct oxidation of ClyA, (Wai et al., "Vesicle-Mediated Export and Assembly of Pore-Forming Oligomers of the Enterobacterial ClyA Cytotoxin," *Cell* 115:25-35 (2003), which is hereby incorporated by reference in its entirety) the possibility that DsbA is responsible for the oxidation of a periplasmic or membrane component(s) that mediate the localization of ClyA and/or the formation of OMVs cannot be ruled out.

With respect to biotechnology, the ability of ClyA to anchor and functionally display a variety of different prokaryotic and eukaryotic proteins on the surface of bacterial cells and vesicles should be useful for numerous applications. First, ClyA exhibits properties that make it an ideal carrier protein for bacterial cell surface display of peptides and proteins and compares favorably with the well-established Lpp-OmpA surface anchor as evidenced by scFv binding of fluorescently tagged digoxin. Second, by judicious selection and display of specific scFv fragments on OMVs, one might be able to redirect these engineered "immuno-MVs" to specific cell types, or otherwise engineer the host-vesicle interaction, in order to achieve a desired therapeutic or immunological response. Along these lines, these data provide encouraging data that engineered vesicles retain their characteristic interactions with mammalian cells (Kesty et al., "Enterotoxigenic *Escherichia coli* Vesicles Target Toxin Delivery into Mammalian Cells,". *EMBO J* 23:4538-49 (2004) and Kesty et al., "Incorporation of Heterologous Outer Membrane and Periplasmic Proteins into *Escherichia coli* Outer Membrane Vesicles," *J Biol Chem* 279:2069-76 (2004), which is hereby incorporated by reference in its entirety) and are almost completely non-cytotoxic. It is also noteworthy that expression of all ClyA fusions in this study had no measurable effect on the growth rate of bacterial cells relative to cells expressing unfused ClyA or empty vector controls, thus appreciable yields of cells or their derived OMVs should be attainable for any OMV-based application.

Example 18

Plasmid Construction

Plasmids for ClyA, GFP, and ClyA-GFP were constructed with C-terminal 6×-histidine tags to facilitate purification of the protein products. The plasmids pClyA-His6, encoding the *E. coli* gene clyA fused to the 5' end of a 6×-histidine tag, and pClyA-GFP, encoding clyA fused to the 5' end of gfp-mut2 (26) are described supra in Example 1. To construct pClyA-GFP-His6, a ~1.7 kb fragment was amplified by polymerase chain reaction (PCR) with plasmid pClyA-GFP as template using primers (5'-TCGCAACTCTCTACTGTTTC-3') (SEQ ID NO:13) and (5'-GCGATGAAG CTTTTAATGGTGATG-GTGATGATGTTTGTATAGTTCATCCATGCC-3') (SEQ ID NO:14). The resulting product was cloned in the XbaI and HindIII sites of pBAD18-Cm (Guzman et al., "Tight Regulation, Modulation, and High-Level Expression by Vectors Containing the Arabinose P-Bad Promoter," *J Bacteriol* 177: 4121-4130 (1995), which is hereby incorporated by reference in its entirety). For construction of pGFP-His6, a ~700 bp fragment was amplified by PCR with plasmid pClyA-GFP as template and using primers (5'-GCGATGGAATTC-GAGCTCTTAAAGAGGAGAAAGGTCAT-GAGTAAAGGA GAAGAACTTTT-3') (SEQ ID NO:15) and (5'-GCGATGAAGCTTTTAATGGTGATGGT-GATGATGTTT GTATAGTTCATCCATGCC-3') (SEQ ID NO:16). The amplification product was cloned into pBAD18-Cm using the SacI and HindIII restriction sites. DNA constructs were verified by automated dideoxy chain-termination sequencing. Plasmids were transformed into *E. coli* DH5α and selected in LB medium containing chloramphenicol.

Example 19

Recombinant Protein Purification

Cultures of *E. coli* DH5α were grown in 100 mL of LB medium containing chloramphenicol. Protein expression was induced by addition of L-arabinose to a final concentration of 0.2% once the $OD_{600}$ reached approximately 0.5. Bacterial cultures were harvested four hours after induction and the polyhistidine-tagged proteins were purified by immobilized-metal affinity chromatography (Ni-NTA Agarose, Qiagen) according to the manufacturer's instructions. The proteins were eluted from the affinity resin with 200 mM imidazole in a buffer containing 50 mM $NaH_2PO_4$, 300 mM NaCl, pH 8.0, and subsequently desalted into phosphate buffered saline using PD-10 size exclusion chromatography columns (Amersham Biosciences).

Example 20

Preparation of Outer Membrane Vesicles

Outer membrane vesicles were purified in accordance with a previously established procedure (Kolling, G L et al., "Export of Virulence Genes and Shiga Toxin by Membrane Vesicles of *Escherichia coli* 0157: H7," *Appl Environ Microbiol* 65:1843-1848 (1999), which is hereby incorporated by reference in its entirety). Plasmids pClyA-GFP-His6 and pBAD18-Cm were transformed into *E. coli* vesicle-overproducing strain JC8031 (Bernadac, A et al., "*Escherichia coli* tol-pal Mutants Form Outer Membrane Vesicles," *J Bacteriol* 180:4872-4878 (1998), which is hereby incorporated by reference in its entirety), and selected in LB-chloramphenicol medium. Flasks containing 250 mL of medium were inoculated with overnight culture and allowed to grow until the $OD_{600}$ reached approximately 0.5. Protein expression was induced by addition of L-arabinose to a final concentration of 0.2%. Cell-free culture supernatants were collected 12 hours after induction and filtered through a 0.45 μm vacuum filter. Vesicles were isolated by ultracentrifugation (Beckman-Coulter Ti SW28 rotor, 141,000 g, 3 hours, 4° C.) and resuspended in phosphate buffered saline (PBS).

Example 21

Protein Analyses

Protein concentrations in OMV and purified recombinant protein preparations were quantified by the bicinchoninic acid assay (BCA Protein Assay, Pierce), with bovine serum albumin as the protein standard. Fluorescence activity of GFP in protein or OMV samples was measured in a microplate spectrofluorometer (Gemini EM, Molecular Devices) using excitation and emission wavelengths of 481 nm and 507 nm, respectively (Cormack, B P et al., "FACS-Optimized Mutants of the Green Fluorescent Protein (GFP)," *Gene* 173:33-38 (1996), which is hereby incorporated by reference in its entirety). For SDS-PAGE, samples were prepared in sample loading buffer containing β-mercaptoethanol and heated at 100° C. for 5 minutes prior to electrophoresis on 10% polyacrylamide gels. Proteins were transferred to polyvinylidine difluoride membranes for Western blot analysis and probed with monoclonal mouse anti-GFP IgG (Invitrogen, 1:2,000) or monoclonal mouse anti-polyHistidine IgG (1:3000, Sigma) primary antibodies, and horseradish peroxidase conjugated goat anti-mouse IgG (1:10,000, Jackson Immunoresearch) secondary antibody. Membranes were developed by autoradiography with ECL detection reagents (Pierce).

Example 22

Liquid Hemolysis Assay

The hemolytic activity of ClyA and ClyA-GFP was measured by a liquid hemolysis assay adopted from Rowe and Welch (Rowe et al., "Assays of Hemolytic Toxins," *Methods Enzymol* 235:657-667 (1994), which is hereby incorporated by reference in its entirety). Sheep erythrocytes (Becton Dickinson) were washed and diluted 1:100 in PBS. Aliquots of washed erythrocytes were transferred to microcentrifuge tubes and ClyA or ClyA-GFP was added to the appropriate concentration in a final volume of 1 mL in PBS. The samples were incubated at 37° C. for 30 min with gentle rotation. Cells and debris were sedimented in a microcentrifuge (4,000 rcf, 1.5 min), and the released hemoglobin in the supernatant was quantified by spectrophotometric detection at a wavelength of 540 nm. Hemolysis activity was reported relative to erythrocytes lysed in deionized water for 30 minutes at 37° C., which was considered 100% lysis.

Example 23

Dynamic Light Scattering

Dynamic light scattering measurements were performed with the Nanosizer Nano ZS (Malvern Instruments), using Dispersion Technology Software version 4.20 for data acquisition and analysis. OMV samples contained 60 ug/mL total protein in 1 mL of PBS. The refractive index and viscosity of water were used as parameter inputs.

Example 24

Microscopy

For negative staining electron microscopy, vesicles were stained with 2% uranyl acetate on 400-mesh Formar/carbon-coated copper grids and viewed in a FEI Tecnai F20 transmission electron microscope. For fluorescence microscopy, vesicles were placed on a glass slide, sealed with a cover slip, and examined using an Olympus BX41 microscope with GFP filter set.

Example 25

Lipopolysaccharide Detection

Bacterial lipopolysaccharide (LPS) concentrations were determined by measuring the presence of 2-keto-3-deoxyoctonate (KDO) according to a previously described colorimetric assay (Karkhanis et al., "New and Improved Microassay to Determine 2-Keto-3-Deoxyoctonate in Lipopolysaccharide of Gram-Negative Bacteria," *Anal Biochem* 85:595-601 (1978) and Herlax et al., "Role of Lipopolysaccharide on the Structure and Function of alpha-Hemolysin from *Escherichia coli*," *Chem Phys Lipids* 135:107-115 (2005), which are hereby incorporated by reference in their entirety). KDO forms part of the oligosaccharide core of the bacterial LPS molecule, with *E. coli* LPS containing two reactive KDO moieties per molecule (Lee et al., "Quantification of Bacterial Lipopolysaccharides by the Purpald Assay: Measuring Formaldehyde Generated from 2-keto-3-deoxyoctonate and Heptose at the Inner Core by Periodate Oxidation," *Anal Biochem* 267:161-168 (1999), which is hereby incorporated by reference in its entirety). OMV samples (45 µL) in PBS were combined with 0.2 N $H_2SO_4$ (5 µL) and heated at 100° C. for 20 minutes. The samples were cooled to room temperature for five minutes and then 25 µL of 0.04 M $NaIO_4$ was added to the mixture. Following 20 minutes of incubation at room temperature, 2% $NaAsO_2$ (65 µL) was added to the sample tubes and vortexed until the characteristic yellow color disappeared. Thiobarbituric acid (0.3%, 250 µL) was added and the samples were returned to the boiling water bath for 10 minutes, followed by immediate addition of dimethyl sulfoxide (125 µL). The samples were cooled to room temperature for five minutes and the absorbance was quantified at 550 nm in a microplate spectrophotometer. Calibration standards were prepared from KDO ammonium salt (Sigma-Aldrich).

Example 26

Immunization

Six groups of five BALB/c mice (Charles River Laboratories) each were immunized subcutaneously with 100 µL of PBS containing purified protein or OMV preparations as described. The six treatment groups were immunized with: 2.5 µg GFP (group I); 2.5 µg ClyA (group II); 5 µg ClyA-GFP (group III); 2.5 µg ClyA mixed with 2.5 µg GFP (group IV); 2.5 µg ClyA-GFP mixed with empty OMV (group V); and recombinant OMV equivalent to 2.5 µg ClyA-GFP (group VI). Two doses of vaccine were administered four weeks apart. Blood was collected from the mandibular sinus immediately prior to and two weeks following the first immunization, immediately prior to the booster dose, and at weekly intervals thereafter. The methods used in these animal studies were approved by the Institutional Animal Care and Use Committee at Cornell University.

Example 27

Enzyme-Linked Immunosorbent Assay (ELISA)

GFP-reactive antibodies were measured by indirect ELISA. Polystyrene microtiter 96-well plates (Maxisorp, Nunc Nalgene) were coated with GFP (5 µg/mL in carbonate buffer, pH 9.6) and incubated overnight at 4° C. Plates were blocked with 3% nonfat dry milk (Bio-Rad) in PBS containing 0.05% Tween-20 (PBST). Samples were serially diluted two fold in blocking buffer, in a range of 1:200 to 1:204,800, added to the wells, and incubated for 1.5 hours in a humidified chamber at 37° C. Plates were washed six times with PBST and then horseradish peroxidase-conjugated goat anti-mouse IgG (1:5,000, Jackson Immunoresearch), was added to the wells for 1 hour at 37° C. Following six additional washes with PBST, 3,3',5,5' tetramethylbenzidine substrate (1-Step Turbo TMB, Pierce) was added and the enzyme reaction proceeded for 20 minutes. The reaction was stopped with 2 M $H_2SO_4$. The absorbance was quantified in a microplate spectrophotometer at a wavelength of 450 nm. Statistical significance between treatment groups was determined by the non-parametric Wilcoxan rank-sum test, with p<0.05 considered significant.

Example 28

Figure 8A:
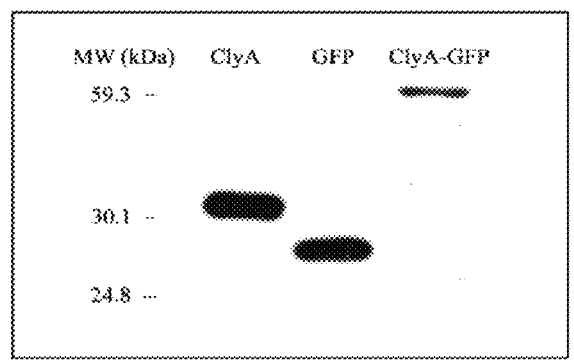
FIGS. 8A-8C show that the fusion of GFP to the C-terminus of ClyA results in expression of a 61 kDa chimeric protein that exhibits fluorescence and hemolytic activity.
Figure 8B:
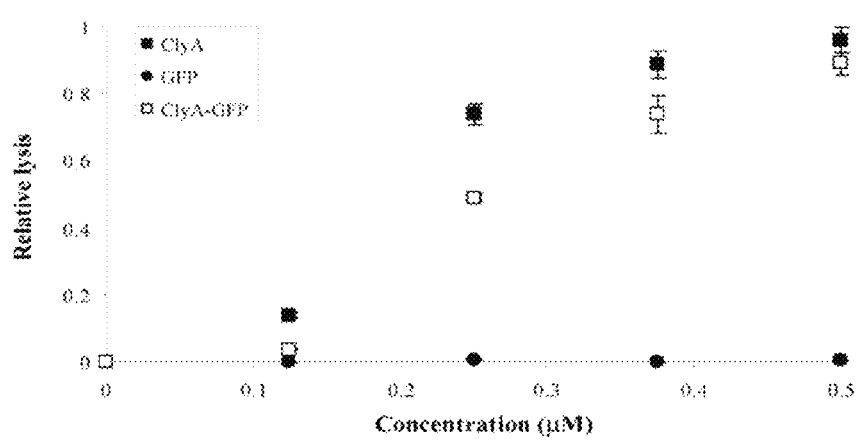
Figure 8C:
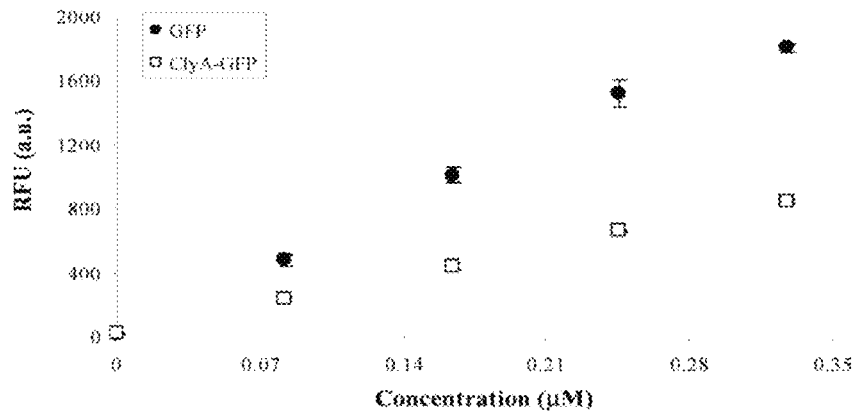

Fusion of Model Antigen GFP to ClyA Results in Expression of a 61 kDa Chimeric Protein that Retains the Native Activities of its Components To verify the expression of ClyA, GFP, and ClyA-GFP, proteins were purified by immobilized metal affinity chromatography from *E. coli* cultures and examined by Western blotting with anti-polyhistidine antibodies. FIG. 8A shows protein bands at 27 kDa corresponding to GFP, at 34 kDa corresponding to ClyA, and at 61 kDa corresponding to the expected molecular weight of ClyA-GFP. The ClyA-GFP fusion was further examined for the characteristic hemolytic and fluorescence activities of its constituent proteins. FIG. 8B shows that the degree of hemolysis of sheep erythrocytes increases with increasing concentration of both ClyA and ClyA-GFP, with ClyA-GFP exhibiting lower hemolysis activity than native ClyA at all tested concentrations. Similarly, fluorescence intensity measurements of ClyA-GFP indicate an increase in fluorescence intensity with increasing concentration, but diminished relative to free GFP (FIG. 8C). Together, these data show that the intrinsic hemolysis and fluorescence activities of ClyA and GFP, respectively, are retained when the two proteins are fused together as ClyA-GFP, albeit to a lesser degree than the free proteins likely due to protein proximity.

Example 29

Figure 9A:
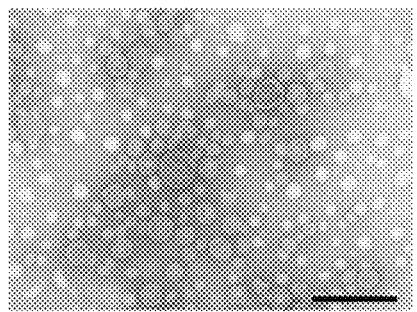
FIGS. 9A-9E depict the characterization of recombinant outer membrane vesicles from the E. coli vesicle hyperproducing strain, JC8031, expressing ClyA-GFP.
Figure 9B:
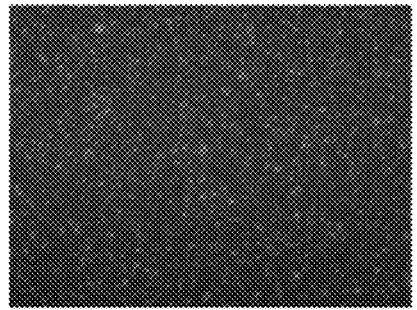
Figure 9C:
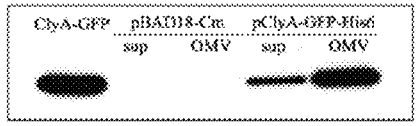
Figure 9D:
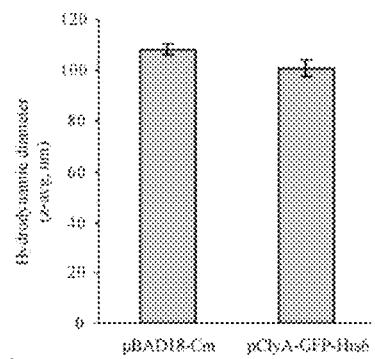
Figure 9E:
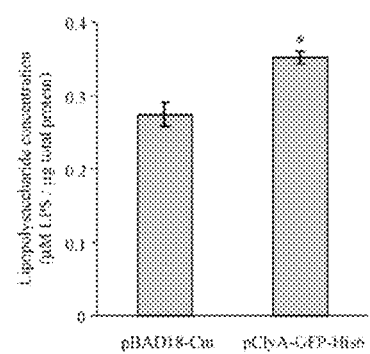
Figure 10A:
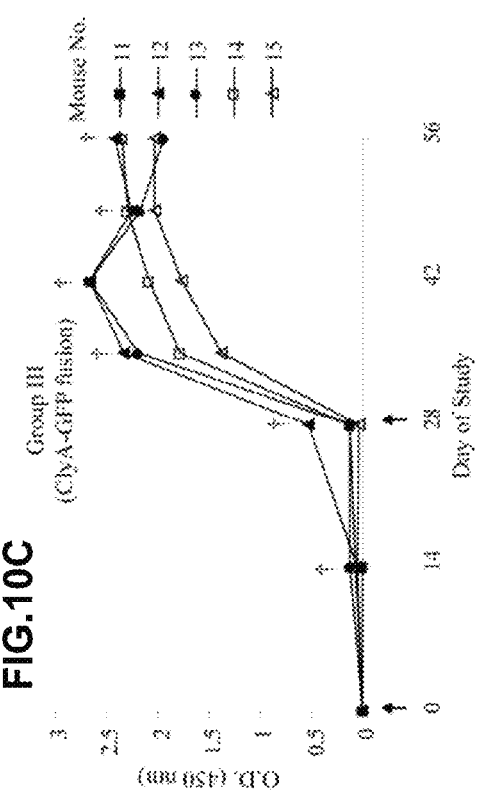
FIGS. 10A-10D illustrate the significantly enhanced immunogenicity of GFP when fused with ClyA. Individual host anti-GFP IgG responses in serum diluted 1:12,800. Groups of five BALB/c mice were subcutaneously immunized with: 2.5 µg GFP (group I/FIG. 10A), 2.5 µg ClyA (group II/FIG. 10B), 5 µg ClyA-GFP fusion (group III/FIG. 10C), and 2.5 µg ClyA mixed with 2.5 µg GFP (group IV/FIG. 10D). Mice were immunized on day 0 and day 28, as marked by the arrowheads in each chart. The daggers (†) represent statistical significance ($p<0.05$) of antibody titers in group III compared to titers in groups II and IV.
Figure 10B:
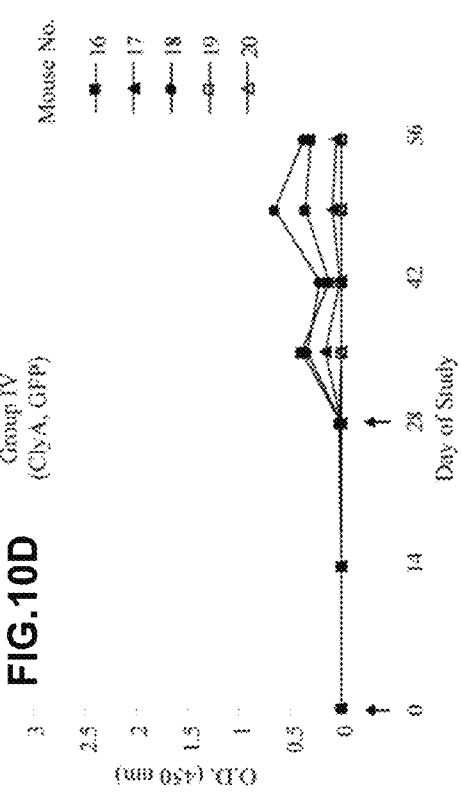
Figure 10C:
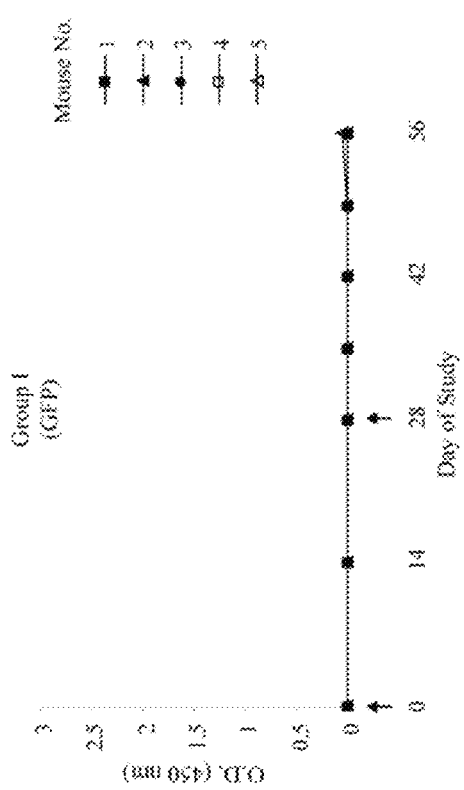
Figure 10D:
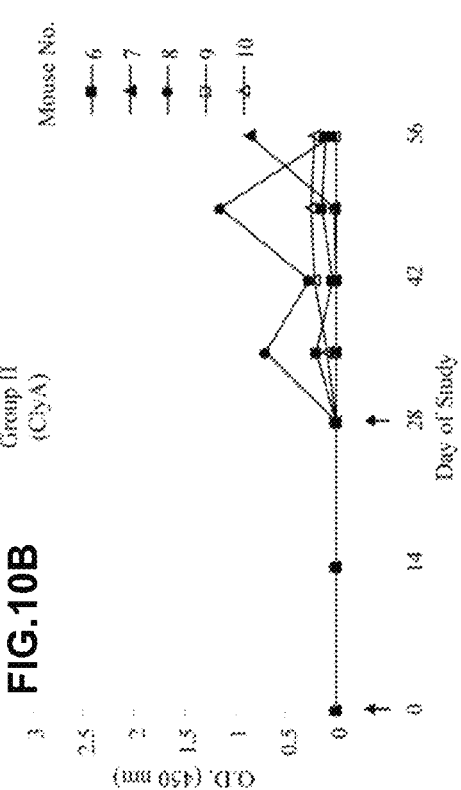

ClyA-GFP is Secreted to the Extracellular Medium of E. coli Cultures in Outer Membrane Vesicles Outer membrane vesicles were prepared from vesicle hyper-producing E. coli strain JC8031 transformed with plasmid pClyA-GFP-His6 (recombinant OMV) or the empty pBAD18-Cm cloning vector (empty OMV). Electron microscopy shows the spherical bilayered structure of OMV (FIG. 9A), is approximately 100 nm in diameter. ClyA-GFP fluorescence was observed in association with recombinant OMV (FIG. 9B), a finding confirmed by Western blotting with anti-GFP antibodies (FIG. 9C). Fluorescence intensity measurements and SDS-PAGE gel band densitometry indicate that ClyA-GFP comprises approximately 5% of the total protein content in OMV. Since expression of clyA in E. coli is strongly repressed under normal laboratory conditions (Westermark et al., "Silencing and Activation of ClyA Cytotoxin Expression in *Escherichia coli*," *J Bacteriol* 182:6347-6357 (2000), which is hereby incorporated by reference in its entirety), no free ClyA was detected in recombinant or empty outer membrane vesicles. Consistent with earlier observations (Kim et al., "Engineered Bacterial Outer Membrane Vesicles with Enhanced Functionality," *J Mol Biol* in press: doi:10.1016/j.jmb.2008.1003.1076 (2008), which is hereby incorporated by reference in its entirety), the association of ClyA-GFP recombinant OMV has no apparent effect on the average diameter of vesicles (FIG. 9D). Bacterial lipopolysaccharide (LPS) content in empty and recombinant OMV was measured via a colorimetric assay to detect 2-keto-3-deoxyoctonate (KDO), a core sugar component of LPS. The KDO assay indicates that recombinant OMV contain a slightly higher concentration of LPS, normalized by total protein content, than empty OMV (FIG. 9E).

Example 30

The Immunogenicity of GFP in Mice is Significantly Enhanced when Administered in Fusion with ClyA A green fluorescent protein (GFP) model weak antigen was fused to the C-terminus of ClyA to study the immunostimulatory effect of ClyA-antigen fusions in immunized mice. Subcutaneous immunization of BALB/c mice with ClyA-GFP elicited GFP-reactive antibody responses that were significantly higher than immunization with ClyA mixed with GFP (FIG. 10). A GFP-specific IgG response was detected beginning two weeks after priming in mice immunized with ClyA-GFP; this response was augmented by administration of the booster, and sustained for upwards of four weeks following the booster. No detectable anti-GFP IgG antibodies were observed until after boosting in any other treatment groups. Interestingly, immunization with GFP elicited little to no detectable response at any time during the study period, while in two mice immunization with ClyA alone triggered fluctuating levels of GFP cross-reactive antibody species following the booster. Antibody titers in the ClyA-GFP immunization group (group III) were significantly higher (p<0.05) than antibody titers in the unfused protein components treatment group (group IV) beginning at day 14 of the study and remained significantly higher through the conclusion of the study. GFP cross-reactive antibody levels in the treatment group immunized with ClyA and GFP separately (group IV) were statistically similar to the antibody levels generated by ClyA immunization alone (group II) at all time points throughout the study.

Example 31

Figure 11A:
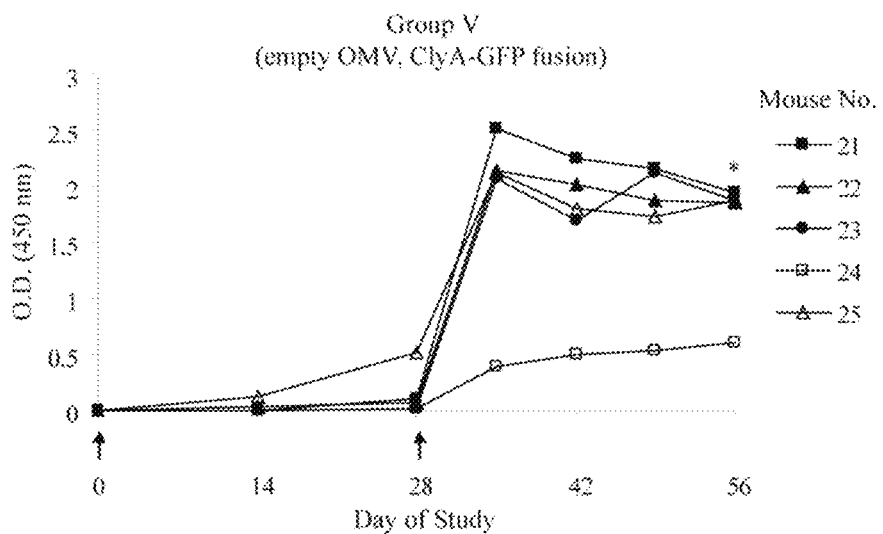
FIGS. 11A-11B demonstrate ClyA-GFP administered in recombinant OMV retains its immunogenicity in mice. Individual host anti-GFP IgG titers in serum diluted 1:12,800. Groups of five BALB/c mice were immunized with purified ClyA-GFP fusion mixed with empty OMV (group V/FIG. 11A), and ClyA-GFP fusion in association with recombinant OMV (group VI/FIG. 11B). The effective dose of ClyA-GFP in both treatment groups was 2.5 µg. Mice were immunized on day 0 and day 28, as marked by the arrowheads in each chart. The asterisks (*) denote statistically significant difference ($p<0.05$) in comparison with antibody titers in the purified ClyA-GFP treatment group (group III/FIG. 10C) on the corresponding day.
Figure 11B:
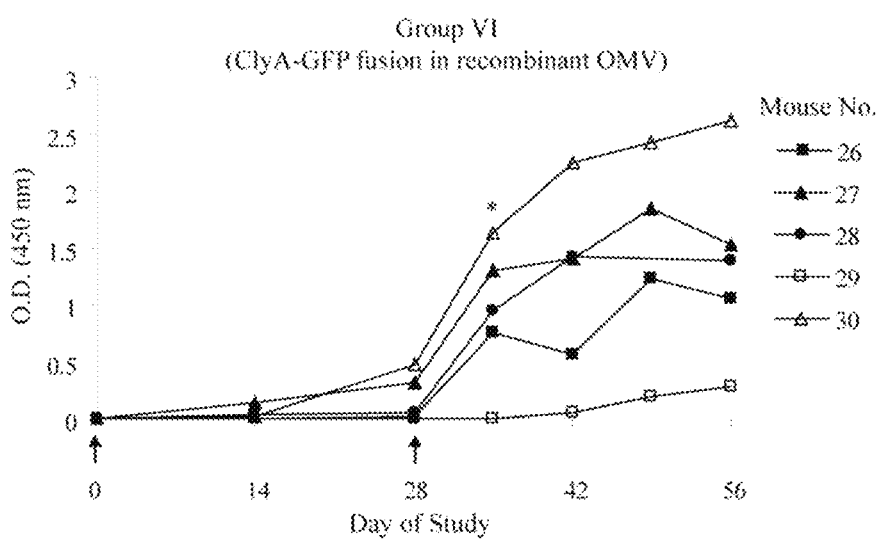

ClyA-GFP in an OMV Vaccine Formulation Retains its Immunogenicity in Mice while Bypassing Intensive Protein Purification Processes To examine the immunogenicity of ClyA-GFP secreted from whole E. coli cells in the form of outer membrane vesicles, BALB/c mice were immunized with empty OMV mixed with ClyA-GFP or with recombinant outer membrane vesicles containing the ClyA-GFP fusion (FIG. 11). The effective dose of ClyA-GFP in the OMV formulations (2.5 µg) was half the amount used in the purified protein immunizations in an effort to observe if association with OMV contributes any additional immune stimulating effect. Immunization with empty OMV combined with purified ClyA-GFP (group V) resulted in a GFP-specific response beginning at two weeks following priming and continuing for four weeks after the booster. Subcutaneous immunization with ClyA-GFP recombinant OMV (group IV) elicited similar GFP-reactive IgG responses starting two weeks following the initial dose that then markedly increased following immunization with the booster at day 28. At all time points throughout the study, antibody titers between group V and group VI remained statistically equivalent. Additionally, titers in OMV-immunized mice (groups V and VI) were statistically equivalent to those in group III with the exceptions of on day 56 for group V and on day 35 for group VI, when titers were significantly higher in group III (p<0.05).

Discussion of Examples 18-31

Vaccination remains one of the most cost-effective strategies for preventing infectious disease (Levine et al., "New Generation Vaccines, 3rd Edition," eds. (Marcel Dekker, Inc., New York) (2004), which is hereby incorporated by reference in its entirety). The safety of protein subunit vaccines over whole organisms makes them particularly attractive for administration to wide swaths of the human population, healthy and immunocompromised individuals alike. A major limiting factor in the further development of subunit vaccines, however, remains the poor immunogenicity of purified antigens alone. Despite advances in adjuvant research, the only compounds currently licensed for human use in North America remains aluminum salts that have potential to cause inflammatory or allergic reactions (Gupta R K, "Aluminum Compounds as Vaccine Adjuvants," *Adv Drug Delivery Rev* 32:155-172 (1998), which is hereby incorporated by reference in its entirety). Although particulate antigen delivery systems have emerged as promising strategies for antigen delivery, the added steps of loading or adsorbing purified antigens with particles on a large manufacturing scale can rapidly render these systems cost-prohibitive, a consideration that is especially relevant to vaccines for diseases prevalent in the developing world.

Owing largely to their size, plasticity, and demonstrated safety profile in humans, OMV are attractive vehicles for vaccine delivery. In a demonstration of the remarkable tunability of OMV, heterologous proteins fused with the native bacterial protein ClyA are efficiently transported in their native functional forms to vesicles (Kim et al., "Engineered Bacterial Outer Membrane Vesicles with Enhanced Functionality," *J Mol Biol* in press: doi:10.1016/j.jmb.2008.1003.1076 (2008), which is hereby incorporated by reference in its entirety). Previous work also points to the utility of ClyA in enhancing the immunogenicity of foreign antigens when secreted from a live attenuated *Salmonella* vector, suggesting the possibility that antigens may be exported from live vectors in OMV (Galen et al., "Adaptation of the Endogenous *Salmonella enterica* serovar typhi ClyA-Encoded Hemolysin for Antigen Export Enhances the Immunogenicity of Anthrax Protective Antigen Domain 4 Expressed by the Attenuated Live-Vector Vaccine Strain CVD 908-htrA," *Infect Immun* 72:7096-7106 (2004), which is hereby incorporated by reference in its entirety).

This work demonstrates that recombinant OMV are a potent adjuvant and carrier system for poorly immunogenic proteins. Specifically, a recombinant OMV vaccine containing ClyA fused with a model green fluorescent protein (GFP) foreign antigen elicited strong GFP-specific humoral responses in immunized mice. These results introduce recombinant OMV vaccines as a versatile strategy for potentially delivering a host of poorly immunogenic proteins. An important characteristic of OMV is that they are isolated by a *facile* ultracentrifugation, effectively eliminating costly purification or formulation processes connected with other particulate delivery systems and traditional protein subunit vaccines.

Leveraging the novel secretory behavior of ClyA, a recombinant OMV vaccine containing the model GFP antigen was constructed by fusing GFP with the C-terminus of ClyA. Consistent with previously observed results (Kim et al., "Engineered Bacterial Outer Membrane Vesicles with Enhanced Functionality," *J Mol Biol* in press: doi:10.1016/j.jmb.2008.1003.1076 (2008), which is hereby incorporated by reference in its entirety), purification of the engineered ClyA-GFP fusion protein from *E. coli* culture resulted in a 61 kDa product (FIG. 8A). Functionality assays were performed to verify that ClyA-GFP in fusion retained the native biological activity of ClyA and GFP. The specific fluorescence and hemolysis activity of ClyA-GFP under the specified assay conditions was diminished relative to the unfused constituent proteins (FIG. 8B and FIG. 8C), which is similar to a previous observation made with other ClyA fusion partners (del Castillo et al., "Secretion of the *Escherichia coli* K-12 SheA Hemolysin is Independent of its Cytolytic Activity," *FEMS Microbiol Lett* 204:281-285 (2001), which is hereby incorporated by reference in its entirety). This retention of protein activity shows that proteins fused with ClyA maintain their conformations and indicates that ClyA may be an amenable carrier for both linear epitopes and conformational antigens.

Recombinant OMV were purified from non-pathogenic *E. coli* and examined for the presence of ClyA-GFP and LPS (FIG. 9A). Western blotting with anti-GFP antibodies verified the presence of ClyA-GFP in OMV; encapsulation of the active fusion protein in vesicles occurs through automatic secretion and thus requires no a priori antigen purification, unlike other particulate delivery systems. Intriguingly, recombinant OMV contained higher levels of LPS (when normalized with protein content) than did empty vesicles. Because LPS can be counterproductive in vaccines, future work may require depletion of LPS from vesicles, as in the case of the previously described meningitis vaccines (Claassen et al., "Production, Characterization and Control of a *Neisseria meningitidis* Hexavalent Class 1 Outer Membrane Protein Vontaining Vesicle Vaccine," *Vaccine* 14:1001-1008 (1996), which is hereby incorporated by reference in its entirety).

The results in FIG. 10, depicting antibody titers in mice immunized with purified proteins, show ClyA to be an effective carrier protein for enhancing the immunogenicity of GFP in mice. The immunogenicity of ClyA fusion proteins was first shown in a study by Galen et al (Galen et al., "Adaptation of the Endogenous *Salmonella enterica* serovar typhi ClyA-Encoded Hemolysin for Antigen Export Enhances the Immunogenicity of Anthrax Protective Antigen Domain 4 Expressed by the Attenuated Live-Vector Vaccine Strain CVD 908-htrA," *Infect Immun* 72:7096-7106 (2004), which is hereby incorporated by reference in its entirety), where the observed enhancement in the immune response to the antigens was postulated to be largely dependent on export from a live *Salmonella* vector. Here, the results show that antigen fusion with ClyA is directly responsible for enhanced immunogenicity. As a bacterial cytolytic protein from enterobacteria (Eifler et al., "Cytotoxin ClyA from *Escherichia coli* Assembles to a 13-meric Pore Independent of its Redox-State," *Embo Journal* 25:2652-2661 (2006), which is hereby incorporated by reference in its entirety), ClyA joins the ranks of other known toxins with adjuvant properties such as diphtheria toxin or heat-labile enterotoxin (Lavelle et al., "*Vaccine Adjuvants: Immunological and Clinical Principles*," eds. Hackett C J & Harn D A (Humana Press, Totowa, N.J.), pp. 111-154 (2006), which is hereby incorporated by reference in its entirety). While no pathological effects of were observed in mice immunized with ClyA in this study, detoxification of ClyA through mutation, truncation, or chemical methods may attenuate any possible toxicity while retaining its immunomodulatory capabilities.

Unlike other known bacterial toxin adjuvants, however, enhancement in the immune response to GFP was not observed when mice were immunized with a mixture of unfused ClyA and GFP. While the specific mechanisms that drive the immunostimulatory behavior of ClyA remain unclear, physical or chemical conjugation to protein carriers has frequently improved the immunogenicity of otherwise poorly immunogenic antigens by increasing the antigen size or improving antigen organization to optimize the B cell response (Wu et al., "Sustained High-Titer Antibody Responses Induced by Conjugating a Malarial Vaccine Candidate to Outer-Membrane Protein Complex," *Proc Nat Acad Sci USA* 103:18243-18248 (2006); Koser et al., "Rabies Virus Nucleoprotein as a Carrier for Foreign Antigens," *Proc Nat Acad Sci USA* 101:9405-9410 (2004); and Bachmann et al., "The Influence of Antigen Organization on B-Cell Responsiveness," *Science* 262:1448-1451 (1993), which are hereby incorporated by reference in their entirety). In general, the ability for antigens to be presented in the proper structure to activate B cell proliferation requires efficient antigen processing by antigen presenting cells and co-stimulation by T-cells. Further studies on ClyA and its interaction with the immune system are necessary to more fully characterize the immune enhancing activity of ClyA.

To examine the humoral immune response to ClyA-GFP when delivered in OMV, mice were immunized with empty OMV mixed with purified ClyA-GFP (group V), or with the recombinant OMV formulation containing ClyA-GFP (FIG. 11, group VI). The results show that the immunostimulatory effect of ClyA-GFP is retained in vesicles. The kinetics of the antibody response to recombinant OMV appears to occur slightly more slowly than the response to purified ClyA-GFP. On day 35 of the study, anti-GFP titers in the recombinant OMV group (FIG. 11, group VI) were lower than in the group immunized with purified ClyA-GFP (FIG. 10, group III), however the titers in these two treatment groups are statistically equal to each other beginning at day 42. These results with recombinant OMV are remarkable especially when taking into account that the effective dose of the ClyA-GFP fusion in the OMV formulations were half that of the purified protein treatments. While the decreased dosage may be a factor in the delayed response to ClyA-GFP in mice immunized with recombinant OMV over the purified protein, it may also be possible that OMV contributes additional immunostimulatory activity.

Comparison between the empty and recombinant OMV treatments (FIG. 11) suggests that anti-GFP titers are largely independent of the direct association of ClyA-GFP with OMV. There remains the possibility, however, that non-specific association of purified ClyA-GFP with blank OMV may make the two OMV populations virtually indistinguishable to the immune system. Association of ClyA-GFP with vesicles does appear, however, to result in a more prolonged antibody response. At day 56, the antibody titers in group V (empty OMV with ClyA-GFP) are statistically decreased relative to group III (purified ClyA-GFP), while the titers in the recombinant OMV treatment group exhibited no such decrease. Similar to other particulate delivery systems, encapsulation of antigens within OMV may protect antigens from protease degradation in vivo, resulting in more prolonged B-cell activation.

Recombinant OMV are unique particulate vaccine delivery vectors with adjuvant and carrier activity that combine features borrowed from both synthetic and living antigen delivery systems. These vesicles are non-replicating entities that are able to avoid the potential safety concerns associated with attenuated living bacteria. As nanoscale spherical structures comprising mainly protein and lipid, OMV may share some structural or compositional similarity with liposome or proteosome carriers, but do not require extensive formulation. In perhaps the most significant departure from particulate systems or traditional subunit vaccines, recombinant OMV do not require the a priori purification of the antigen. The intrinsic ability of ClyA-antigen fusions to be transported to OMV, while retaining biological activity, removes expensive and often problematic protein purification operations. These advantages in processing and functionality, together with the additional possibilities of further engineering lumenal or surface vesicle features demonstrate that OMV are a uniquely tunable platform for the delivery of poorly immunogenic antigens for vaccines against infectious disease.

As new disease threats arise and humanitarian needs become ever more urgent, attention continues to focus on the development of vaccines to safely induce protective immune responses to pathogens that cause debilitating disease throughout the world. This work illuminates the potential of recombinant OMV technology to overcome the significant safety and economic limitations that often arise in the course of vaccine development. A model green fluorescent protein fused with the bacterial hemolysin ClyA was secreted in outer membrane vesicles while maintaining the biological activity of both components. These recombinant OMV were administered to mice and found to be highly immunogenic, eliciting high titers against GFP while immunization with GFP alone failed to elicit any significant humoral response. Combining adjuvant and carrier activity, recombinant OMV enhances the response to an otherwise poorly immunogenic antigen and circumvents the protein purification requirements of traditional subunit vaccines and particulate antigen delivery modalities.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

SEQUENCE LISTING

<160> NUMBER OF SEQ ID NOS: 16

<210> SEQ ID NO 1
<211> LENGTH: 303
<212> TYPE: PRT
<213> ORGANISM: Escherichia coli

<400> SEQUENCE: 1

Met Thr Glu Ile Val Ala Asp Lys Thr Val Glu Val Val Lys Asn Ala
1               5                   10                  15

Ile Glu Thr Ala Asp Gly Ala Leu Asp Leu Tyr Asn Lys Tyr Leu Asp
            20                  25                  30

Gln Val Ile Pro Trp Gln Thr Phe Asp Glu Thr Ile Lys Glu Leu Ser
        35                  40                  45

Arg Phe Lys Gln Glu Tyr Ser Gln Ala Ala Ser Val Leu Val Gly Asp
    50                  55                  60

Ile Lys Thr Leu Leu Met Asp Ser Gln Asp Lys Tyr Phe Glu Ala Thr
65                  70                  75                  80

Gln Thr Val Tyr Glu Trp Cys Gly Val Ala Thr Gln Leu Leu Ala Ala
                85                  90                  95

Tyr Ile Leu Leu Phe Asp Glu Tyr Asn Glu Lys Lys Ala Ser Ala Gln
            100                 105                 110

Lys Asp Ile Leu Ile Lys Val Leu Asp Asp Gly Ile Thr Lys Leu Asn

```
                    115                 120                 125
Glu Ala Gln Lys Ser Leu Leu Val Ser Ser Gln Ser Phe Asn Asn Ala
            130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Lys Ile Arg Lys Glu
                165                 170                 175

Ala Tyr Ala Gly Ala Ala Gly Val Val Ala Gly Pro Phe Gly Leu
            180                 185                 190

Ile Ile Ser Tyr Ser Ile Ala Ala Gly Val Val Glu Gly Lys Leu Ile
                195                 200                 205

Pro Glu Leu Lys Asn Lys Leu Lys Ser Val Gln Asn Phe Phe Thr Thr
    210                 215                 220

Leu Ser Asn Thr Val Lys Gln Ala Asn Lys Asp Ile Asp Ala Ala Lys
225                 230                 235                 240

Leu Lys Leu Thr Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Glu Ala Ala Lys Lys Met Ile Asn Thr Cys Asn Glu Tyr
    275                 280                 285

Gln Lys Arg His Gly Lys Lys Thr Leu Phe Glu Val Pro Glu Val
    290                 295                 300

<210> SEQ ID NO 2
<211> LENGTH: 1080
<212> TYPE: DNA
<213> ORGANISM: Escherichia coli

<400> SEQUENCE: 2
agaaataaag acattgacgc atcccgcccg gctaactatg aattagatga agtaaaattt      60
attaatagtt gtaaaacagg agtttcatta caatttatat atttaaagag gcgaatgatt     120
atgactgaaa tcgttgcaga taaaacggta gaagtagtta aaaacgcaat cgaaaccgca     180
gatggagcat tagatcttta taataaatat ctcgatcagg tcatcccctg cagaccttta     240
gatgaaacca taaagagttt aagtcgcttt aaacaggagt attcacaggc agcctccgtt     300
ttagtcggcg atattaaaac cttacttatg gatagccagg ataagtattt tgaagcaacc     360
caaacagtgt atgaatggtg tggtgttgcg acgcaattgc tcgcagcgta tattttgcta     420
tttgatgagt acaatgagaa gaaagcatcc gcccagaaag acattctcat taaggtactg     480
gatgacggca tcacgaagct gaatgaagcg caaaaatccc tgctggtaag ctcacaaagt     540
ttcaacaacg cttccgggaa actgctggcg ttagatagcc agttaaccaa tgattttca     600 gaaaaagca gctatttcca gtcacaggta gataaaatca ggaaggaagc atatgccggt     660
gccgcagccg gtgtcgtcgc cggtccattt ggattaatca tttcctattc tattgctgcg     720
ggcgtagttg aaggaaaact gattccagaa ttgaagaaca gttaaaatc tgtgcagaat     780 ttctttacca ccctgtctaa cacggttaaa caagcgaata agatatcga tgccgccaaa     840 ttgaaattaa ccaccgaaat agccgccatc ggtgagataa aaacgaaaac tgaaacaacc     900
agattctacg ttgattatga tgatttaatg ctttctttgc taaagaagc ggccaaaaaa     960 atgattaaca cctgtaatga gtatcagaaa agacacggta aaagacact ctttgaggta    1020 cctgaagtct gataagcgat tattctctcc atgtactcaa ggtataaggt ttatcacatt    1080
```

<210> SEQ ID NO 3
<211> LENGTH: 303
<212> TYPE: PRT
<213> ORGANISM: Salmonella enterica

<400> SEQUENCE: 3

Met Thr Gly Ile Phe Ala Glu Gln Thr Val Glu Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ile Gly Glu Ile Lys Thr Glu
                245                 250                 255

Thr Glu Thr Thr Arg Phe Tyr Val Asp Tyr Asp Asp Leu Met Leu Ser
                260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val
    290                 295                 300

<210> SEQ ID NO 4
<211> LENGTH: 1102
<212> TYPE: DNA
<213> ORGANISM: Salmonella enterica

<400> SEQUENCE: 4
ggaggtaata ggtaagaata ctttataaaa caggtactta attgcaattt atatatttaa      60
agaggcaaat gattatgacc ggaatatttg cagaacaaac tgtagaggta gttaaaagcg     120
cgatcgaaac cgcagatggg gcattagatc tttataacaa ataccctcgac caggtcatcc    180

```
cctggaagac ctttgatgaa accataaaag agttaagccg ttttaaacag gagtactcgc      240
aggaagcttc tgttttagtt ggtgatatta aagttttgct tatggacagc caggacaagt      300
attttgaagc gacacaaact gtttatgaat ggtgtggtgt cgtgacgcaa ttactctcag      360
cgtatatttt actatttgat gaatataatg agaaaaaagc atcagcccag aaagacattc      420
tcattaggat attagatgat ggtgtcaaga aactgaatga agcgcaaaaa tctctcctga      480
caagttcaca agtttcaac aacgcttccg gaaaactgct ggcattagat agccagttaa       540
ctaatgattt ttcggaaaaa agtagttatt ccagtcaca ggtggataga attcgtaagg        600
aagcttatgc cggtgctgca gccggcatag tcgccggtcc gtttggatta attatttcct      660
attctattgc tgcgggcgtg attgaaggga aattgattcc agaattgaat aacaggctaa      720
aaacagtgca aaatttcttt actagcttat cagctacagt gaaacaagcg aataaagata      780
tcgatgcggc aaaattgaaa ttagccactg aaatagcagc aattggggag ataaaaacgg      840
aaaccgaaac aaccagattc tacgttgatt atgatgattt aatgctttct ttattaaaag      900
gagctgcaaa gaaaatgatt aacacctgta atgaatacca acaaagacac ggtaagaaga      960
cgcttttcga ggttcctgac gtctgataca ttttcattcg atctgtgtac ttttaacgcc     1020
cgatagcgta aagaaaatga gagacggaga aaaagcgata ttcaacagcc cgataaacaa     1080
gagtcgttac cgggctgacg ag                                              1102
```

<210> SEQ ID NO 5
<211> LENGTH: 303
<212> TYPE: PRT
<213> ORGANISM: Salmonella paratyphi

<400> SEQUENCE: 5

```
Met Thr Gly Ile Phe Ala Glu Gln Thr Val Glu Val Val Lys Ser Ala
1               5                   10                  15

Ile Glu Thr Ala Asp Gly Ala Leu Asp Phe Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Asn Lys Leu Asn
        115                 120                 125

Glu Ala Gln Lys Ser Leu Leu Gly Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205
```

```
Pro Glu Leu Asn Asp Arg Leu Lys Ala Val Gln Asn Phe Phe Thr Ser
    210                 215                 220

Leu Ser Val Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Leu Glu Val Pro Asp Ile
    290                 295                 300

<210> SEQ ID NO 6
<211> LENGTH: 1102
<212> TYPE: DNA
<213> ORGANISM: Salmonella paratyphi

<400> SEQUENCE: 6
ggaggcaata ggtaggaata agttataaaa caatagctta attgcaattt atatatttaa     60
agaggcaaat gattatgact ggaatatttg cagaacaaac tgtagaggta gttaaaagcg    120
cgatcgaaac cgcagatggg gcattagatt tttataacaa atacctcgac caggttatcc    180
cctggaagac ctttgatgaa accataaaag agttaagccg ttttaaacag gagtactcgc    240
aggaagcttc tgttttagtt ggtgatatta agttttgct tatggacagc caggataagt    300
attttgaagc gacacaaact gtttatgaat ggtgtggtgt cgtgacgcaa ttactctcag    360
cgtatatttt actatttgat gaatataatg agaaaaaagc atcagcgcag aaagacattc    420
tcatcaggat attagatgat ggcgtcaata aactgaatga agcgcaaaaa tctctcctgg    480
gaagttcaca agtttcaac aacgcttcag gaaaactgct ggcattagat agccagttaa    540
ctaatgattt ctcggaaaaa agtagttatt ccagtcaca ggtggataga attcgtaagg    600
aagcttatgc cggtgctgca gcaggcatag tcgccggtcc gtttggatta attatttcct    660
attctattgc tgcgggcgtg attgaaggga aattgattcc agaattgaat gacaggctaa    720
aagcagtgca aaatttcttt actagcttat cagtcacagt gaaacaagcg aataaagata    780
tcgatgcggc aaaattgaaa ttagccactg aaatagcagc aattggggag ataaaaacgg    840
aaaccgaaac aaccagattc tacgttgatt atgatgattt aatgctttct ttactaaaag    900
gagctgcaaa gaaaatgatt aacacctgta atgaatacca acaaaggcac ggtaagaaga    960
cgcttctcga ggttcctgac atctgataca ttttcattcg ctctgtttac ttttaacgcc   1020
cgatagcgtg aagaaaatga gagacggaga aaaagcgata ttcaacagcc cgataaacaa   1080
gagtcgttac cgggctggcg ag                                           1102

<210> SEQ ID NO 7
<211> LENGTH: 113
<212> TYPE: PRT
<213> ORGANISM: Shigella flexneri

<400> SEQUENCE: 7

Met Thr Glu Ile Val Ala Asp Lys Thr Val Glu Val Val Lys Asn Ala
1               5                   10                  15

Ile Glu Thr Ala Asp Gly Ala Leu Asp Leu Tyr Asn Lys Tyr Leu Asp
            20                  25                  30

Gln Val Ile Pro Trp Gln Thr Phe Asp Glu Thr Ile Lys Glu Leu Ser
```

```
                    35                  40                  45
Arg Phe Lys Gln Glu Tyr Ser Gln Ala Ala Ser Val Leu Val Gly Asp
 50                  55                  60

Ile Lys Thr Leu Leu Met Asp Ser Gln Asp Lys Tyr Phe Glu Ala Thr
 65                  70                  75                  80

Gln Thr Val Tyr Glu Trp Cys Gly Val Ala Thr Gln Leu Leu Ala Ala
                 85                  90                  95

Tyr Ile Leu Leu Phe Asp Glu Tyr Asn Glu Lys Lys Ala Ser Ala Pro
                100                 105                 110

His
```

```
<210> SEQ ID NO 8
<211> LENGTH: 904
<212> TYPE: DNA
<213> ORGANISM: Shigella flexneri

<400> SEQUENCE: 8
atgactgaaa tcgttgcaga taaaacggta gaagtagtta aaaacgcaat cgaaaccgca      60
gatggagcat tagatcttta taataaatat ctcgatcagg tcatcccctg cagaccttt     120 gatgaaacca taaagagtt aagtcgcttt aaacaggagt attcacaggc agcctccgtt     180
ttagtcggcg atattaaaac cttacttatg gatagccagg ataagtattt tgaagcaacc     240
caaacagtgt atgaatggtg tggtgttgcg acgcaattgc tcgcagcgta tattttgcta     300
tttgatgagt acaatgagaa gaaagcatcc gcccctcatt aaggtactgg atgacggcat     360
cacgaagctg aatgaagcgc aaaattccct gctggtaagc tcacaaagtt caacaacgc     420 ttccgggaaa ctgctggcgt tagatagcca gttaaccaat gattttttcag aaaaaagcag     480 ctatttccag tcacaggtag ataaaatcag gaaggaagcg tatgccggtg ccgcagccgg     540
tgtcgtcgcc ggtccatttg gtttaatcat ttcctattct attgctgcgg cgtagttga     600 agggaaactg attccagaat tgaagaacaa gttaaaatct gtgcagagtt tctttaccac     660
cctgtctaac acggttaaac aagcgaataa agatatcgat gccgccaaat tgaaattaac     720
caccgaaata gccgccatcg gggagataaa aacggaaact gaaaccacca gattctatgt     780
tgattatgat gatttaatgc tttctttgct aaaagcagcg gccaaaaaaa tgattaacac     840
ctgtaatgag tatcagaaaa gacacggtaa aaagacactc tttgaggtac ctgaagtctg     900
ataa                                                                 904
```

```
<210> SEQ ID NO 9
<211> LENGTH: 113
<212> TYPE: PRT
<213> ORGANISM: Artificial
<220> FEATURE:
<223> OTHER INFORMATION: ClyA consensus sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
```

<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid

<400> SEQUENCE: 9

Met Thr Xaa Ile Xaa Ala Xaa Xaa Thr Val Glu Val Val Lys Xaa Ala
1               5                   10                  15

Ile Glu Thr Ala Asp Gly Ala Leu Asp Xaa Tyr Asn Lys Tyr Leu Asp
            20                  25                  30

Gln Val Ile Pro Trp Xaa Thr Phe Asp Glu Thr Ile Lys Glu Leu Ser
        35                  40                  45

Arg Phe Lys Gln Glu Tyr Ser Gln Xaa Ala Ser Val Leu Val Gly Asp
50                  55                  60

Ile Lys Xaa Leu Leu Met Asp Ser Gln Asp Lys Tyr Phe Glu Ala Thr
65                  70                  75                  80

Gln Thr Val Tyr Glu Trp Cys Gly Val Xaa Thr Gln Leu Leu Xaa Ala
            85                  90                  95

Tyr Ile Leu Leu Phe Asp Glu Tyr Asn Glu Lys Lys Ala Ser Ala Xaa
            100                 105                 110

Xaa

<210> SEQ ID NO 10
<211> LENGTH: 916
<212> TYPE: DNA
<213> ORGANISM: Artificial
<220> FEATURE:
<223> OTHER INFORMATION: ClyA consensus sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature -continued

```
<222> LOCATION: (22)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
```

-continued

```
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (200)..(202)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (336)..(346)
<223> OTHER INFORMATION: n is a, c, g, or t
```

-continued

```
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (370)..(371)
<223> OTHER INFORMATION: n is a, c, g, or t
<220> FEATURE:
<221> NAME/KEY: misc_feature
<222> LOCATION: (375)..(376)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (407)..(408)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (481)..(481)
```

```
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (511)..(511)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (520)..(521)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (553)..(554)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (637)..(638)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
```

-continued

```
<222> LOCATION: (644)..(644)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (679)..(682)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
```

```
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (820)..(821)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (868)..(869)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (883)..(883)
<223> OTHER INFORMATION: n is a, c, g, or t
<220> FEATURE:
<221> NAME/KEY: misc_feature
<222> LOCATION: (889)..(889)
<223> OTHER INFORMATION: n is a, c, g, or t
<220> FEATURE:
<221> NAME/KEY: misc_feature
<222> LOCATION: (892)..(893)
<223> OTHER INFORMATION: n is a, c, g, or t
<220> FEATURE:
<221> NAME/KEY: misc_feature
<222> LOCATION: (895)..(895)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t
<220> FEATURE:
<221> NAME/KEY: misc_feature
<222> LOCATION: (907)..(908)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t

<400> SEQUENCE: 10
natgacngna atnnttgcag annaaaacngt agangtagtt aaaancgcna tcgaaaccgc    60
```

```
agatggngca ttagatnttt ataanaaata nctcgancag gtnatcccct ggnagacctt      120
tgatgaaacc ataaaagagt taagncgntt taaacaggag tantcncagg nagcntcngt      180
tttagtnggn gatattaaan nnttncttat gganagccag ganaagtatt ttgaagcnac      240
ncaaacngtn tatgaatggt gtggtgtngn gacgcaattn ctcncagcgt atattttnct      300
atttgatgan tanaatgaga anaaagcatc ngcncnnnnn nnnnnnctca tnangntant      360
ngatganggn ntcannaanc tgaatgaagc gcaaaantcn ctnctgnnaa gntcacaaag      420
tttcaacaac gcttcnggna aactgctggc nttagatagc cagttaacna atgatttntc      480
ngaaaaaagn agntatttcc agtcacaggt ngatanaatn ngnaaggaag cntatgccgg      540
tgcngcagcn ggnntngtcg ccggtccntt tggnttaatn atttcctatt ctattgctgc      600
gggcgtnntt gaaggnaaan tgattccaga attgaannac angntaaaan cngtgcanan      660
tttctttacn ancntntcnn nnacngtnaa acaagcgaat aaagatatcg atgcngcnaa      720
attgaaatta nccacngaaa tagcngcnat nggngagata aaaacggaaa cngaaacnac      780
cagattctan gttgattatg atgatttaat gctttctttn ntaaaagnag cngcnaanaa      840
aatgattaac acctgtaatg antancanna aagncacggt aanaagacnc tnntngaggt      900
ncctganntc tgatan                                                      916
```

<210> SEQ ID NO 11
<211> LENGTH: 303
<212> TYPE: PRT
<213> ORGANISM: Artificial
<220> FEATURE:
<223> OTHER INFORMATION: ClyA consensus sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:

```
<221> NAME/KEY: misc_feature
<222> LOCATION: (118)..(119)
<223> OTHER INFORMATION: Xaa can be any naturally occurring amino acid
<220> FEATURE:
<221> NAME/KEY: misc_feature
<222> LOCATION: (124)..(125)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (212)..(214)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (302)..(303)
<223> OTHER INFORMATION: Xaa can be any naturally occurring amino acid

<400> SEQUENCE: 11

Met Thr Xaa Ile Xaa Ala Xaa Xaa Thr Val Glu Val Val Lys Xaa Ala
1               5                   10                  15

Ile Glu Thr Ala Asp Gly Ala Leu Asp Xaa Tyr Asn Lys Tyr Leu Asp
            20                  25                  30

Gln Val Ile Pro Trp Xaa Thr Phe Asp Glu Thr Ile Lys Glu Leu Ser
        35                  40                  45

Arg Phe Lys Gln Glu Tyr Ser Gln Xaa Ala Ser Val Leu Val Gly Asp
    50                  55                  60

Ile Lys Xaa Leu Leu Met Asp Ser Gln Asp Lys Tyr Phe Glu Ala Thr
65                  70                  75                  80

Gln Thr Val Tyr Glu Trp Cys Gly Val Xaa Thr Gln Leu Leu Xaa Ala
                85                  90                  95
```

-continued

```
Tyr Ile Leu Leu Phe Asp Glu Tyr Asn Glu Lys Lys Ala Ser Ala Gln
                100                 105                 110

Lys Asp Ile Leu Ile Xaa Xaa Leu Asp Asp Gly Xaa Xaa Lys Leu Asn
            115                 120                 125

Glu Ala Gln Lys Ser Leu Leu Xaa Ser Ser Gln Ser Phe Asn Asn Ala
        130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Xaa Ile Arg Lys Glu
                165                 170                 175

Ala Tyr Ala Gly Ala Ala Gly Xaa Val Ala Gly Pro Phe Gly Leu
            180                 185                 190

Ile Ile Ser Tyr Ser Ile Ala Ala Gly Val Xaa Glu Gly Lys Leu Ile
        195                 200                 205

Pro Glu Leu Xaa Xaa Xaa Leu Lys Xaa Val Gln Asn Phe Phe Thr Xaa
    210                 215                 220

Leu Ser Xaa Thr Val Lys Gln Ala Asn Lys Asp Ile Asp Ala Ala Lys
225                 230                 235                 240

Leu Lys Leu Xaa Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Xaa Ala Ala Lys Lys Met Ile Asn Thr Cys Asn Glu Tyr
        275                 280                 285

Gln Xaa Arg His Gly Lys Lys Thr Leu Xaa Glu Val Pro Xaa Xaa
    290                 295                 300

<210> SEQ ID NO 12
<211> LENGTH: 1039
<212> TYPE: DNA
<213> ORGANISM: Artificial
<220> FEATURE:
<223> OTHER INFORMATION: ClyA consensus sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
```

```
<220> FEATURE:
<221> NAME/KEY: misc_feature
<222> LOCATION: (33)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (218)..(218)
```

```
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (273)..(275)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
```

```
<222> LOCATION: (357)..(357)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (448)..(449)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (480)..(481)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
```

```
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (524)..(524)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (593)..(594)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (680)..(681)
<223> OTHER INFORMATION: n is a, c, g, or t
```

-continued

```
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (710)..(711)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (752)..(755)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (818)..(818)
```

```
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (893)..(894)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (911)..(911)
<223> OTHER INFORMATION: n is a, c, g, or t
<220> FEATURE:
<221> NAME/KEY: misc_feature
<222> LOCATION: (935)..(935)
<223> OTHER INFORMATION: n is a, c, g, or t
<220> FEATURE:
<221> NAME/KEY: misc_feature
<222> LOCATION: (938)..(938)
<223> OTHER INFORMATION: n is a, c, g, or t
<220> FEATURE:
<221> NAME/KEY: misc_feature
<222> LOCATION: (941)..(942)
<223> OTHER INFORMATION: n is a, c, g, or t
<220> FEATURE:
<221> NAME/KEY: misc_feature
<222> LOCATION: (947)..(947)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (962)..(962)
<223> OTHER INFORMATION: n is a, c, g, or t
<220> FEATURE:
<221> NAME/KEY: misc_feature
<222> LOCATION: (965)..(966)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t
<220> FEATURE:
<221> NAME/KEY: misc_feature
<222> LOCATION: (980)..(981)
<223> OTHER INFORMATION: n is a, c, g, or t
<220> FEATURE:
<221> NAME/KEY: misc_feature
```

```
<222> LOCATION: (989)..(993)
<223> OTHER INFORMATION: n is a, c, g, or t
<220> FEATURE:
<221> NAME/KEY: misc_feature
<222> LOCATION: (995)..(995)
<223> OTHER INFORMATION: n is a, c, g, or t
<220> FEATURE:
<221> NAME/KEY: misc_feature
<222> LOCATION: (1000)..(1001)
<223> OTHER INFORMATION: n is a, c, g, or t
<220> FEATURE:
<221> NAME/KEY: misc_feature
<222> LOCATION: (1004)..(1005)
<223> OTHER INFORMATION: n is a, c, g, or t
<220> FEATURE:
<221> NAME/KEY: misc_feature
<222> LOCATION: (1007)..(1007)
<223> OTHER INFORMATION: n is a, c, g, or t
<220> FEATURE:
<221> NAME/KEY: misc_feature
<222> LOCATION: (1012)..(1014)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1019)..(1021)
<223> OTHER INFORMATION: n is a, c, g, or t
<220> FEATURE:
<221> NAME/KEY: misc_feature
<222> LOCATION: (1026)..(1027)
<223> OTHER INFORMATION: n is a, c, g, or t
<220> FEATURE:
<221> NAME/KEY: misc_feature
<222> LOCATION: (1030)..(1031)
<223> OTHER INFORMATION: n is a, c, g, or t
<220> FEATURE:
<221> NAME/KEY: misc_feature
<222> LOCATION: (1033)..(1034)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t

<400> SEQUENCE: 12
ngangnaana nntannaata nnttntaaaa cannnnnttn attncaattt atatatttaa      60
agaggcnaat gattatgacn gnaatnnttg cagannaaac ngtagangta gttaaaancg     120
cnatcgaaac cgcagatggn gcattagatn tttataanaa atanctcgan caggtnatcc     180
cctggnagac ctttgatgaa accataaaag agttaagncg ntttaaacag gagtantcnc     240
aggnagcntc ngttttagtn ggngatatta aannnttnct tatggananc cagganaagt     300
attttgaagc nacncaaacn gtntatgaat ggtgtggtgt nngnacgcaa ttnctcncag     360
cgtatatttt nctatttgat gantanaatg agaanaaagc atcngcncag aaagacattc     420
tcatnangnt antngatgan ggnntcanna anctgaatga agcgcaaaaa tcnctnctgn     480
naagntcaca aagtttcaac aacgcttcng gnaaactgct ggcnttagat agccagttaa     540
cnaatgattt ntcngaaaaa agnagntatt tccagtcaca ggtngatana atnngnaagg     600
aagcntatgc cggtgcngca gcnggnnntg tcgccggtcc ntttggatta atnatttcct     660
attctattgc tgcgggcgtn nttgaaggna aantgattcc agaattgaan nacangntaa     720
aancngtgca naatttcttt acnancntnt cnnnnacngt naaacaagcg aataaagata     780
```

```
tcgatgcngc naaattgaaa ttanccacng aaatagcngc natnggngag ataaaaacgg      840
aaacngaaac aaccagattc tacgttgatt atgatgattt aatgctttct ttnntaaaag      900
nagcngcnaa naaaatgatt aacacctgta atgantanca nnaaagncac ggtaanaaga      960
cnctnntnga ggtncctgan ntctgatann nnntnattcn ntcnntntac tnnnaangnn     1020
ngatanngtn nannanatn                                                  1039

<210> SEQ ID NO 13
<211> LENGTH: 20
<212> TYPE: DNA
<213> ORGANISM: Artificial
<220> FEATURE:
<223> OTHER INFORMATION: primer sequence

<400> SEQUENCE: 13
tcgcaactct ctactgtttc                                                   20

<210> SEQ ID NO 14
<211> LENGTH: 54
<212> TYPE: DNA
<213> ORGANISM: Artificial
<220> FEATURE:
<223> OTHER INFORMATION: primer sequence

<400> SEQUENCE: 14
gcgatgaagc ttttaatggt gatggtgatg atgtttgtat agttcatcca tgcc             54

<210> SEQ ID NO 15
<211> LENGTH: 59
<212> TYPE: DNA
<213> ORGANISM: Artificial
<220> FEATURE:
<223> OTHER INFORMATION: primer sequence

<400> SEQUENCE: 15
gcgatggaat tcgagctctt aaagaggaga aaggtcatga gtaaaggaga agaactttt        59

<210> SEQ ID NO 16
<211> LENGTH: 54
<212> TYPE: DNA
<213> ORGANISM: Artificial
<220> FEATURE:
<223> OTHER INFORMATION: primer sequence

<400> SEQUENCE: 16
gcgatgaagc ttttaatggt gatggtgatg atgtttgtat agttcatcca tgcc             54
```

What is claimed:

1. A drug or vaccine delivery vehicle comprising an outer membrane cell vesicle expressing DsbA and displaying a ClyA fusion protein comprising at least a portion of a ClyA protein and at least a portion of a second protein.

2. The delivery vehicle of claim 1, wherein said cell vesicle contains the drug or vaccine to be delivered and wherein the second protein of the ClyA fusion protein comprises a targeting protein.

3. The delivery vehicle of claim 2, wherein said targeting protein is a cell specific ligand binding protein or an antigenic protein or peptide.

4. The delivery vehicle of claim 2, wherein the cell vesicle contains a nucleic acid, protein, or small molecule to be delivered.

5. The delivery vehicle of claim 4, wherein the cell vesicle contains an RNAi molecule.

6. The delivery vehicle of claim 1, wherein the second protein of the ClyA fusion protein displayed on the cell vesicle is an antigenic protein or peptide.

7. The delivery vehicle of claim 6, wherein the second protein of the ClyA fusion protein displayed on the cell vesicle surface is a vaccine subunit protein.

8. The delivery vehicle of claim 1, wherein the second protein is a marker protein.

9. The delivery vehicle of claim 8, wherein the marker protein is a fluorescent protein.

10. The delivery vehicle of claim 1, wherein the second protein is a ligand binding protein.

11. The delivery vehicle of claim 10, wherein the ligand binding protein is selected from the group consisting of high affinity antibody binding fragments, single-chain Fv antibody fragments, nanobodies, fluorobodies, aptamers, biotin-binding proteins, lipid-binding proteins, periplasmic binding proteins, lectins, serum albumins, enzymes, phosphate and sulfate binding proteins, immunophilins, metallothionein, and various other receptor proteins.

12. The delivery vehicle of claim 3, wherein the antigenic protein or peptide is a protein or peptide derived from pathogenic bacterial, fungal or viral organisms selected from the group consisting of *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (HIV), *Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cell antigens, transplant antigens, autoimmune antigens, and combinations.

13. The delivery vehicle of claim 1, wherein the second protein is a therapeutic protein.

14. The delivery vehicle of claim 1, wherein the second protein is an immunoregulatory protein.

15. The delivery vehicle of claim 1, wherein a plurality of ClyA fusion proteins are displayed on a plurality of cell vesicles.

16. The delivery vehicle of claim 15, wherein each of the plurality of ClyA fusion proteins comprises a different second polypeptide and wherein the plurality of ClyA fusion proteins form a library of polypeptides.

17. The delivery vehicle of claim 1, wherein the ClyA protein is a full length ClyA protein.

18. The delivery vehicle of claim 1, wherein the second protein is fused to the C terminus of the ClyA protein.

19. The delivery vehicle of claim 1, wherein the second protein is fused to the N terminus of the ClyA protein.

* * * * *